US012735507B2

(12) United States Patent
Nijjar et al.

(10) Patent No.: US 12,735,507 B2
(45) Date of Patent: Sep. 15, 2026

(54) ANTIBODIES RECOGNIZING TAU

(71) Applicant: PROTHENA BIOSCIENCES LIMITED, Dublin (IE)

(72) Inventors: Tarlochan S. Nijjar, Orinda, CA (US); Robin Barbour, Walnut Creek, CA (US); Philip James Dolan, III, Foster City, CA (US); Yue Liu, Foster City, CA (US); Svetlana Alexander, Sunnyvale, CA (US); Mark E. Renz, Millbrae, CA (US)

(73) Assignee: Prothena Biosciences Limited, Dublin (IE)

( * ) Notice: Subject to any disclaimer, the term of this patent is extended or adjusted under 35 U.S.C. 154(b) by 1104 days.

(21) Appl. No.: 17/291,986

(22) PCT Filed: Nov. 8, 2019

(86) PCT No.: PCT/US2019/060616

§ 371 (c)(1),
(2) Date: May 6, 2021

(87) PCT Pub. No.: WO2020/097561

PCT Pub. Date: May 14, 2020

(65) Prior Publication Data

US 2022/0153821 A1 May 19, 2022

Related U.S. Application Data

(60) Provisional application No. 62/758,421, filed on Nov. 9, 2018.

(30) Foreign Application Priority Data

Nov. 8, 2018 (WO) ................ PCT/US2018/059895

(51) Int. Cl.

*C07K 16/46* (2006.01)
*A61K 47/68* (2017.01)
*C07K 16/18* (2006.01)

(52) U.S. Cl.

CPC ........ *C07K 16/461* (2013.01); *A61K 47/6843* (2017.08); *C07K 16/18* (2013.01); *C07K 2317/24* (2013.01); *C07K 2317/52* (2013.01); *C07K 2317/55* (2013.01); *C07K 2317/622* (2013.01); *C07K 2317/92* (2013.01)

(58) Field of Classification Search

CPC .. C07K 16/461; C07K 16/18; C07K 2317/24; C07K 2317/52; C07K 2317/55; C07K 2317/622; C07K 2317/92; C07K 2317/76; C07K 2317/94; C07K 2317/565; C07K 2317/56; A61K 47/6843; A61K 2039/505; A61P 25/28; A61P 25/00; A61P 25/16; G01N 33/6896; G01N 2800/52; G01N 33/58; G01N 33/582; G01N 33/60; G01N 2333/47; C12N 2015/8518; C12N 15/85; C12N 2510/00; C12N 2800/107; C12R 2001/91

See application file for complete search history.

(56) References Cited

U.S. PATENT DOCUMENTS 4,634,664 A 1/1987 Oestberg
4,634,666 A 1/1987 Engleman et al.
5,057,540 A 10/1991 Kensil et al.
5,194,594 A 3/1993 Khawli et al.
5,208,036 A 5/1993 Eppstein et al.
5,225,539 A 7/1993 Winter
5,264,618 A 11/1993 Felgner et al.
5,279,833 A 1/1994 Rose
5,283,185 A 2/1994 Epand et al.
5,304,489 A 4/1994 Rosen
5,530,101 A 6/1996 Queen et al.
5,545,806 A 8/1996 Lonberg et al.
5,565,332 A 10/1996 Hoogenboom et al.
5,569,825 A 10/1996 Lonberg et al.
5,585,089 A 12/1996 Queen et al.
5,624,821 A 4/1997 Winter et al.
5,625,126 A 4/1997 Lonberg et al.
5,633,425 A 5/1997 Lonberg et al.
5,643,576 A 7/1997 Johnston et al.
5,661,016 A 8/1997 Lonberg et al.
5,733,743 A 3/1998 Johnson et al.
5,736,142 A 4/1998 Sette et al.
5,741,957 A 4/1998 Deboer et al.
5,770,429 A 6/1998 Lonberg et al.
5,786,464 A 7/1998 Seed et al.

(Continued)

FOREIGN PATENT DOCUMENTS

CN 103339146 10/2013
CN 104185640 12/2014

(Continued)

OTHER PUBLICATIONS

Nohubara et al. Tau Antibody Targeting Pathological Species Blocks Neuronal Uptake and Interneuron Propagation of Tau in Vitro. Am J Pathol. Jun. 2017; 187(6):1399-1412. (Year: 2017).*

(Continued)

*Primary Examiner* — Julie Wu
*Assistant Examiner* — Amber K Faust
(74) *Attorney, Agent, or Firm* — Fish & Richardson P.C.

(57) ABSTRACT

The invention provides antibodies that specifically bind tau. The antibodies inhibit or delay tau-associated pathologies and associated symptomatic deterioration.

17 Claims, 5 Drawing Sheets

Specification includes a Sequence Listing.

(56) References Cited

U.S. PATENT DOCUMENTS 5,789,650 A 8/1998 Lonberg et al.
5,814,318 A 9/1998 Lonberg et al.
5,834,597 A 11/1998 Tso et al.
5,837,242 A 11/1998 Holliger et al.
5,849,992 A 12/1998 Meade et al.
5,858,657 A 1/1999 Winter et al.
5,859,205 A 1/1999 Adair et al.
5,871,907 A 2/1999 Winter et al.
5,874,299 A 2/1999 Lonberg et al.
5,877,218 A 3/1999 Herzig et al.
5,877,397 A 3/1999 Lonberg et al.
5,888,809 A 3/1999 Allison et al.
6,063,598 A 5/2000 Enenkel et al.
6,114,148 A 9/2000 Seed et al.
6,407,213 B1 6/2002 Carter et al.
6,624,821 B1 9/2003 Shin et al.
6,881,557 B2 4/2005 Foote
7,442,516 B2 10/2008 Ohno et al.
7,569,339 B2 8/2009 Kaufmann et al.
8,012,936 B2 9/2011 Sigurdsson et al.
8,455,622 B2 6/2013 McDonagh et al.
8,778,343 B2 7/2014 Kayed
8,926,974 B2 1/2015 Griswold-Prenner et al.
8,987,419 B2 3/2015 Barghorn et al.
9,051,367 B2 6/2015 Griswold-Prenner et al.
9,321,841 B2 4/2016 Jones et al.
9,605,054 B2 3/2017 Brady et al.
10,196,439 B2 2/2019 Pedersen et al.
10,253,100 B2 4/2019 Igawa et al.
10,301,379 B2 5/2019 Wadia et al.
10,501,531 B2 12/2019 Seubert et al.
10,711,058 B2 7/2020 Adolfsson et al.
10,752,679 B2 8/2020 Seubert et al.
10,766,953 B2 9/2020 Mercken et al.
10,829,547 B2 11/2020 Roberts et al.
10,836,817 B2 11/2020 Adolfsson et al.
10,889,638 B2 1/2021 Barbour et al.
10,906,964 B2 2/2021 Barbour et al.
10,961,302 B2 3/2021 Barbour et al.
2005/0009150 A1 1/2005 Basi et al.
2005/0114912 A1 5/2005 Botas et al.
2005/0132424 A1 6/2005 Lowe et al.
2007/0042359 A1 2/2007 Throsby et al.
2008/0050383 A1 2/2008 Sigurdsson et al.
2008/0076145 A1 3/2008 Cummings et al.
2009/0028851 A1 1/2009 Stuhmer et al.
2010/0022026 A1 1/2010 Rump et al.
2010/0216703 A1 8/2010 Akassoglou et al.
2010/0267927 A1 10/2010 Garrett et al.
2010/0316564 A1 12/2010 Sigurdsson
2011/0053264 A1 3/2011 Kashmiri et al.
2011/0206702 A1 8/2011 Polakis et al.
2012/0023911 A1 2/2012 Liu et al.
2012/0100152 A1 4/2012 Roberts et al.
2012/0142602 A1 6/2012 Brady et al.
2012/0149880 A1 6/2012 Cheung et al.
2012/0204275 A1 8/2012 Schenk et al.
2012/0288507 A1 11/2012 Qian et al.
2012/0301473 A1 11/2012 Binder et al.
2012/0308480 A1 12/2012 Smith et al.
2013/0189289 A1 7/2013 Inoue et al.
2013/0209453 A1 8/2013 Black et al.
2013/0295021 A1 11/2013 Chen et al.
2014/0056901 A1 2/2014 Agadjanyan et al.
2014/0086921 A1 3/2014 Griswold-Prenner et al.
2014/0171373 A1 6/2014 Ashe et al.
2014/0294731 A1 10/2014 Pfeifer et al.
2014/0294839 A1 10/2014 Kuret et al.
2015/0050215 A1 2/2015 Novak et al.
2015/0050270 A1 2/2015 Sanofi
2015/0056721 A1 2/2015 Siman
2015/0166661 A1 6/2015 Chen et al.
2015/0175682 A1 6/2015 Pfeifer et al.
2015/0196663 A1 7/2015 Shusta et al.
2015/0253341 A1 9/2015 McAvoy et al.
2015/0266947 A1 9/2015 Sierks et al.
2015/0344553 A1 12/2015 Weinreb et al.
2016/0031976 A1 2/2016 Seubert et al.
2016/0289309 A1 10/2016 Griswold-Prenner et al.
2016/0376341 A1 12/2016 Adolfsson et al.
2017/0355756 A1 12/2017 Julien et al.
2018/0142007 A1 5/2018 Novak et al.
2018/0209994 A1 7/2018 Lannfelt et al.
2019/0322728 A1 10/2019 Seubert et al.
2019/0330314 A1 10/2019 Barbour et al.
2019/0330316 A1 10/2019 Barbour et al.
2020/0030445 A1 1/2020 John et al.
2020/0123239 A1 4/2020 Seubert et al.
2020/0131255 A1 4/2020 Kerchner et al.
2020/0181245 A1 6/2020 Masliah et al.
2021/0023216 A1 1/2021 Angstenberger et al.
2021/0032319 A1 2/2021 Seubert et al.
2021/0130449 A1 5/2021 Barbour et al.
2021/0261652 A1 8/2021 Nijjar et al.
2023/0250161 A1* 8/2023 Barbour ............. G01N 33/6896 424/139.1

FOREIGN PATENT DOCUMENTS

EP 0673418 B1 5/1998
EP 1355949 B1 3/2010
EP 3080611 B1 11/2018
GB 2220211 1/1990
JP 2009-056790 A 2/2009
JP 2010-511388 A 4/2010
JP 2011-501655 A 1/2011
JP 2011-521623 A 7/2011
JP 2012-500020 A 1/2012
JP 2014-530597 A 11/2014
JP 2015-520685 A 7/2015
JP 2015-530971 10/2015
JP 2016-512551 A 4/2016
WO WO 91/10741 7/1991
WO WO 91/17271 11/1991
WO WO 92/01047 1/1992
WO WO 92/20791 11/1992
WO WO 93/12227 6/1993
WO WO 94/12629 6/1994
WO WO 95/07707 3/1995
WO WO 1996/15452 A1 5/1996
WO WO 96/34625 11/1996
WO WO 98/23635 6/1998
WO WO 98/40100 9/1998
WO WO 00/072880 12/2000
WO WO 03/057838 7/2003
WO WO 2004/050884 6/2004
WO WO 2005/019442 3/2005
WO WO 2008/012142 1/2008
WO WO 2008/081008 7/2008
WO WO 2008/103472 8/2008
WO WO 2008/107388 9/2008
WO WO 2009/027471 3/2009
WO WO 2009/134711 A1 11/2009
WO WO 2011/053565 A2 5/2011
WO WO 2011/154321 A1 12/2011
WO WO 2012/049570 A1 4/2012
WO WO 2013/004717 A1 1/2013
WO WO 2013/007839 A1 1/2013
WO WO 2013/028810 A1 2/2013
WO WO 2013/041962 A1 3/2013
WO WO-2013151762 A1 * 10/2013 ............. A61P 25/28
WO WO 2014/008404 A1 1/2014
WO WO 2014/1006000 A2 6/2014
WO WO 2014/152157 A2 9/2014
WO WO 2014/165271 A2 10/2014
WO WO 2014/165271 A3 10/2014
WO WO 2015/197823 A3 2/2016
WO WO 2016/079597 A1 5/2016
WO WO 2016/137950 A1 9/2016
WO 2016/196726 A1 12/2016
WO WO 2015/200806 A1 12/2016
WO WO 2016/196726 A9 12/2016
WO WO 2017/005732 A1 1/2017
WO WO 2017/062672 A2 4/2017

(56) References Cited

FOREIGN PATENT DOCUMENTS

| | | | |
|---|---|---|---|
| WO | WO 2017/091512 | | 6/2017 |
| WO | WO 2017/191559 | A1 | 11/2017 |
| WO | WO 2017/191560 | A1 | 11/2017 |
| WO | WO 2017/191561 | A1 | 11/2017 |
| WO | WO 2018/017370 | | 1/2018 |
| WO | WO 2018/106781 | A1 | 6/2018 |
| WO | WO 2018/107125 | A1 | 6/2018 |
| WO | WO 2018/152359 | A1 | 8/2018 |
| WO | WO 2018/156250 | A1 | 8/2018 |
| WO | WO 2018/178077 | A1 | 10/2018 |
| WO | WO 2018/204546 | A2 | 11/2018 |
| WO | WO 2018/231254 | A1 | 12/2018 |
| WO | WO 2019/094595 | A2 | 5/2019 |
| WO | WO 2019/110571 | A1 | 6/2019 |
| WO | WO 2019/186276 | A2 | 10/2019 |
| WO | WO 2019/207159 | A1 | 10/2019 |
| WO | WO 2020/096608 | A1 | 5/2020 |
| WO | WO 2020/097561 | A1 | 5/2020 |
| WO | WO 2020/106598 | A1 | 5/2020 |
| WO | WO 2020/163817 | A1 | 8/2020 |
| WO | WO 2020/180819 | A1 | 9/2020 |
| WO | WO 2020/193520 | A1 | 10/2020 |
| WO | WO 2021/010712 | A1 | 1/2021 |

OTHER PUBLICATIONS

Almagro et al. Progress and Challenges in the Design and Clinical Development of Antibodies for Cancer Therapy. Front Immunol. Jan. 4, 2018;8:1751 (Year: 2008).*

Gonzales et al., "Minimizing the Immunogenicity of Antibodies for Clinical Application," Tumour Biol., Jan./Feb. 2005, 26(1):31-43.

Kunik et al., "Structural consensus among antibodies defines the antigen binding site," PLoS Comput Biol., Feb. 23, 2012, 8(2):e1002388, 12 pages.

Panka et al., "Variable region framework differences result in decreased or increased affinity of variant anti-digoxin antibodies," Proc Natl Acad Sci USA, May 1988, 85(9):3080-4.

Sela-Culang et al., "The Structural Basis of Antibody-Antigen Recognition," Front. Immunol., Oct. 8, 2013, 4:302, 13 pages.

Wark et al., et al., "Latest technologies for the enhancement of antibody affinity," Adv. Drug Deliv. Rev., Aug. 7, 2006, 58(5-6):657-670.

Goedert, et al., "Cloning and sequencing of the cDNA encoding a core protein of the paired helical filament of Alzheimer disease: Identification as the microtubule-associated protein tau" Proc. Natl. Acad. Sci. USA, vol. 85, pp. 4051-4055, (Jun. 1998).

PCT/US2014/025044 International Search Report and Written Opinion mailed Nov. 3, 2014.

Vigo-Pelfrey, et al., "Elevation of microtubule-associated protein tau in the cerebrospinal fluid of patients with Alzheimer's disease", *Neurology*, 45:788-793 (Apr. 1995).

PCT/US2014/025044 Invitation to Pay Additional Fees and, Where Applicable, Protest Fee mailed Aug. 15, 2014.

EP 14778358.2 European Supplementary Search Report completed Nov. 3, 2016.

Castillo-Carranza, et al., "Tau aggregates as immunotherapeutic targets," *Frontiers in Bioscience, Scholar*, 5, 426-438 (Jan. 1, 2013).

Ghoshal, et al., "Tau Conformational Changes Correspond to Impairments of Episodic Memory in Mild Cognitive Impairment and Alzheimer's Disease," *Experimental Neurology*, 177, 475-493, (Jun. 2002).

Jicha, et al., "Sequence Requirements for Formation of Conformational Variants of Tau Similar to Those Found in Alzheimer's Disease," *Journal of Neuroscience Research*, 55:713-723 (Dec. 1999).

Morris, "Epitope Mapping of Protein Antigens by Competition ELISA," *The Protein Protocols Handbook*, edited by J. M. Walker, Humana Press Inc., Totowa, NJ, pp. 595-600, (Jan. 1, 1996).

Dubel, "Molecular Engineering I: Humanization," *Handbook of Therapeutic Antibodies*, Chapter 6:119-144, (2007).

Yanamandra, et al., "Anti-Tau Antibodies that Block Tau Aggregate Seeding In Vitro Markedly Decrease Pathology and Improve Cognition in Vivo," *Neuron*, 80, 402-414 (Oct. 15, 2013).

PCT/US2014/025044 International Preliminary Report on Patentability completed Oct. 9, 2014.

U.S. Appl. No. 14/776,724 Restriction Requirement mailed Jan. 19, 2017.

U.S. Appl. No. 14/776,724 Non-Final Office Action mailed Jun. 1, 2017.

Chen, et al., "Enhancement and destruction of antibody function by somatic mutation: unequal occurrence is controlled by V gene combinatorial associations," *the EMBO Journal*, vol. 14, No. 12, pp. 2784-2794 (1995).

Kussie, et al., "A Single Engineered Amino Acid Substitution Changes Antibody Fine Specificity," *J Immunol*, 152(1):146-52 (1994).

Oddo, et al., "Reduction of Soluble Aβ and Tau, but Not Soluble Aβ Alone, Ameliorates Cognitive Decline in Transgenic Mice with Plaques and Tangles," *The Journal of Biological Chemistry*, vol. 281, No. 51, pp. 39413-39423 (Dec. 22, 2016).

Hasegawa, et al., "Characterization of Two distinct Monoclonal Antibodies to Paired Helical Filaments: Further Evidence for Fetal-Type Phosphorylation of the T in Paired Helical Filaments", Journal of Neurochemistry, vol. 60, No. 6, (1993).

Leger, et al., "Antibody Drug Discovery Chapter 1: Humanization of Antibodies", Molecular medicine and Medicinal Chemistry, pp. 1-23 XP055119233 (Jan. 1, 2011).

Almagro, et al., "Humanization of antibodies", *Frontiers in Bioscience*, 13, 1619-1653, (Jan. 1, 2008).

Lazar, et al., "A molecular immunology approach to antibody humanization and functional optimization", *Molecular Immunology*, 44:1986-1998 (2007).

Wu, et al., "Simultaneous Humanization and Affinity Optimization of Monoclonal Antibodies", *Methods of Molecular Biology*, vol. 207: Recombinant Antibodies for Cancer Therapy: Methods and Protocols, Edited by M. Weischof and J. Krauss @ Humana Press Inc., Tolowa NJ, pp. 197-212 (Jan. 1, 2003).

PCT/IB2017/052544 Search Report and Written Opinion mailed Jul. 31, 2017.

PCT/IB2017/052545 Search Report and Written Opinion mailed Aug. 1, 2017.

Bacskai, et al., "Imaging of amyloid-β deposits in brains of living mice permits direct observation of clearance of plaques with immunotherapy," *Nature Medicine*, vol. 7, No. 3, pp. 369-372, (Mar. 2001).

PCT/IB2017/052544 Search Report and Written Opinion mailed Jul. 19, 2017.

Agadjanyan, et al., "Humanized monoclonal antibody armanezumab specific to N-terminus of pathological tau: characterization and therapeutic potency," *Molecular Neurodegeneration*, 12:33, DOI 10.1186/s13024-017-0172-1, (2017).

Kontsekova, et al., "First-in-man tau vaccine targeting structural determinants essential for pathological tau-tau interaction reduces tau oligomerisation and neurofibrillary degeneration in an Alzheimer's disease model," *Alzheimer's Research & Therapy*, 6:44, (2014).

Rosseels, et al., "Tau Monoclonal Antibody Generation Based on Humanized Yeast Models," *Journal of Biological Chemistry*, vol. 290, No. 7, pp. 4059-4074, (Dec. 24, 2014).

PCT/IB2017/052543 International Report on Patentability issued Nov. 6, 2018.

PCT/IB2017/052544 International Report on Patentability issued Nov. 6, 2018.

PCT/IB2017/052545 International Report on Patentability issued Nov. 6, 2018.

U.S. Appl. No. 14/776,724 Final Office Action mailed Oct. 31, 2018.

U.S. Appl. No. 14/776,724 Advisory Action mailed Mar. 12, 2019.

U.S. Appl. No. 14/776,724 Notice of Allowance mailed Apr. 10, 2019.

PCT/US2018/030739 International Search Report and Written Opinion mailed Nov. 5, 2018.

PCT/US2018/059895 International Search Report and Written Opinion mailed Apr. 12, 2019.

(56) References Cited

OTHER PUBLICATIONS

PCT/US2018/030739 International Search Report and Written Opinion mailed Sep. 18, 2018.
U.S. Appl. No. 14/776,724 Notice of Allowance mailed Jul. 29, 2019.
U.S. Appl. No. 16/091,060 Restriction Requirement mailed Sep. 17, 2019.
U.S. Appl. No. 16/092,439 Notice of Allowance mailed Oct. 16, 2019.
Pedersen, et al., "Tau immunotherapy for Alzheimer's disease," Trends in Molecular Medicine, vol. 21, No. 6, pp. 394-402, (Jun. 2015).
PCT/US2018/030739 International Preliminary Report on Patentability mailed Nov. 5, 2019.
U.S. Appl. No. 16/097,445 Restriction Requirement mailed Feb. 18, 2020.
U.S. Appl. No. 16/091,060 Non-Final Office Action mailed Feb. 21, 2020.
U.S. Appl. No. 16/092,439 Notice of Allowance and Interview Summary mailed Apr. 10, 2020.
PCT/US2019/060616 International Search Report and Written Opinion mailed Mar. 20, 2020.
PCT/US2020/017357 Invitation to Pay Additional Fees mailed Apr. 23, 2020.
U.S. Appl. No. 16/097,445 Non-Final Office Action mailed May 27, 2020.
PCT/US2020/017357 International Search Report and Written Opinion mailed Jun. 17, 2020.
Kawahara, et al., "The Novel Monoclonal Antibody 9F5 Reveals Expression of a Fragment of GPNMB/Osteoactivin Processed by Furin-like Protease(s) in a Subpopulation of Microglia in Neonatal Rat Brain," GLIA, vol. 64, No. 11, pp. 1938-1961, (Nov. 2016).
Strang, et al., "Generation and characterization of new monoclonal antibodies targeting the PHF1 and AT8 epitopes on human tau," Acta Neuropathologica Communications, 5:58, (2017).
Croft, et al., "Novel monoclonal antibodies targeting the microtubule-binding domain of human tau," PLoS ONE, 13(4): e0195211, (Apr. 2018).
PCT/US2020/020704 Invitation to Pay Additional Fees mailed Jun. 3, 2020.
EP 19213368 Extended European Search Report mailed Jun. 24, 2020.
Florenzano, et al., "Extracellular truncated tau causes early presynaptic dysfunction associated with Alzheimer's disease and other tauopathies," Oncotarget, vol. 8, No. 29, pp. 64745-46778, (Apr. 2017).
Gershoni, et al., "Epitope Mapping, The First Step in Developing Epitope-Based Vaccines," Biodrugs, 21:(3), p. 145-156. (2007).
PCT/US2020/020704 Search Report and Written Opinion mailed Aug. 4, 2020.
U.S. Appl. No. 16/091,060 Notice of Allowance and Interview Summary mailed Aug. 19, 2020.
U.S. Appl. No. 16/097,445 Corrected Notice of Allowance mailed Oct. 6, 2020.
U.S. Appl. No. 16/097,445 Notice of Allowance mailed Oct. 2, 2020.
EP 18795047 Extended European Search Report mailed Feb. 2, 2021.
U.S. Appl. No. 16/667,647 Restriction Requirement mailed Jan. 13, 2021.
U.S. Appl. No. 16/808,209 Notice of Allowance mailed Dec. 31, 2020.
PCT/US2018/059895 International Preliminary Report on Patentability mailed May 11, 2021.
PCT/US2019/060616 International Preliminary Report on Patentability mailed May 11, 2021.
U.S. Appl. No. 16/667,647 Non-Final Office Action mailed Jun. 28, 2021.
Ladner, "Mapping the Epitopes of Antibodies," Biotechnology and Genetic Engineering Reviews, vol. 24, 1-30, (2007).
PCT/US2020/017357 International Preliminary Report on Patentability mailed Aug. 10, 2021.
PCT/US2020/020704 International Preliminary Report on Patentability mailed Aug. 25, 2021.
Yanamandra et al., "Anti-tau antibody reduces insoluble tau and decreases brain atrophy," Annals of Clinical and Translational Neurology 2, 278-288 (2015).
U.S. Appl. No. 16/933,792 Non-Final Office Action mailed Dec. 15, 2021.
Alexander et al., "Development of High Potency Universal DR-Restricted Helper Epitopes by Modification of High Affinity DR-Blocking Peptides," Immunity, Dec. 1994, 1:751-761.
Andreadis et al., "Structure and novel exons of the human .tau. gene," Biochemistry, 1992, 31:10626-10633.
Atwal et al., "A Therapeutic Antibody Targeting BACE1 Inhibits Amyloid-β Production in Vivo," Sci. Translation Med., May 2011, 84(3):1-12.
Banner et al., "Mapping the conformational space accessible to BACE2 using surface mutants and cocrystals with Fab fragments, Fynomers and Xaperones," Acta. Crystallogr. D. Biol. Crystallogr., 2013, 69(Pt6): 1124-1137.
Bertschinger et al., "Selection of single domain binding proteins by covalent DNA display," Protein Eng. Des. Sel., Feb. 2007, 20:57-68.
Bett et al., "Packaging Capacity and Stability of Human Adenovirus Type 5 Vectors," J. Virol., 1993, 67:5911-5921.
Boris-Lawrie et al., "Recent advances in retrovirus vector technology," Current Opinion in Genetics & Development, Feb. 1993, 3(1):102-109.
Brack et al., "A bispecific HER2-targeting FynomAb with superior antitumor activity and novel mode of action," Mol. Cancer Ther., 2014, 13:2030-2039.
Chicz et al., "Specificity and promiscuity among naturally processed peptides bound to HLA-DR alleles," J. Exp. Med., Jul. 1993, 178(1):27-47.
Chothia et al., "Canonical structures for the hypervariable regions of immunoglobulins," Journal of Molecular Biology, Aug. 1987, 196(4):901-917.
Chothia et al., "Conformations of immunoglobulin hypervariable regions," Nature, Dec. 1989, 342:878-883.
Co et al., "Chimeric and humanized antibodies with specificity for the CD33 antigen," J. Immunol., Feb. 1992, 148(4): 1149-1154.
Dafferner et al., "Immunopurification of Acetylcholinesterase from Red Blood Cells for Detection of Nerve Agent Exposure," Chemical Research in Toxicology, 2017, 30(10):1897-1910.
Deshpande et al., "The RCSB Protein Data Bank: a redesigned query system and relational database based on the mmCIF schema," Nucleic Acids Res., Jan. 2005, 33:D233-D237.
Dubensky et al., "Sindbis virus DNA-based expression vectors: utility for in vitro and in vivo gene transfer," J. Virol., Jan. 1996, 70(1):508-519.
Edelman et al., "The Covalent Structure of an Entire y G Immunoglobulin Molecule," Proc. Natl. Acad. USA, May 1969, 63(1)78-85.
Extended European Search Report in European Appln No. 19881978.1, dated Jul. 12, 2022, 9 pages.
Falk et al., "Pool sequencing of natural HLA-DR, DQ, and DP ligands reveals detailed peptide motifs, constraints of processing, and general rules," Immunogenetics, 1994, 39:230-242.
Foote et al., "Antibody framework residues affecting the conformation of the hypervariable loops," Journal of Molecular Biology, Mar. 1992, 224(2):487-499.
Friden et al., "Anti-transferrin receptor antibody and antibody-drug conjugates cross the blood-brain barrier," Proc. Natl. Acad Sci. USA, Jun. 1991, 88(11):4771-4775.
Friden et al., "Blood-Brain Barrier Penetration and in Vivo Activity of an NGF Conjugate," Science, Jan. 1993, 259(5093):373-377.
GenBank Accession No. AAZ09048.1, "immunoglobulin kappa light chain variable region, partial [*Homo sapiens*]," Jul. 26, 2016, 2 pages.
GenBank Accession No. ARX71335.1, "anti-human acetylcholinesterase immunoglobulin light chain variable region, partial [*Homo sapiens*]," Jun. 14, 2017, 3 pages.

(56) References Cited

OTHER PUBLICATIONS

GenBank Accession No. BAC01986.1, "immunoglobulin heavy chain VHDJ region, partial [*Homo sapiens*]," Jul. 26, 2016, 2 pages.
Goedert et al., "Cloning and sequencing of the cDNA encoding an isoform of microtubule-associated protein tau containing four tandem repeats: differential expression of tau protein mRNAs in human brain," EMBO J., 1989, 8:393-399.
Goedert et al., "Multiple isoforms of human microtubule-associated protein tau: sequences and localization in neurofibrillary tangles of Alzheimer's disease," Neuron, Oct. 1989, 3(4):519-526.
Gonzales et al., "SDR grafting of a murine antibody using multiple human germline templates to minimize its immunogenicity," Mol. Immunol., Jul. 2004, 41(9):863-872.
Grabulovski et al., "A Novel, Non-immunogenic Fyn SH3-derived Binding Protein with Tumor Vascular Targeting Properties," J Biol. Chem., Feb. 2007, 282(5):3196-3204.
Hammer et al., "Promiscuous and allele-specific anchors in HLA-DR-binding peptides," Cell, Jul. 1993, 74(1):197-203.
Hazra et al., "Linking radiosilver to monoclonal antibodies reduced by ascorbic acia," Cell Biophys., Jan. 1994, 24-25:1-7.
Hinton et al., "Engineered Human IgG Antibodies with Longer Serum Half-lives in Primates," J. Biol. Chem., Feb. 2004, 279(8):6213-6216.
Ittner et al., "Parkinsonism and impaired axonal transport in a mouse model of frontotemporal dementia," Proc. Natl. Acad. Sci. USA, Oct. 2008, 105(41):15997-16002.
Iwahashi et al., "CDR substitutions of a humanized monoclonal antibody (CC49): contributions of individual CDRs to antigen binding and immunogenicity," Mol. Immunol., 1999, 36(15-16): 1079-1091.
Jack et al., "Hypothetical model of dynamic biomarkers of the Alzheimer's pathological cascade," The Lancet Neurology, Jan. 2010, 9(1):119-128.
Jones et al., "The INNs and outs of antibody nonproprietary names," mAbs, 2016, 8(1):1-9.
Junghans et al., "Anti-Tac-H, a Humanized Antibody to the Interleukin 2 Receptor with New Features for Immunotherapy in Malignant and Immune Disorders," Cancer Res., Mar. 1990, 50(5): 1495-1502.
Khlistunova et al., "Inhibition of Tau Aggregation in Cell Models of Tauopathy," Current Alzheimer Research, 2007, 4(5):544-546.
Kostelny et al., "Formation of a bispecific antibody by the use of leucine zippers," Journal of Immunology, Mar. 1992, 148(5):1547-1553.
Lazar et al., "Engineered antibody Fc variants with enhanced effector function," Proc. Natl. Acad. Sci. USA, Mar. 2006, 103(11):4005-4010.
Lee et al., "The microtubule binding domain of tau protein," Neuron, Jun. 1989, 2(6):1615-1624.
Lefranc et al., "IMGT unique numbering for immunoglobulin and T cell receptor constant domains and Ig superfamily C-like domains," Dev. Comp. Immunol., 2005, 29(3):185-203.
Lewis et al., "Neurofibrillary tangles, amyotrophy and progressive motor disturbance in mice expressing mutant (P301L) tau protein," Nature Genetics, 2000, 25:402-405.
Liu et al., "N-terminal Glutamate to Pyroglutamate Conversion in Vivo for Human IgG2 Antibodies," J. Biol. Chem., Apr. 2011, 286(13):11211-11217.
Martin et al., "Structural Families in Loops of Homologous Proteins: Automatic Classification, Modelling and Application to Antibodies," Journal of Molecular Biology, Nov. 1996, 263(5):800-815.
McGee et al., "The encapsulation of a model protein in poly (D, L lactide-co-glycolide) microparticles of various sizes: an evaluation of process reproducibility," Journal of Microencapsulation, 1997, 14(2):197-210.
Neuberger, "Generating high-avidity human mabs in mice," Nat. Biotechnol., 1996, 14:826.
Ohe et al., "Construction of a Novel Bovine Papillomavirus Vector Without Detectable Transforming Activity Suitable for Gene Transfer," Human Gene Therapy, 1995, 6(3):325-333.
Ostberg et al., "Human X (Mouse X Human) Hybridomas Stably Producing Human Antibodies," Hybridoma, 1983, 2(4):361-367.
Padlan, "A possible procedure for reducing the immunogenicity of antibody variable domains while preserving their ligand-binding properties," Mol. Immunol., 1991, 28(4-5):489-498.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," J Immunol., Sep. 2002, 169(6):3076-3084.
Piechotta et al., "Structural and functional analyses of pyroglutamate-amyloid-β-specific antibodies as a basis for Alzheimer immunotherapy," Journal of Biological Chemistry, Jul. 2017, 292(30):12713-12724.
Pietersz et al., "Novel Synthesis and in Vitro Characterization of Disulfide-linked Ricin-Monoclonal Antibody Conjugates Devoid of Galactose Binding Activity," Cancer Research, Aug. 1988, 48(16):4469-4476.
Polito et al., "The conjugate Rituximab/saporin-S6 completely inhibits clonogenic growth of CD20-expressing cells and produces a synergistic toxic effect with Fludarabine," Leukemia, 2004, 18:1215-1222.
Poorkaj et al., "Tau is a candidate gene for chromosome 17 frontotemporal dementia," Annals of Neurology, 1998, 43(6):815-825.
Powilleit et al., "Exploiting the Yeast L-A Viral Capsid for the In Vivo Assembly of Chimeric VLPs as Platform in Vaccine Development and Foreign Protein Expression," PLoS ONE, May 2007, 2(5):e415.
Queen et al., "Cell-Type Specific Regulation of a K Immunoglobulin Gene by Promoter and Enhancer Elements," Immunol. Rev., Feb. 1986, 89(1):49-68.
Schiele et al., "Structure-guided residence time optimization of a dabigatran reversal agent," mAbs, 2015, 7(5):871-880.
Schilling et al., "Glutaminyl cyclases from animals and plants: a case of functionally convergent protein evolution," Biol. Chem., Aug. 2008, 389(8):983-991.
Schlatter et al., "Generation, characterization and structural data of chymase binding proteins based on the human Fyn kinase SH3 domain," mAbs, 2012, 4:497-508.
Sinigaglia et al., "A malaria T-cell epitope recognized in association with most mouse and human MHC class II molecules," Nature, Dec. 1988, 336:778-780.
Songsivilai et al., "Bispecific antibody: a tool for diagnosis and treatment of disease," Clin. Exp. Immunol., Mar. 1990, 79(3):315-321.
Southwood et al., "Several Common HLA-DR Types Share Largely Overlapping Peptide Binding Repertoires," J. Immunology, Apr. 1998, 160(7):3363-3373.
Stoute et al., "A Preliminary Evaluation of a Recombinant Circumsporozoite Protein Vaccine against Plasmodium falciparum Malaria," The New England Journal of Medicine, Jan. 1997, 336(2):86-91.
Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, Feb. 2000, 164(3):1432-1441.
Thorpe et al., "The Preparation and Cytotoxic Properties of Antibody-Toxin Conjugates," Immunological Reviews, Feb. 1982, 62(1):119-158.
UniProt Accession No. P10636, "Microtubule-associated protein tau," Jan. 16, 2019, 32 pages.
Vajdos et al., "Comprehensive Functional Maps of the Antigen-binding Site of an Anti-ErbB2 Antibody Obtained with Shotgun Scanning Mutagenesis," Journal of Molecular Biology, Jul. 2002, 320(2):415-428.
Wang et al., "Two-Stage PCR Protocol Allowing Introduction of Multiple Mutations, Deletions and Insertions Using QuikChangeTM Site-Directed Mutagenesis," BioTechniques, 1999, 26(4):680-682.
Wedemayer et al., "Structural Insights into the Evolution of an Antibody Combining Site," Science, Jun. 1997, 276(5319):1665-1669.

(56) References Cited

OTHER PUBLICATIONS who.int [online], "International Nonproprietary Names (INN) for biological and biotechnological substances (a review)," available on or before Aug. 24, 2015, via Internet Archive: Wayback Machine URL <https://web.archive.org/web/20210000000000*/http://www.who.int/medicines/services/inn/BioRev2014.pdf>, retrieved on Aug. 9, 2022, URL <http://www.who.int/medicines/services/inn/BioRev2014.pdf>, 81 pages.
Witzig, "Radioimmunotherapy for patients with relapsed B-cell non-Hodgkin lymphoma," Cancer Chemotherapy and Pharmacology, Jul. 2001, 48:S91-S95.
Wu et al., "Generation and Characterization of a Dual Variable Domain Immunoglobulin (DVD-Ig™) Molecule," Antibody Engineering, 2010, 2:239-250.
Xiao et al., "High Efficiency, Long-Term Clinical Expression of Cottontail Rabbit Papillomavirus (CRPV) DNA in Rabbit Skin Following Particle-Mediated DNA Transfer," Nucleic Acids. Res., Jul. 1996, 24(13):2620-2622.
Yu et al., "Boosting Brain Uptake of a Therapeutic Antibody by Reducing Its Affinity for a Transcytosis Target," Sci. Trans. Med., May 2011, 3(84):84ra44.
Zhou et al., "Adeno-associated virus 2-mediated high efficiency gene transfer into immature and mature subsets of hematopoietic progenitor cells in human umbilical cord blood," J. Exp. Med., Jun. 1994, 179(6):1867-1875.
Office Action in Chinese Appln. No. 201980073684.9, mailed on Dec. 14, 2023, 18 pages (with Machine translation).

* cited by examiner

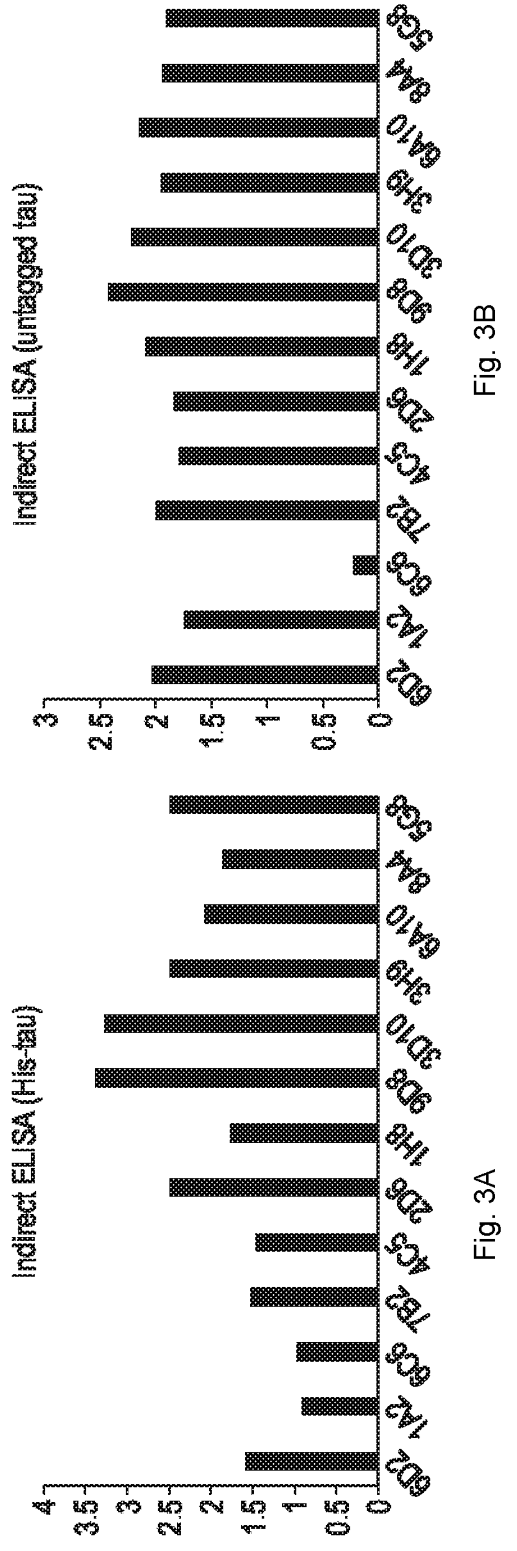
Fig. 3B
Fig. 3A
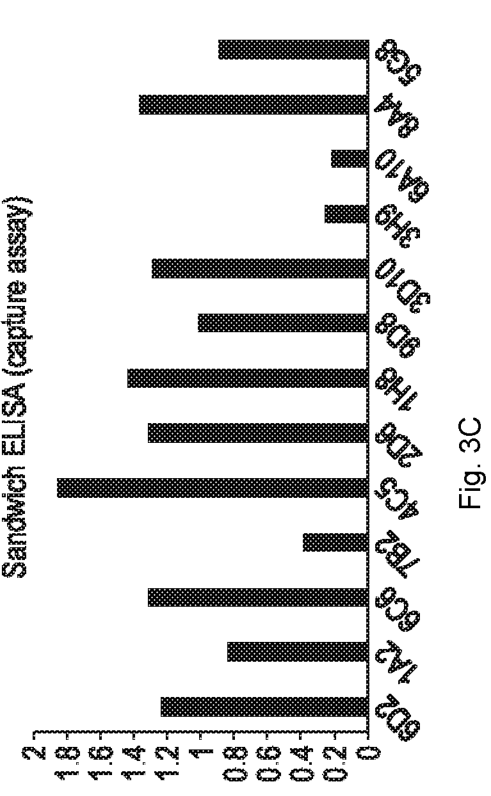
Fig. 3C

| Name | $k_a (M^{-1} s^{-1})$ | $k_d (s^{-1})$ | $k_D$ (nM) |
|---|---|---|---|
| 3D6 | $2.58 \times 10^6$ | $1.19 \times 10^{-3}$ | 0.46 |
| 1H8 | $5.07 \times 10^5$ | $5.61 \times 10^{-3}$ | 11.1 |
| 3H9 | $4.71 \times 10^5$ | $1.41 \times 10^{-3}$ | 3.0 |
| 5G8 | $3.75 \times 10^5$ | $2.54 \times 10^{-3}$ | 6.78 |
| 6D2 | $3.83 \times 10^5$ | $3.18 \times 10^{-3}$ | 8.29 |
| 7G6 | $5.76 \times 10^5$ | $3.32 \times 10^{-3}$ | 5.77 |
| 8A4 | $5.99 \times 10^5$ | $2.27 \times 10^{-3}$ | 3.8 |

SEQUENCE LISTING

<160> NUMBER OF SEQ ID NOS: 106

<210> SEQ ID NO 1
<211> LENGTH: 441
<212> TYPE: PRT
<213> ORGANISM: Homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
```

```
            420                 425                 430

Ser Ala Ser Leu Ala Lys Gln Gly Leu
        435                 440


<210> SEQ ID NO 2
<211> LENGTH: 412
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350
```

```
Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410


<210> SEQ ID NO 3
<211> LENGTH: 383
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320
```

```
Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380


<210> SEQ ID NO 4
<211> LENGTH: 410
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
```

```
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
        355                 360                 365

Ser Gly Asp Thr Ser Pro Arg His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410


<210> SEQ ID NO 5
<211> LENGTH: 381
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270
```

```
Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380


<210> SEQ ID NO 6
<211> LENGTH: 352
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270
```

```
His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350


<210> SEQ ID NO 7
<211> LENGTH: 112
<212> TYPE: PRT
<213> ORGANISM: Artificial sequence
<220> FEATURE:
<223> OTHER INFORMATION: Synthesized

<400> SEQUENCE: 7

Glu Val Gln Leu Gln Gln Ser Gly Ala Asp Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Leu His Trp Val Arg Gln Arg Pro Glu Gln Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Gly Ser Leu Thr Ser Glu Asp Thr Ala Val Tyr Phe Cys
                85                  90                  95

Ser Thr Leu Asp Phe Trp Gly Gln Gly Thr Thr Leu Thr Val Ser Ser
            100                 105                 110


<210> SEQ ID NO 8
<211> LENGTH: 10
<212> TYPE: PRT
<213> ORGANISM: Artificial sequence
<220> FEATURE:
<223> OTHER INFORMATION: Synthesized

<400> SEQUENCE: 8

Gly Phe Asn Ile Lys Asp Tyr Tyr Leu His
1               5                   10


<210> SEQ ID NO 9
<211> LENGTH: 17
<212> TYPE: PRT
<213> ORGANISM: Artificial sequence
<220> FEATURE:
<223> OTHER INFORMATION: Synthesized

<400> SEQUENCE: 9

Trp Ile Asp Pro Glu Asn Gly Asp Thr Val Tyr Asp Pro Lys Phe Gln
1               5                   10                  15

Gly


<210> SEQ ID NO 10

<400> SEQUENCE: 10
```

000

<210> SEQ ID NO 11
<211> LENGTH: 113
<212> TYPE: PRT
<213> ORGANISM: Artificial sequence
<220> FEATURE:
<223> OTHER INFORMATION: Synthesized

<400> SEQUENCE: 11

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg
```

<210> SEQ ID NO 12
<211> LENGTH: 16
<212> TYPE: PRT
<213> ORGANISM: Artificial sequence
<220> FEATURE:
<223> OTHER INFORMATION: Synthesized

<400> SEQUENCE: 12

```
Lys Ser Ser Gln Ser Leu Leu Asp Ser Asp Gly Lys Thr Tyr Leu Asn
1               5                   10                  15
```

<210> SEQ ID NO 13
<211> LENGTH: 7
<212> TYPE: PRT
<213> ORGANISM: Artificial sequence
<220> FEATURE:
<223> OTHER INFORMATION: Synthesized

<400> SEQUENCE: 13

```
Leu Val Ser Lys Leu Asp Ser
1               5
```

<210> SEQ ID NO 14
<211> LENGTH: 9
<212> TYPE: PRT
<213> ORGANISM: Artificial sequence
<220> FEATURE:
<223> OTHER INFORMATION: Synthesized

<400> SEQUENCE: 14

```
Trp Gln Gly Thr His Phe Pro Tyr Thr
1               5
```

<210> SEQ ID NO 15
<211> LENGTH: 112
<212> TYPE: PRT

```
<213> ORGANISM: Artificial sequence
<220> FEATURE:
<223> OTHER INFORMATION: Synthesized

<400> SEQUENCE: 15

Glu Val Gln Leu Val Gln Ser Gly Ala Glu Val Val Arg Pro Gly Ala
1               5                   10                  15

Leu Val Lys Val Ser Cys Lys Ala Ser Gly Phe Asn Ile Lys Asp Tyr
            20                  25                  30

Tyr Leu His Trp Val Arg Gln Ala Pro Glu Gln Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Lys Ala Thr Ile Thr Ala Asp Thr Ser Thr Asn Thr Ala Tyr
65                  70                  75                  80

Leu Gln Leu Ser Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110


<210> SEQ ID NO 16
<211> LENGTH: 112
<212> TYPE: PRT
<213> ORGANISM: Artificial sequence
<220> FEATURE:
<223> OTHER INFORMATION: Synthesized

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Val Ser Gly Phe Asn Ile Lys Asp Tyr
            20                  25                  30

Tyr Leu His Trp Val Arg Gln Ala Pro Glu Gln Gly Leu Glu Trp Met
        35                  40                  45

Gly Trp Ile Asp Pro Glu Asn Gly Asp Thr Val Tyr Asp Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Thr Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 17
<211> LENGTH: 112
<212> TYPE: PRT
<213> ORGANISM: Artificial sequence
<220> FEATURE:
<223> OTHER INFORMATION: Synthesized

<400> SEQUENCE: 17

Glu Val Gln Leu Val Gln Ser Gly Ala Glu Val Val Arg Pro Gly Ala
1               5                   10                  15

Leu Val Lys Ile Ser Cys Lys Ala Ser Gly Phe Asn Ile Lys Asp Tyr
            20                  25                  30

Tyr Leu His Trp Val Arg Gln Arg Pro Glu Gln Gly Leu Glu Trp Ile
        35                  40                  45

Gly Trp Ile Asp Pro Glu Asn Gly Asp Thr Val Tyr Asp Pro Lys Phe
    50                  55                  60
```

Gln Gly Lys Ala Thr Ile Thr Ala Asp Thr Ser Thr Asn Thr Ala Tyr
65 70 75 80

Leu Gln Leu Gly Ser Leu Thr Ser Glu Asp Thr Ala Val Tyr Phe Cys
85 90 95

Ser Thr Leu Asp Phe Trp Gly Gln Gly Thr Leu Val Thr Val Ser Ser
100 105 110

<210> SEQ ID NO 18
<211> LENGTH: 112
<212> TYPE: PRT
<213> ORGANISM: Artificial sequence
<220> FEATURE:
<223> OTHER INFORMATION: Synthesized

<400> SEQUENCE: 18

Glu Val Gln Leu Val Gln Ser Gly Ala Glu Val Val Lys Pro Gly Ala
1 5 10 15

Thr Val Lys Ile Ser Cys Lys Ala Ser Gly Phe Asn Ile Lys Asp Tyr
20 25 30

Tyr Leu His Trp Val Arg Gln Arg Pro Gly Gln Gly Leu Glu Trp Ile
35 40 45

Gly Trp Ile Asp Pro Glu Asn Gly Asp Thr Val Tyr Asp Pro Lys Phe
50 55 60

Gln Gly Arg Ala Thr Ile Thr Ala Asp Thr Ser Thr Asp Thr Ala Tyr
65 70 75 80

Leu Gln Leu Gly Ser Leu Thr Ser Glu Asp Thr Ala Val Tyr Phe Cys
85 90 95

Ser Thr Leu Asp Phe Trp Gly Gln Gly Thr Leu Val Thr Val Ser Ser
100 105 110

<210> SEQ ID NO 19
<211> LENGTH: 112
<212> TYPE: PRT
<213> ORGANISM: Artificial sequence
<220> FEATURE:
<223> OTHER INFORMATION: Synthesized

<400> SEQUENCE: 19

Glu Val Gln Leu Val Gln Ser Gly Ala Glu Val Val Lys Pro Gly Ala
1 5 10 15

Thr Val Lys Ile Ser Cys Lys Ala Ser Gly Phe Thr Ile Lys Asp Tyr
20 25 30

Tyr Leu His Trp Val Arg Gln Arg Pro Gly Gln Gly Leu Glu Trp Ile
35 40 45

Gly Trp Ile Asp Pro Glu Asp Gly Asp Thr Val Tyr Ala Pro Lys Phe
50 55 60

Gln Gly Arg Ala Thr Ile Thr Ala Asp Thr Ser Thr Asp Thr Ala Tyr
65 70 75 80

Leu Gln Leu Gly Ser Leu Thr Ser Glu Asp Thr Ala Val Tyr Phe Cys
85 90 95

Ser Thr Leu Asp Phe Trp Gly Gln Gly Thr Leu Val Thr Val Ser Ser
100 105 110

<210> SEQ ID NO 20
<211> LENGTH: 113
<212> TYPE: PRT
<213> ORGANISM: Artificial sequence
<220> FEATURE:
<223> OTHER INFORMATION: Synthesized

<400> SEQUENCE: 20

```
Asp Val Val Met Thr Gln Ser Pro Leu Ser Leu Ser Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg
```

<210> SEQ ID NO 21
<211> LENGTH: 113
<212> TYPE: PRT
<213> ORGANISM: Artificial sequence
<220> FEATURE:
<223> OTHER INFORMATION: Synthesized

<400> SEQUENCE: 21

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg
```

<210> SEQ ID NO 22
<211> LENGTH: 113
<212> TYPE: PRT
<213> ORGANISM: Artificial sequence
<220> FEATURE:
<223> OTHER INFORMATION: Synthesized

<400> SEQUENCE: 22

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
```

```
    50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg


<210> SEQ ID NO 23
<211> LENGTH: 113
<212> TYPE: PRT
<213> ORGANISM: Artificial sequence
<220> FEATURE:
<223> OTHER INFORMATION: Synthesized

<400> SEQUENCE: 23

Asp Ile Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg


<210> SEQ ID NO 24
<211> LENGTH: 119
<212> TYPE: PRT
<213> ORGANISM: Homo sapiens

<400> SEQUENCE: 24

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Lys Gly Glu Phe Glu Gly Met Asp Val Trp Gly Gln Gly
            100                 105                 110

Thr Thr Val Thr Val Ser Ser
        115
```

```
<210> SEQ ID NO 25
<211> LENGTH: 98
<212> TYPE: PRT
<213> ORGANISM: Homo sapiens

<400> SEQUENCE: 25

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr


<210> SEQ ID NO 26
<211> LENGTH: 13
<212> TYPE: PRT
<213> ORGANISM: Homo sapiens

<400> SEQUENCE: 26

Gln His Trp Gly Gln Gly Thr Leu Val Thr Val Ser Ser
1               5                   10


<210> SEQ ID NO 27
<211> LENGTH: 100
<212> TYPE: PRT
<213> ORGANISM: Homo sapiens

<400> SEQUENCE: 27

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100


<210> SEQ ID NO 28
<211> LENGTH: 12
<212> TYPE: PRT
<213> ORGANISM: Homo sapiens

<400> SEQUENCE: 28

Tyr Thr Phe Gly Gln Gly Thr Lys Leu Glu Ile Lys
1               5                   10
```

<210> SEQ ID NO 29
<211> LENGTH: 112
<212> TYPE: PRT
<213> ORGANISM: Homo sapiens

<400> SEQUENCE: 29

Asp Val Val Met Thr Gln Ser Pro Leu Ser Leu Thr Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Arg Val Ser His Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Tyr Trp Pro Leu Thr Phe Gly Gln Gly Thr Lys Leu Glu Ile Lys
            100                 105                 110

<210> SEQ ID NO 30
<211> LENGTH: 336
<212> TYPE: DNA
<213> ORGANISM: Artificial sequence
<220> FEATURE:
<223> OTHER INFORMATION: Synthesized

<400> SEQUENCE: 30
gaggttcagc tgcagcagtc tggggctgac cttgtgaggc caggggcctt agtcaagttg     60
tcctgcaaag cttctggctt caacattaaa gactactatt tgcactgggt gaggcagagg    120
cctgaacagg gcctggagtg gattggatgg attgatcctg agaatggtga tactgtatat    180
gacccgaagt tccagggcaa ggccactata acagcagaca catcctccaa tacagcctac    240
ctgcagctcg gcagcctgac atctgaggac actgccgtct atttctgttc tacccttgac    300
ttctggggcc aaggcaccac tctcacagtc tcctca                              336

<210> SEQ ID NO 31
<211> LENGTH: 339
<212> TYPE: DNA
<213> ORGANISM: Artificial sequence
<220> FEATURE:
<223> OTHER INFORMATION: Synthesized

<400> SEQUENCE: 31
gatgttgtga tgacccagac tccactcact ttgtcggtta ccattggaca accagcctcc     60
atctcttgca agtcaagtca gagcctctta gatagtgatg gaaagacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttccg    300
tacacgttcg gaggggggac caagctggaa ataaaacgt                           339

<210> SEQ ID NO 32
<211> LENGTH: 5
<212> TYPE: PRT
<213> ORGANISM: Artificial sequence
<220> FEATURE:
<223> OTHER INFORMATION: Synthesized

<400> SEQUENCE: 32

Asp Tyr Tyr Leu His
1 5

<210> SEQ ID NO 33
<211> LENGTH: 7
<212> TYPE: PRT
<213> ORGANISM: Artificial sequence
<220> FEATURE:
<223> OTHER INFORMATION: Synthesized

<400> SEQUENCE: 33

Gly Phe Asn Ile Lys Asp Tyr
1 5

<210> SEQ ID NO 34
<211> LENGTH: 6
<212> TYPE: PRT
<213> ORGANISM: Artificial sequence
<220> FEATURE:
<223> OTHER INFORMATION: Synthesized

<400> SEQUENCE: 34

Asp Pro Glu Asn Gly Asp
1 5

<210> SEQ ID NO 35
<211> LENGTH: 10
<212> TYPE: PRT
<213> ORGANISM: Artificial sequence
<220> FEATURE:
<223> OTHER INFORMATION: Synthesized

<400> SEQUENCE: 35

Trp Ile Asp Pro Glu Asn Gly Asp Thr Val
1 5 10

<210> SEQ ID NO 36
<211> LENGTH: 7
<212> TYPE: PRT
<213> ORGANISM: Artificial sequence
<220> FEATURE:
<223> OTHER INFORMATION: Synthesized

<400> SEQUENCE: 36

Lys Thr Tyr Leu Asn Trp Leu
1 5

<210> SEQ ID NO 37
<211> LENGTH: 10
<212> TYPE: PRT
<213> ORGANISM: Artificial sequence
<220> FEATURE:
<223> OTHER INFORMATION: Synthesized

<400> SEQUENCE: 37

Arg Leu Ile Tyr Leu Val Ser Lys Leu Asp
1 5 10

<210> SEQ ID NO 38
<211> LENGTH: 8
<212> TYPE: PRT
<213> ORGANISM: Artificial sequence
<220> FEATURE:
<223> OTHER INFORMATION: Synthesized

<400> SEQUENCE: 38

Trp Gln Gly Thr His Phe Pro Tyr
1               5

<210> SEQ ID NO 39
<211> LENGTH: 6
<212> TYPE: PRT
<213> ORGANISM: Artificial sequence
<220> FEATURE:
<223> OTHER INFORMATION: Synthesized

<400> SEQUENCE: 39

Lys Asp Tyr Tyr Leu His
1               5

<210> SEQ ID NO 40
<211> LENGTH: 13
<212> TYPE: PRT
<213> ORGANISM: Artificial sequence
<220> FEATURE:
<223> OTHER INFORMATION: Synthesized

<400> SEQUENCE: 40

Trp Ile Gly Trp Ile Asp Pro Glu Asn Gly Asp Thr Val
1               5                   10

<210> SEQ ID NO 41
<211> LENGTH: 4
<212> TYPE: PRT
<213> ORGANISM: Artificial sequence
<220> FEATURE:
<223> OTHER INFORMATION: Synthesized

<400> SEQUENCE: 41

Ser Thr Leu Asp
1

<210> SEQ ID NO 42
<211> LENGTH: 10
<212> TYPE: PRT
<213> ORGANISM: Artificial sequence
<220> FEATURE:
<223> OTHER INFORMATION: Synthesized

<400> SEQUENCE: 42

Gly Phe Thr Ile Lys Asp Tyr Tyr Leu His
1               5                   10

<210> SEQ ID NO 43
<211> LENGTH: 17
<212> TYPE: PRT
<213> ORGANISM: Artificial sequence
<220> FEATURE:
<223> OTHER INFORMATION: Synthesized

<400> SEQUENCE: 43

Trp Ile Asp Pro Glu Asp Gly Asp Thr Val Tyr Ala Pro Lys Phe Gln
1               5                   10                  15

Gly

<210> SEQ ID NO 44
<211> LENGTH: 112
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (13)..(13)
<223> OTHER INFORMATION: Xaa = Arg or Lys
<220> FEATURE:
<221> NAME/KEY: MISC_FEATURE
<222> LOCATION: (67)..(67)
<223> OTHER INFORMATION: Xaa = Lys or Arg

<400> SEQUENCE: 44

```
Glu Val Gln Leu Val Gln Ser Gly Ala Glu Val Val Xaa Pro Gly Ala
1               5                   10                  15

Leu Val Lys Ile Ser Cys Lys Ala Ser Gly Phe Asn Ile Lys Asp Tyr
            20                  25                  30

Tyr Leu His Trp Val Arg Gln Arg Pro Glu Gln Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Xaa Ala Thr Ile Thr Ala Asp Thr Ser Thr Asn Thr Ala Tyr
65                  70                  75                  80

Leu Gln Leu Gly Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110
```

<210> SEQ ID NO 45
<211> LENGTH: 113
<212> TYPE: PRT
<213> ORGANISM: Artificial sequence
<220> FEATURE:
<223> OTHER INFORMATION: Synthesized

<400> SEQUENCE: 45

```
Asp Val Val Met Thr Gln Ser Pro Leu Ser Leu Ser Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg
```

<210> SEQ ID NO 46
<211> LENGTH: 112
<212> TYPE: PRT
<213> ORGANISM: Artificial sequence
<220> FEATURE:
<223> OTHER INFORMATION: Synthesized

<400> SEQUENCE: 46

```
Glu Val Gln Leu Val Gln Ser Gly Ala Glu Val Val Lys Pro Gly Ala
1               5                   10                  15

Thr Val Lys Ile Ser Cys Lys Ala Ser Gly Phe Thr Ile Lys Asp Tyr
```

```
            20                  25                  30

Tyr Leu His Trp Val Arg Gln Arg Pro Gly Lys Gly Leu Glu Trp Ile
        35                  40                  45

Gly Trp Val Asp Pro Glu Asp Gly Asp Thr Val Tyr Ala Pro Lys Phe
    50                  55                  60

Gln Gly Arg Ala Thr Ile Thr Ala Asp Thr Ser Thr Asp Thr Ala Tyr
65                  70                  75                  80

Leu Glu Leu Gly Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110


<210> SEQ ID NO 47
<211> LENGTH: 112
<212> TYPE: PRT
<213> ORGANISM: Artificial sequence
<220> FEATURE:
<223> OTHER INFORMATION: Synthesized

<400> SEQUENCE: 47

Glu Val Gln Leu Val Gln Ser Gly Ala Glu Val Val Lys Pro Gly Ala
1               5                   10                  15

Thr Val Lys Ile Ser Cys Lys Ala Ser Gly Phe Thr Ile Lys Asp Tyr
            20                  25                  30

Tyr Leu His Trp Val Arg Gln Arg Pro Gly Lys Gly Leu Glu Trp Ile
        35                  40                  45

Gly Trp Ile Asp Pro Glu Asp Gly Asp Thr Val Tyr Ala Pro Lys Phe
    50                  55                  60

Gln Gly Arg Ala Thr Ile Thr Ala Asp Thr Ser Thr Asp Thr Ala Tyr
65                  70                  75                  80

Leu Glu Leu Gly Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110


<210> SEQ ID NO 48
<211> LENGTH: 112
<212> TYPE: PRT
<213> ORGANISM: Artificial sequence
<220> FEATURE:
<223> OTHER INFORMATION: Synthesized

<400> SEQUENCE: 48

Glu Val Gln Leu Val Gln Ser Gly Ala Glu Val Lys Arg Pro Gly Ala
1               5                   10                  15

Leu Val Lys Ile Ser Cys Lys Ala Ser Gly Phe Asn Phe Lys Asp Tyr
            20                  25                  30

Tyr Leu His Trp Val Arg Gln Arg Pro Glu Gln Gly Leu Glu Trp Met
        35                  40                  45

Gly Trp Ile Asp Pro Glu Asn Gly Asp Thr Val Tyr Asp Glu Lys Phe
    50                  55                  60

Gln Gly Arg Val Thr Ile Thr Ala Asp Thr Ser Thr Asn Thr Ala Tyr
65                  70                  75                  80

Leu Gln Leu Gly Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110
```

```
<210> SEQ ID NO 49
<211> LENGTH: 112
<212> TYPE: PRT
<213> ORGANISM: Artificial sequence
<220> FEATURE:
<223> OTHER INFORMATION: Synthesized

<400> SEQUENCE: 49

Glu Val Gln Leu Val Gln Ser Gly Ala Glu Val Lys Arg Pro Gly Ala
1               5                   10                  15

Leu Val Lys Ile Ser Cys Lys Ala Ser Gly Tyr Thr Phe Thr Asp Tyr
            20                  25                  30

Tyr Leu His Trp Val Arg Gln Arg Pro Glu Gln Gly Leu Glu Trp Met
        35                  40                  45

Gly Trp Val Asp Pro Glu Asp Gly Asp Thr Val Tyr Ala Glu Lys Phe
    50                  55                  60

Gln Gly Arg Val Thr Ile Thr Ala Asp Thr Ser Thr Asn Thr Ala Tyr
65                  70                  75                  80

Leu Gln Leu Gly Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110


<210> SEQ ID NO 50
<211> LENGTH: 112
<212> TYPE: PRT
<213> ORGANISM: Artificial sequence
<220> FEATURE:
<223> OTHER INFORMATION: Synthesized

<400> SEQUENCE: 50

Glu Val Gln Leu Val Gln Ser Gly Ala Asp Val Val Lys Pro Gly Ala
1               5                   10                  15

Leu Val Lys Ile Ser Cys Lys Ala Ser Gly Phe Thr Ile Lys Asp Tyr
            20                  25                  30

Tyr Leu His Trp Val Arg Gln Arg Pro Glu Gln Gly Leu Glu Trp Ile
        35                  40                  45

Gly Trp Ile Asp Pro Glu Asn Gly Asp Thr Val Tyr Ala Glu Lys Phe
    50                  55                  60

Gln Gly Arg Val Thr Ile Thr Ala Asp Thr Ser Thr Asn Thr Ala Tyr
65                  70                  75                  80

Leu Glu Leu Gly Ser Leu Thr Ser Glu Asp Thr Ala Val Tyr Phe Cys
                85                  90                  95

Ser Thr Leu Asp Phe Trp Gly Gln Gly Thr Thr Leu Thr Val Ser Ser
            100                 105                 110


<210> SEQ ID NO 51
<211> LENGTH: 112
<212> TYPE: PRT
<213> ORGANISM: Artificial sequence
<220> FEATURE:
<223> OTHER INFORMATION: Synthesized

<400> SEQUENCE: 51

Glu Val Gln Leu Val Gln Ser Gly Ala Asp Val Val Lys Pro Gly Ala
1               5                   10                  15

Leu Val Lys Ile Ser Cys Lys Ala Ser Gly Phe Thr Ile Lys Asp Tyr
            20                  25                  30

Tyr Leu His Trp Val Arg Gln Arg Pro Gly Gln Gly Leu Glu Trp Ile
```

```
        35                  40                  45

Gly Trp Val Asp Pro Glu Asp Gly Asp Thr Val Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Gly Ser Leu Thr Ser Glu Asp Thr Ala Val Tyr Phe Cys
                85                  90                  95

Ser Thr Leu Asp Tyr Trp Gly Gln Gly Thr Thr Leu Thr Val Ser Ser
            100                 105                 110


<210> SEQ ID NO 52
<211> LENGTH: 112
<212> TYPE: PRT
<213> ORGANISM: Artificial sequence
<220> FEATURE:
<223> OTHER INFORMATION: Synthesized

<400> SEQUENCE: 52

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
            20                  25                  30

Tyr Leu His Trp Val Arg Gln Ala Pro Gly Lys Gly Leu Glu Trp Met
        35                  40                  45

Gly Trp Ile Asp Pro Glu Asn Gly Asp Thr Val Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 53
<211> LENGTH: 112
<212> TYPE: PRT
<213> ORGANISM: Artificial sequence
<220> FEATURE:
<223> OTHER INFORMATION: Synthesized

<400> SEQUENCE: 53

Glu Val Gln Leu Val Gln Ser Gly Ala Glu Val Lys Lys Pro Gly Ala
1               5                   10                  15

Leu Val Lys Ile Ser Cys Lys Val Ser Gly Tyr Asn Phe Lys Asp Tyr
            20                  25                  30

Tyr Leu His Trp Val Arg Gln Ala Pro Gly Lys Gly Leu Glu Trp Met
        35                  40                  45

Gly Trp Ile Asp Pro Glu Asn Gly Asp Thr Val Tyr Asp Glu Lys Phe
    50                  55                  60

Gln Gly Arg Val Thr Ile Thr Ala Asp Thr Ser Thr Asn Thr Ala Tyr
65                  70                  75                  80

Met Glu Leu Gly Ser Leu Arg Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 54
<211> LENGTH: 112
```

```
<212> TYPE: PRT
<213> ORGANISM: Artificial sequence
<220> FEATURE:
<223> OTHER INFORMATION: Synthesized

<400> SEQUENCE: 54

Glu Val Gln Leu Val Gln Ser Gly Ala Glu Val Lys Lys Pro Gly Ala
1               5                   10                  15

Leu Val Lys Ile Ser Cys Lys Val Ser Gly Tyr Thr Phe Thr Asp Tyr
            20                  25                  30

Tyr Leu His Trp Val Arg Gln Ala Pro Gly Lys Gly Leu Glu Trp Met
        35                  40                  45

Gly Trp Val Asp Pro Glu Asp Gly Asp Thr Val Tyr Ala Glu Lys Phe
    50                  55                  60

Gln Gly Arg Val Thr Ile Thr Ala Asp Thr Ser Thr Asn Thr Ala Tyr
65                  70                  75                  80

Met Glu Leu Gly Ser Leu Arg Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 55
<211> LENGTH: 112
<212> TYPE: PRT
<213> ORGANISM: Artificial sequence
<220> FEATURE:
<223> OTHER INFORMATION: Synthesized

<400> SEQUENCE: 55

Glu Val Gln Leu Val Gln Ser Gly Ala Glu Val Val Lys Pro Gly Ala
1               5                   10                  15

Thr Val Lys Ile Ser Cys Lys Val Ser Gly Phe Asn Ile Lys Asp Tyr
            20                  25                  30

Tyr Leu His Trp Val Arg Gln Arg Pro Gly Lys Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Lys Ala Thr Ile Thr Ala Asp Thr Ser Thr Asn Thr Ala Tyr
65                  70                  75                  80

Leu Glu Leu Gly Ser Leu Thr Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 56
<211> LENGTH: 112
<212> TYPE: PRT
<213> ORGANISM: Artificial sequence
<220> FEATURE:
<223> OTHER INFORMATION: Synthesized

<400> SEQUENCE: 56

Glu Val Gln Leu Val Gln Ser Gly Ala Glu Val Val Lys Pro Gly Ala
1               5                   10                  15

Leu Val Lys Ile Ser Cys Lys Val Ser Gly Tyr Asn Phe Lys Asp Tyr
            20                  25                  30

Tyr Leu His Trp Val Arg Gln Arg Pro Gly Lys Gly Leu Glu Trp Met
        35                  40                  45

Gly Trp Ile Asp Pro Glu Asn Gly Asp Thr Val Tyr Asp Glu Lys Phe
```

```
    50                  55                  60

Gln Gly Arg Val Thr Ile Thr Ala Asp Thr Ser Thr Asp Thr Ala Tyr
65                  70                  75                  80

Leu Glu Leu Gly Ser Leu Thr Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 57
<211> LENGTH: 112
<212> TYPE: PRT
<213> ORGANISM: Artificial sequence
<220> FEATURE:
<223> OTHER INFORMATION: Synthesized

<400> SEQUENCE: 57

Glu Val Gln Leu Val Gln Ser Gly Ala Glu Val Val Lys Pro Gly Ala
1               5                   10                  15

Leu Val Lys Ile Ser Cys Lys Val Ser Gly Tyr Thr Phe Thr Asp Tyr
            20                  25                  30

Tyr Leu His Trp Val Arg Gln Arg Pro Gly Lys Gly Leu Glu Trp Met
        35                  40                  45

Gly Trp Val Asp Pro Glu Asp Gly Asp Thr Val Tyr Ala Glu Lys Phe
    50                  55                  60

Gln Gly Arg Val Thr Ile Thr Ala Asp Thr Ser Thr Asp Thr Ala Tyr
65                  70                  75                  80

Leu Glu Leu Gly Ser Leu Thr Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 58
<211> LENGTH: 10
<212> TYPE: PRT
<213> ORGANISM: Artificial sequence
<220> FEATURE:
<223> OTHER INFORMATION: Synthesized

<400> SEQUENCE: 58

Gly Phe Asn Phe Lys Asp Tyr Tyr Leu His
1               5                   10


<210> SEQ ID NO 59
<211> LENGTH: 10
<212> TYPE: PRT
<213> ORGANISM: Artificial sequence
<220> FEATURE:
<223> OTHER INFORMATION: Synthesized

<400> SEQUENCE: 59

Gly Tyr Thr Phe Thr Asp Tyr Tyr Leu His
1               5                   10


<210> SEQ ID NO 60
<211> LENGTH: 10
<212> TYPE: PRT
<213> ORGANISM: Artificial sequence
<220> FEATURE:
<223> OTHER INFORMATION: Synthesized

<400> SEQUENCE: 60

Gly Tyr Asn Phe Lys Asp Tyr Tyr Leu His
```

1 5 10

<210> SEQ ID NO 61
<211> LENGTH: 17
<212> TYPE: PRT
<213> ORGANISM: Artificial sequence
<220> FEATURE:
<223> OTHER INFORMATION: Synthesized

<400> SEQUENCE: 61

Trp Val Asp Pro Glu Asp Gly Asp Thr Val Tyr Ala Pro Lys Phe Gln
1 5 10 15

Gly

<210> SEQ ID NO 62
<211> LENGTH: 17
<212> TYPE: PRT
<213> ORGANISM: Artificial sequence
<220> FEATURE:
<223> OTHER INFORMATION: Synthesized

<400> SEQUENCE: 62

Trp Ile Asp Pro Glu Asn Gly Asp Thr Val Tyr Asp Glu Lys Phe Gln
1 5 10 15

Gly

<210> SEQ ID NO 63
<211> LENGTH: 17
<212> TYPE: PRT
<213> ORGANISM: Artificial sequence
<220> FEATURE:
<223> OTHER INFORMATION: Synthesized

<400> SEQUENCE: 63

Trp Val Asp Pro Glu Asp Gly Asp Thr Val Tyr Ala Glu Lys Phe Gln
1 5 10 15

Gly

<210> SEQ ID NO 64
<211> LENGTH: 17
<212> TYPE: PRT
<213> ORGANISM: Artificial sequence
<220> FEATURE:
<223> OTHER INFORMATION: Synthesized

<400> SEQUENCE: 64

Trp Ile Asp Pro Glu Asn Gly Asp Thr Val Tyr Ala Glu Lys Phe Gln
1 5 10 15

Gly

<210> SEQ ID NO 65

<400> SEQUENCE: 65

000

<210> SEQ ID NO 66
<211> LENGTH: 112
<212> TYPE: PRT
<213> ORGANISM: Artificial sequence
<220> FEATURE:
<223> OTHER INFORMATION: Synthesized

<400> SEQUENCE: 66

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Leu Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Asp Asp Thr Glu Tyr Ala Pro Lys Phe
    50                  55                  60

Gln Gly Arg Ala Thr Leu Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Pro Leu Asp Tyr Trp Gly Gln Gly Thr Ser Val Thr Val Ser Ser
            100                 105                 110


<210> SEQ ID NO 67
<211> LENGTH: 10
<212> TYPE: PRT
<213> ORGANISM: Artificial sequence
<220> FEATURE:
<223> OTHER INFORMATION: Synthesized

<400> SEQUENCE: 67

Gly Leu Asn Ile Lys Asp Tyr Tyr Ile His
1               5                   10


<210> SEQ ID NO 68
<211> LENGTH: 17
<212> TYPE: PRT
<213> ORGANISM: Artificial sequence
<220> FEATURE:
<223> OTHER INFORMATION: Synthesized

<400> SEQUENCE: 68

Trp Ile Asp Pro Glu Asn Asp Asp Thr Glu Tyr Ala Pro Lys Phe Gln
1               5                   10                  15

Gly


<210> SEQ ID NO 69

<400> SEQUENCE: 69

000


<210> SEQ ID NO 70
<211> LENGTH: 114
<212> TYPE: PRT
<213> ORGANISM: Mus musculus

<400> SEQUENCE: 70

Lys Val Lys Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile Gln Trp Val Lys Gln Arg Pro Glu Gln Gly Leu Glu Trp Ile
        35                  40                  45

Gly Trp Ile Asp Pro Glu Asn Gly Asn Ser Glu Tyr Ala Pro Arg Phe
    50                  55                  60

Gln Gly Lys Ala Thr Met Thr Ala Asp Thr Leu Ser Asn Thr Ala Tyr
65                  70                  75                  80
```

```
Leu Gln Leu Ser Ser Leu Thr Ser Glu Asp Thr Ala Val Tyr Tyr Cys
            85                  90                  95

Asn Ala Asp Leu His Asp Tyr Trp Gly Gln Gly Thr Thr Leu Thr Val
            100                 105                 110

Ser Ser


<210> SEQ ID NO 71
<211> LENGTH: 112
<212> TYPE: PRT
<213> ORGANISM: Artificial sequence
<220> FEATURE:
<223> OTHER INFORMATION: Synthesized

<400> SEQUENCE: 71

Glu Val Gln Leu Val Gln Ser Gly Ala Glu Val Val Lys Pro Gly Ala
1               5                   10                  15

Leu Val Lys Ile Ser Cys Lys Ala Ser Gly Phe Asn Ile Lys Asp Tyr
            20                  25                  30

Tyr Leu His Trp Val Arg Gln Arg Pro Gly Gln Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Arg Val Thr Ile Thr Ala Asp Thr Ser Thr Asn Thr Ala Tyr
65                  70                  75                  80

Leu Glu Leu Gly Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110


<210> SEQ ID NO 72
<211> LENGTH: 442
<212> TYPE: PRT
<213> ORGANISM: Artificial sequence
<220> FEATURE:
<223> OTHER INFORMATION: Synthesized

<400> SEQUENCE: 72

Glu Val Gln Leu Gln Gln Ser Gly Ala Asp Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Leu His Trp Val Arg Gln Arg Pro Glu Gln Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Gly Ser Leu Thr Ser Glu Asp Thr Ala Val Tyr Phe Cys
                85                  90                  95

Ser Thr Leu Asp Phe Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160
```

```
Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 73
<211> LENGTH: 219
<212> TYPE: PRT
<213> ORGANISM: Artificial sequence
<220> FEATURE:
<223> OTHER INFORMATION: Synthesized

<400> SEQUENCE: 73

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80
```

```
Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 74
<211> LENGTH: 115
<212> TYPE: PRT
<213> ORGANISM: Homo sapiens

<400> SEQUENCE: 74

Glu Val Gln Leu Gln Gln Ser Gly Ala Glu Leu Val Arg Pro Gly Ser
1               5                   10                  15

Ser Val Lys Ile Ser Cys Lys Ala Ser Gly Tyr Ile Phe Asn Asn Tyr
            20                  25                  30

Trp Ile Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Gly Tyr Ile Val Tyr Trp Gly Gln Gly Thr Leu Val Thr
            100                 105                 110

Val Ser Ala
        115


<210> SEQ ID NO 75
<211> LENGTH: 114
<212> TYPE: PRT
<213> ORGANISM: Homo sapiens

<400> SEQUENCE: 75

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60
```

```
Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Tyr Tyr Gly Ile Tyr Trp Gly Gln Gly Thr Thr Leu Thr Val
            100                 105                 110

Ser Ser


<210> SEQ ID NO 76
<211> LENGTH: 112
<212> TYPE: PRT
<213> ORGANISM: Artificial sequence
<220> FEATURE:
<223> OTHER INFORMATION: Synthesized

<400> SEQUENCE: 76

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Ser Thr Leu Asp Phe Trp Gly Gln Gly Thr Thr Leu Thr Val Ser Ser
            100                 105                 110


<210> SEQ ID NO 77
<211> LENGTH: 112
<212> TYPE: PRT
<213> ORGANISM: Artificial sequence
<220> FEATURE:
<223> OTHER INFORMATION: Synthesized

<400> SEQUENCE: 77

Glu Val Gln Leu Val Gln Ser Gly Ala Glu Val Val Lys Pro Gly Ala
1               5                   10                  15

Ser Val Lys Ile Ser Cys Lys Ala Ser Gly Phe Asn Ile Lys Asp Tyr
            20                  25                  30

Tyr Leu His Trp Val Arg Gln Arg Pro Gly Lys Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Arg Ala Thr Ile Thr Ala Asp Thr Ser Thr Asp Thr Ala Tyr
65                  70                  75                  80

Leu Glu Leu Ser Ser Leu Thr Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110


<210> SEQ ID NO 78
<211> LENGTH: 112
<212> TYPE: PRT
<213> ORGANISM: Artificial sequence
<220> FEATURE:
```

<223> OTHER INFORMATION: Synthesized

<400> SEQUENCE: 78

```
Glu Val Gln Leu Val Gln Ser Gly Ala Glu Val Val Lys Pro Gly Ala
1               5                   10                  15

Thr Val Lys Ile Ser Cys Lys Ala Ser Gly Phe Asn Ile Lys Asp Tyr
            20                  25                  30

Tyr Leu His Trp Val Arg Gln Arg Pro Gly Lys Gly Leu Glu Trp Ile
        35                  40                  45

Gly Trp Ile Asp Pro Glu Asn Gly Asp Thr Ile Tyr Asp Pro Lys Phe
    50                  55                  60

Gln Gly Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110
```

<210> SEQ ID NO 79
<211> LENGTH: 112
<212> TYPE: PRT
<213> ORGANISM: Artificial sequence
<220> FEATURE:
<223> OTHER INFORMATION: Synthesized

<400> SEQUENCE: 79

```
Glu Val Gln Leu Val Gln Ser Gly Ala Glu Val Val Lys Pro Gly Ala
1               5                   10                  15

Thr Val Lys Ile Ser Cys Lys Ala Ser Gly Phe Thr Ile Lys Asp Tyr
            20                  25                  30

Tyr Leu His Trp Val Arg Gln Arg Pro Gly Lys Gly Leu Glu Trp Ile
        35                  40                  45

Gly Trp Ile Asp Pro Glu Asn Gly Asp Thr Ile Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110
```

<210> SEQ ID NO 80
<211> LENGTH: 112
<212> TYPE: PRT
<213> ORGANISM: Artificial sequence
<220> FEATURE:
<223> OTHER INFORMATION: Synthesized

<400> SEQUENCE: 80

```
Glu Val Gln Leu Val Gln Ser Gly Ala Glu Val Val Lys Pro Gly Ala
1               5                   10                  15

Thr Val Lys Ile Ser Cys Lys Ala Ser Gly Phe Thr Ile Lys Asp Tyr
            20                  25                  30

Tyr Leu His Trp Val Arg Gln Arg Pro Gly Lys Gly Leu Glu Trp Ile
        35                  40                  45

Gly Trp Ile Asp Pro Glu Asp Gly Glu Thr Ile Tyr Asp Pro Lys Phe
    50                  55                  60

Gln Gly Arg Val Thr Ile Thr Ala Asp Thr Ser Thr Asp Thr Ala Tyr
```

```
65                  70                  75                  80

Met Glu Leu Ser Ser Leu Arg Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 81
<211> LENGTH: 112
<212> TYPE: PRT
<213> ORGANISM: Homo sapiens

<400> SEQUENCE: 81

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Val Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Ser Gly Thr Lys Leu Glu Ile Lys
            100                 105                 110


<210> SEQ ID NO 82
<211> LENGTH: 112
<212> TYPE: PRT
<213> ORGANISM: Homo sapiens

<400> SEQUENCE: 82

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val His Tyr Cys Glu Gln Gly
                85                  90                  95

Thr His Phe Pro Leu Thr Phe Gly Ala Gly Thr Lys Leu Glu Leu Lys
            100                 105                 110


<210> SEQ ID NO 83
<211> LENGTH: 113
<212> TYPE: PRT
<213> ORGANISM: Artificial sequence
<220> FEATURE:
<223> OTHER INFORMATION: Synthesized

<400> SEQUENCE: 83

Asp Val Val Met Thr Gln Thr Pro Leu Thr Leu Ser Val Thr Ile Gly
1               5                   10                  15
```

```
Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val His Tyr Cys Trp Gln Gly
                85                  90                  95

Thr His Phe Pro Tyr Thr Phe Gly Ala Gly Thr Lys Leu Glu Leu Lys
            100                 105                 110

Arg


<210> SEQ ID NO 84
<211> LENGTH: 113
<212> TYPE: PRT
<213> ORGANISM: Artificial sequence
<220> FEATURE:
<223> OTHER INFORMATION: Synthesized

<400> SEQUENCE: 84

Asp Val Val Met Thr Gln Ser Pro Leu Ser Leu Ser Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Ala Gly Thr Lys Leu Glu Ile Lys
            100                 105                 110

Arg


<210> SEQ ID NO 85
<211> LENGTH: 113
<212> TYPE: PRT
<213> ORGANISM: Artificial sequence
<220> FEATURE:
<223> OTHER INFORMATION: Synthesized

<400> SEQUENCE: 85

Asp Val Val Met Thr Gln Ser Pro Leu Ser Leu Ser Val Thr Leu Gly
1               5                   10                  15

Glu Pro Ala Ser Ile Ser Cys Arg Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
```

```
                85                  90                  95

Thr His Phe Pro Tyr Thr Phe Gly Gln Gly Thr Lys Leu Glu Ile Lys
            100                 105                 110

Arg


<210> SEQ ID NO 86
<211> LENGTH: 10
<212> TYPE: PRT
<213> ORGANISM: Artificial sequence
<220> FEATURE:
<223> OTHER INFORMATION: Synthesized

<400> SEQUENCE: 86

Gly Phe Thr Ile Lys Asp Tyr Tyr Leu His
1               5                   10


<210> SEQ ID NO 87
<211> LENGTH: 17
<212> TYPE: PRT
<213> ORGANISM: Artificial sequence
<220> FEATURE:
<223> OTHER INFORMATION: Synthesized

<400> SEQUENCE: 87

Trp Ile Asp Pro Glu Asn Gly Asp Thr Ile Tyr Asp Pro Lys Phe Gln
1               5                   10                  15

Gly


<210> SEQ ID NO 88
<211> LENGTH: 17
<212> TYPE: PRT
<213> ORGANISM: Artificial sequence
<220> FEATURE:
<223> OTHER INFORMATION: Synthesized

<400> SEQUENCE: 88

Trp Ile Asp Pro Glu Asp Gly Glu Thr Ile Tyr Asp Pro Lys Phe Gln
1               5                   10                  15

Gly


<210> SEQ ID NO 89
<211> LENGTH: 16
<212> TYPE: PRT
<213> ORGANISM: Artificial sequence
<220> FEATURE:
<223> OTHER INFORMATION: Synthesized

<400> SEQUENCE: 89

Arg Ser Ser Gln Ser Leu Leu Asp Ser Asp Gly Lys Thr Tyr Leu Asn
1               5                   10                  15


<210> SEQ ID NO 90
<211> LENGTH: 112
<212> TYPE: PRT
<213> ORGANISM: Artificial sequence
<220> FEATURE:
<223> OTHER INFORMATION: Synthesized

<400> SEQUENCE: 90

Glu Val Gln Leu Val Gln Ser Gly Ala Glu Val Val Lys Pro Gly Ala
1               5                   10                  15

Thr Val Lys Ile Ser Cys Lys Ala Ser Gly Phe Thr Ile Lys Asp Tyr
            20                  25                  30
```

```
Tyr Leu His Trp Val Arg Gln Arg Pro Gly Lys Gly Leu Glu Trp Ile
        35                  40                  45

Gly Trp Ile Asp Pro Glu Asp Gly Glu Thr Val Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ser Thr Leu Asp Phe Trp Gly Gln Gly Thr Leu Val Thr Val Ser Ser
            100                 105                 110


<210> SEQ ID NO 91
<211> LENGTH: 112
<212> TYPE: PRT
<213> ORGANISM: Artificial sequence
<220> FEATURE:
<223> OTHER INFORMATION: Synthesized

<400> SEQUENCE: 91

Glu Val Gln Leu Val Gln Ser Gly Ala Glu Val Val Lys Pro Gly Ala
1               5                   10                  15

Thr Val Lys Ile Ser Cys Lys Ala Ser Gly Phe Thr Ile Lys Asp Tyr
            20                  25                  30

Tyr Leu His Trp Val Arg Gln Arg Pro Gly Lys Gly Leu Glu Trp Ile
        35                  40                  45

Gly Trp Ile Asp Pro Glu Asp Gly Glu Thr Val Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Leu Asp Phe Trp Gly Gln Gly Thr Leu Val Thr Val Ser Ser
            100                 105                 110


<210> SEQ ID NO 92
<211> LENGTH: 17
<212> TYPE: PRT
<213> ORGANISM: Artificial sequence
<220> FEATURE:
<223> OTHER INFORMATION: Synthesized

<400> SEQUENCE: 92

Trp Ile Asp Pro Glu Asp Gly Glu Thr Val Tyr Asp Pro Lys Phe Gln
1               5                   10                  15

Gly


<210> SEQ ID NO 93
<211> LENGTH: 421
<212> TYPE: DNA
<213> ORGANISM: Artificial sequence
<220> FEATURE:
<223> OTHER INFORMATION: Synthesized

<400> SEQUENCE: 93

caagtgcagc tgcagcagag cggggcagaa ttggtcaagc ccggagcgtc agtgaagctg      60

agctgcaccg cctccggctt caacatcaaa gactactatc ttcactgggt caagcaacgg     120

cctgaacagg gcctggagtg gattggttgg atcgacccag aaaacggcga caccgtgtac     180

gatccgaagt ttcaggggaa ggccaccatc actgctgata cgtcctcgaa caccgcctac     240
```

ctccaactga gctccctgac ttccgaggac actgccgtgt acttctgttc caccctggac 300
ttctggggac agggaactac cctcaccgtg tcctcggcca gcactaaggg gcctagcgtc 360
tttccgctgg ccccgtcctc caagtccact tcgggtggaa ccgcggcact ggggtgcctc 420
g 421

<210> SEQ ID NO 94
<211> LENGTH: 421
<212> TYPE: DNA
<213> ORGANISM: Artificial sequence
<220> FEATURE:
<223> OTHER INFORMATION: Synthesized

<400> SEQUENCE: 94
gaagtgcagc tcgtgcagtc cggtgccgaa gtcgtgaaac cgggagccag cgtgaagatt 60
agctgcaagg cctcagggtt caacatcaag gactattacc ttcactgggt cagacagcgg 120
cctggaaagg gcttggagtg gatcggatgg attgaccccg agaacggcga caccgtgtac 180
gatccgaagt ttcagggccg cgcaaccatc actgctgaca cctccaccga taccgcgtac 240
ctggaactct cgagcctgac ttccgaggat acggccgtgt acttctgttc caccctggac 300
ttctggggac aagggactct ggtcaccgtg tcctcggcca gcactaaggg gcctagcgtc 360
tttccgctgg ccccgtcctc caagtccact tcgggtggaa ccgcggcact ggggtgcctc 420
g 421

<210> SEQ ID NO 95
<211> LENGTH: 421
<212> TYPE: DNA
<213> ORGANISM: Artificial sequence
<220> FEATURE:
<223> OTHER INFORMATION: Synthesized

<400> SEQUENCE: 95
gaggtgcaac tggtgcagtc cggagccgaa gtcgtgaagc cgggagccac cgtgaagatt 60
tcgtgcaaag cgtcagggtt taacatcaag gactactatc tgcactgggt ccgccagagg 120
cccgggaagg gcctcgagtg gatcggttgg atcgaccctg aaaacggcga caccatctac 180
gatccaaagt tccagggcag agccactatt accgctgaca cgagcaccga tactgcatac 240
atggaattgt cctccctgcg gtccgaggat actgccgtgt actactgtag caccctggac 300
ttctggggac agggaaccct tgtgaccgtg tcgtccgcca gcactaaggg gcctagcgtc 360
tttccgctgg ccccgtcctc caagtccact tcgggtggaa ccgcggcact ggggtgcctc 420
g 421

<210> SEQ ID NO 96
<211> LENGTH: 421
<212> TYPE: DNA
<213> ORGANISM: Artificial sequence
<220> FEATURE:
<223> OTHER INFORMATION: Synthesized

<400> SEQUENCE: 96
gaggtgcagc tcgtgcagtc cggtgctgaa gtcgtgaagc ccggcgcaac tgtgaagatt 60
agctgcaagg cctcagggtt cacgatcaag gactactatc tgcactgggt ccgccaacgg 120
ccaggaaagg gactggagtg gatcggatgg atcgatcctg aaaacggcga caccatctac 180
gacccgaaat ttcaggggag agtgaccatt accgccgata cctccaccga cactgcgtac 240
atggaactgt ccagccttcg gtccgaggac accgccgtgt actactgttc gaccctggat 300

```
ttctggggac agggcactct cgtgactgtg tcgtccgcca gcactaaggg gcctagcgtc    360

tttccgctgg ccccgtcctc caagtccact tcgggtggaa ccgcggcact ggggtgcctc    420

g                                                                    421
```

```
<210> SEQ ID NO 97
<211> LENGTH: 421
<212> TYPE: DNA
<213> ORGANISM: Artificial sequence
<220> FEATURE:
<223> OTHER INFORMATION: Synthesized

<400> SEQUENCE: 97

gaagtgcaac tggtgcagtc cggcgcagaa gtcgtgaagc ctggagccac cgtgaagatc     60

agctgcaagg cctccggctt caccatcaaa gactactact tgcactgggt cagacagcgc    120

ccaggaaagg gtctggaatg gattggatgg attgaccccg aggacgggga gactatctac    180

gatccgaagt ttcagggccg ggtcaccatc acggctgata cctcgaccga cactgcgtac    240

atggaacttt cctcgctgcg gtccgaggac accgccgtgt attactgttc caccctggat    300

ttctggggac aggggactct cgtgactgtg tcaagcgcca gcactaaggg gcctagcgtc    360

tttccgctgg ccccgtcctc caagtccact tcgggtggaa ccgcggcact ggggtgcctc    420

g                                                                    421
```

```
<210> SEQ ID NO 98
<211> LENGTH: 421
<212> TYPE: DNA
<213> ORGANISM: Artificial sequence
<220> FEATURE:
<223> OTHER INFORMATION: Synthesized

<400> SEQUENCE: 98

gaagtgcaac tggtgcagtc cggcgcagaa gtcgtgaagc ctggagccac cgtgaagatc     60

agctgcaagg cctccggctt caccatcaaa gactactact tgcactgggt cagacagcgc    120

ccaggaaagg gtctggaatg gattggatgg attgaccccg aggacgggga gactgtgtac    180

gatccgaagt ttcagggccg ggtcaccatc acggctgata cctcgaccga cactgcgtac    240

atggaacttt cctcgctgcg gtccgaggac accgccgtgt atttctgttc caccctggat    300

ttctggggac aggggactct cgtgactgtg tcaagcgcca gcactaaggg gcctagcgtc    360

tttccgctgg ccccgtcctc caagtccact tcgggtggaa ccgcggcact ggggtgcctc    420

g                                                                    421
```

```
<210> SEQ ID NO 99
<211> LENGTH: 421
<212> TYPE: DNA
<213> ORGANISM: Artificial sequence
<220> FEATURE:
<223> OTHER INFORMATION: Synthesized

<400> SEQUENCE: 99

gaagtgcaac tggtgcagtc cggcgcagaa gtcgtgaagc ctggagccac cgtgaagatc     60

agctgcaagg cctccggctt caccatcaaa gactactact tgcactgggt cagacagcgc    120

ccaggaaagg gtctggaatg gattggatgg attgaccccg aggacgggga gactgtgtac    180

gatccgaagt ttcagggccg ggtcaccatc acggctgata cctcgaccga cactgcgtac    240

atggaacttt cctcgctgcg gtccgaggac accgccgtgt attactgttc caccctggat    300
```

ttctggggac aggggactct cgtgactgtg tcaagcgcca gcactaaggg gcctagcgtc 360
tttccgctgg ccccgtcctc caagtccact tcgggtggaa ccgcggcact ggggtgcctc 420
g 421

<210> SEQ ID NO 100
<211> LENGTH: 336
<212> TYPE: DNA
<213> ORGANISM: Artificial sequence
<220> FEATURE:
<223> OTHER INFORMATION: Synthesized

<400> SEQUENCE: 100
gatgtcgtga tgacccagac gccgctgacc ctgtccgtga ctatcggcca gcccgcgtcc 60
atttcgtgca agagcagcca gtccctgctg gactccgacg gaaagaccta cctgaactgg 120
ctgttgcaac ggccgggaca gtcacccaag cgcctcatct atctggtgtc caagctcgac 180
tcgggagtgc ctgataggtt ttcgggatcc ggcagcggga ccgacttcac cctgaaaatc 240
tcaagagtgg aagccgagga ccttggtgtc cattactgtt ggcagggtac ccacttccca 300
tacactttcg ggccggcac taagctcgaa ctgaag 336

<210> SEQ ID NO 101
<211> LENGTH: 336
<212> TYPE: DNA
<213> ORGANISM: Artificial sequence
<220> FEATURE:
<223> OTHER INFORMATION: Synthesized

<400> SEQUENCE: 101
gatgtcgtga tgacccagtc gccgctgtcc ctgtccgtga ccctgggaca gccagcctcc 60
attagctgca agagcagcca gtccttgctg gactcagacg gaaagaccta tctgaactgg 120
ctgctgcaaa ggcccggcca gtccccgaag agactcatct acctcgtgtc gaagctggac 180
tccggcgtgc ctgatcgctt ctcgggttcc gggtctggaa ctgacttcac cctcaaaatc 240
tcacgggtcg aagccgagga cgtgggcgtg tactactgtt ggcagggtac ccactttccc 300
tacactttcg ggcgggaac taagcttgag atcaag 336

<210> SEQ ID NO 102
<211> LENGTH: 336
<212> TYPE: DNA
<213> ORGANISM: Artificial sequence
<220> FEATURE:
<223> OTHER INFORMATION: Synthesized

<400> SEQUENCE: 102
gatgtcgtga tgacccagag ccccctgtcc ctgagcgtga ctctggggga accggccagc 60
atttcatgcc ggtcctcaca atcgctgctc gactccgacg gaaagaccta tttgaactgg 120
ctgcagcaaa gaccaggaca gtcccctcgc cggctcatct acctggtgtc caagcttgac 180
tcgggcgtgc cggataggtt ctccgggtcc ggaagcggca ccgacttcac tctgaaaatc 240
tcgcgcgtgg aagccgagga cgtgggagtc tactactgtt ggcagggtac ccacttcccc 300
tacacgtttg gccagggtac caagctcgag atcaag 336

<210> SEQ ID NO 103
<211> LENGTH: 330
<212> TYPE: PRT
<213> ORGANISM: Homo sapiens

<400> SEQUENCE: 103

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 104
<211> LENGTH: 107
<212> TYPE: PRT
<213> ORGANISM: Homo sapiens

<400> SEQUENCE: 104

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 105
<211> LENGTH: 993
<212> TYPE: DNA
<213> ORGANISM: Artificial sequence
<220> FEATURE:
<223> OTHER INFORMATION: Synthesized

<400> SEQUENCE: 105

gccagcacta aggggcctag cgtctttccg ctggccccgt cctccaagtc cacttcgggt     60

ggaaccgcgg cactggggtg cctcgtgaag gactacttcc ccgagccggt caccgtgtcc    120

tggaactcgg gagccctgac ctccggagtg catactttcc ctgcggtgct gcagtcctcc    180

gggctctact cgctgtcaag cgtggtcacc gtcccgagct catccctggg tactcagacc    240

tacatttgca acgtgaacca caaaccttcc aacaccaagg tcgacaagaa agtggagcct    300

aagagctgcg acaagaccca cacctgtccc ccgtgtcccg cccctgagct gctgggcggc    360

cccagcgtgt tcctcttccc gcctaagccg aaggacactc tgatgatctc gagaacccct    420

gaagtgacct gtgtggtggt ggatgtgtcc cacgaggatc cggaagtgaa gttcaattgg    480

tacgtggacg gagtggaagt ccataacgcc aagaccaagc cccgcgagga acagtacaac    540

tcaacttacc gggtggtgtc agtgctgacc gtgctgcacc aagattggct gaacgggaag    600

gagtacaagt gcaaagtctc caacaaggcg ctgccggccc ccattgaaaa gaccatcagc    660

aaggctaagg gccagccccg ggaaccacag gtctacacct tgccccccttc ccgggaggaa   720

atgaccaaga accaagtgtc gctgacgtgc ctggtcaagg gcttttatcc atctgacatc    780

gccgtggagt gggaaagcaa cggccagccg gaaaacaact acaagactac cccgcctgtg    840

ctggactccg acggctcgtt cttcctgtat tccaagctca ccgtggataa gtccagatgg    900

cagcagggca atgtgttcag ctgcagcgtg atgcatgagg ccctgcacaa ccactacact    960

cagaaatcac tgtccctttc ccccggaaag taa                                 993


<210> SEQ ID NO 106
<211> LENGTH: 324
<212> TYPE: DNA
<213> ORGANISM: Artificial sequence
<220> FEATURE:
<223> OTHER INFORMATION: Synthesized
```

-continued

```
<400> SEQUENCE: 106

cgaactgtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg ttaa                                           324
```

ANTIBODIES RECOGNIZING TAU

CROSS REFERENCE TO RELATED APPLICATIONS

This application is a national stage entry of PCT/US2019/060616 filed Nov. 8, 2019, which claims the priority to PCT/US2018/059895 filed Nov. 8, 2018 and U.S. 62/758,421 filed Nov. 9, 2018, which are hereby incorporated by reference.

REFERENCE TO A SEQUENCE LISTING

This application includes an electronic sequence listing in a file named 50887-0028US1 Sequence Listing.TXT, created on Nov. 8, 2019 and containing 96,408 bytes, which is hereby incorporated by reference in its entirety for all purposes.

BACKGROUND OF THE INVENTION

Tau is a well-known human protein that can exist in phosphorylated forms (see, e.g., Goedert, Proc. Natl. Acad. Sci. U.S.A. 85:4051-4055(1988); Goedert, EMBO J. 8:393-399(1989); Lee, Neuron 2:1615-1624(1989); Goedert, Neuron 3:519-526(1989); Andreadis, Biochemistry 31:10626-10633(1992). Tau has been reported to have a role in stabilizing microtubules, particularly in the central nervous system. Total tau (t-tau, i.e., phosphorylated and unphosphorylated forms) and phospho-tau (p-tau, i.e., phosphorylated tau) are released by the brain in response to neuronal injury and neurodegeneration and have been reported to occur at increased levels in the CSF of Alzheimer's patients relative to the general population (Jack et al., Lancet Neurol 9: 119-28 (2010)).

Tau is the principal constituent of neurofibrillary tangles, which together with plaques are a hallmark characteristic of Alzheimer's disease. The tangles constitute abnormal fibrils measuring 10 nm in diameter occurring in pairs wound in a helical fashion with a regular periodicity of 80 nm. The tau within neurofibrillary tangles is abnormally phosphorylated (hyperphosphorylated) with phosphate groups attached to specific sites on the molecule. Severe involvement of neurofibrillary tangles is seen in the layer II neurons of the entorhinal cortex, the CA1 and subicular regions of the hippocampus, the amygdala, and the deeper layers (layers III, V, and superficial VI) of the neocortex in Alzheimer's disease. Hyperphosphorylated tau has also been reported to interfere with microtubule assembly, which may promote neuronal network breakdown.

Tau inclusions are part of the defining neurophathology of several neurodegenerative diseases including Alzheimer's disease, frontotemporal lobar degeneration, progressive supranuclear palsy and Pick's disease.

BRIEF SUMMARY OF THE CLAIMED INVENTION

In one aspect, the invention provides an antibody specifically binding to human tau, comprising a mature heavy chain variable region comprising CDRs H1, H2 and H3 comprising SEQ ID NOS:8, 9, and a sequence of LDF, respectively except that position H28 can be occupied by N or T, H54 can be occupied by N or D, H56 can be occupied by D or E, and position H58 occupied by V or I, and a mature light chain variable region comprising CDRs L1, L2 and L3 comprising SEQ ID NOS:12, 13, and 14 respectively, except that position L24 can be occupied by K or R, wherein at least one of the following positions is occupied by the amino acid as specified: H1 is occupied by Q, H5 is occupied by Q, H11 is occupied by L, H20 is occupied by L, H23 is occupied by T, H38 is occupied by K, H75 is occupied by S, H56 is occupied by E, H58 is occupied by I, L10 is occupied by T, L17 is occupied by E, L24 is occupied by R, L37 is occupied by Q, L83 is occupied by L, L86 is occupied by H, L100 is occupied by A or Q, L106 is occupied by L.

In some such antibodies, CDR-H1 comprises SEQ ID NO:8 or SEQ ID NO:86, CDR-H2 comprises SEQ ID NO:9, SEQ ID NO:87, SEQ ID NO:88, or SEQ ID NO:92, CDR-H3 comprises a sequence of LDF, CDR-L1 comprises SEQ ID NO:12 or SEQ ID NO:89, CDR-L2 comprises SEQ ID NO:13, and CDR-L3 comprises SEQ ID NO:14. In some such antibodies, CDR-H1 comprises SEQ ID NO:8 or SEQ ID NO:86, CDR-H2 comprises SEQ ID NO:9, SEQ ID NO:87, or SEQ ID NO:88, CDR-H3 comprises a sequence of LDF, CDR-L1 comprises SEQ ID NO:12 or SEQ ID NO:89, CDR-L2 comprises SEQ ID NO:13, and CDR-L3 comprises SEQ ID NO:14. In some such antibodies, CDR-H1 comprises SEQ ID NO:86, CDR-H2 comprises SEQ ID NO:92, CDR-H3 comprises a sequence of LDF, CDR-L1 comprises SEQ ID NO: 12 or SEQ ID NO:89, CDR-L2 comprises SEQ ID NO:13, and CDR-L3 comprises SEQ ID NO:14.

In some such antibodies, CDR-H1 has an amino acid sequence comprising SEQ ID NO:86. In some such antibodies, CDR-H2 has an amino acid sequence comprising SEQ ID NO:87. In some such antibodies, CDR-H2 has an amino acid sequence comprising SEQ ID NO:88. In some such antibodies, CDR-H2 has an amino acid sequence comprising SEQ ID NO:92. In some such antibodies, CDR-L1 has an amino acid sequence comprising SEQ ID NO:89.

In some such antibodies, CDR-H1 has an amino acid sequence comprising SEQ ID NO:86 and CDR-H2 has an amino acid sequence comprising SEQ ID NO:87. In some such antibodies, CDR-H1 has an amino acid sequence comprising SEQ ID NO:86 and CDR-H2 has an amino acid sequence comprising SEQ ID NO:88. In some such antibodies, CDR-H1 has an amino acid sequence comprising SEQ ID NO:86 and CDR-H2 has an amino acid sequence comprising SEQ ID NO:92.

In some such antibodies, the antibody is a humanized antibody, veneered antibody, or chimeric antibody.

In some antibodies, the humanized mature heavy chain variable region having an amino acid sequence at least 95% identical to any one of SEQ ID NOs:76-80 and SEQ ID NOs:90-91 and the humanized mature light chain variable region has an amino acid sequence at least 90% identical to any one of SEQ ID NOs:83-85. In some antibodies, the humanized mature heavy chain variable region has an amino acid sequence at least 95% identical to any one of SEQ ID NOs:76-80 and the humanized mature light chain variable region has an amino acid sequence at least 90% identical to any one of SEQ ID NOs:83-85. In some antibodies, the humanized mature heavy chain variable region has an amino acid sequence at least 95% identical to any one of SEQ ID NOs:90-91 and the humanized mature light chain variable region has an amino acid sequence at least 90% identical to any one of SEQ ID NOs:83-85.

In some such antibodies, at least one of the following positions in the VH region is occupied by the amino acid as specified: H93 is occupied by S and H94 is occupied by T. In some such antibodies, positions H93 and H94 are occupied by S and T, respectively.

In some such antibodies, position H91 in the VH region is occupied by F.

In some such antibodies, at least one of the following positions in the VH region is occupied by the amino acid as specified: H1 is occupied by E, H5 is occupied by V, H11 is occupied by V, H20 is occupied I, H23 is occupied by K, H38 is occupied by R, H42 is occupied by G, H43 is occupied by K, H66 is occupied by R, H75 is occupied by T, H76 is occupied by D, H81 is occupied by E, H108 is occupied by L, H109 is occupied by V. In some antibodies, positions H1, H5, H11, H20, H23, H38, H42, H43, H66, H75, H76, H81, H108, and H109 in the VH region are occupied by E, V, V, I, K, R, G, K, R, T, D, E, L, and V, respectively.

In some such antibodies, at least one of the following positions in the VH region is occupied by the amino acid as specified: H17 is occupied by T, H80 is occupied by M, H83 is occupied by R. In some antibodies, positions H17, H80, and H83 in the VH region are occupied by T, M, and R, respectively.

In some such antibodies, position H58 in the VH region is occupied by I.

In some such antibodies, at least one of the following positions in the VH region is occupied by the amino acid as specified: H28 is occupied by T, H67 is occupied by V. In some antibodies, positions H28 and H67 in the VH region are occupied by T and V, respectively.

In some such antibodies, at least one of the following positions in the VH region is occupied by the amino acid as specified: H54 is occupied by D, H56 is occupied by E. In some antibodies, positions H54 and H56 in the VH region are occupied by D and E, respectively.

In some such antibodies, at least one of the following positions in the VH region is occupied by the amino acid as specified: H1 is occupied by Q or E, H5 is occupied by Q or V, H11 is occupied by L or V, H17 is occupied by S or T, H20 is occupied by L or I, H23 is occupied by T or K, H28 is occupied by N or T, H38 is occupied by K or R, H42 is occupied by E or G, H43 is occupied by Q or K, H54 is occupied by N or D, H56 is occupied by D or E, H58 is occupied by V or I, H66 is occupied by K or R, H67 is occupied by A or V, H75 is occupied by S or T, H76 is occupied by N or D, H80 is occupied by L or M, H81 is occupied by Q or E, H83 is occupied by T or R, H91 is occupied by F or Y, H93 is occupied by S, H94 is occupied by T, H108 is occupied by T or L, H109 is occupied by L or V.

In some antibodies, positions H91, H93, and H94 in the VH region are occupied by F, S, and T, respectively. In some antibodies, positions H1, H5, H11, H20, H23, H38, H42, H43, H66, H75, H76, H81, H91, H93, H94, H108, and H109 in the VH region are occupied by E, V, V, I, K, R, G, K, R, T, D, E, F, S, T, L, and V, respectively. In some antibodies, positions H1, H5, H11, H17, H20, H23, H38, H42, H43, H58, H66, H75, H76, H80, H81, H83, H93, H94, H108, and H109 in the VH region are occupied by E, V, V, T, I, K, R, G, K, I, R, T, D, M, E, R, S, T, L, and V, respectively. In some antibodies, positions H1, H5, H11, H17, H20, H23, H28, H38, H42, H43, H58, H66, H67, H75, H76, H80, H81, H83, H93, H94, H108, and H109 in the VH region are occupied by E, V, V, T, I, K, T, R, G, K, I, R, V, T, D, M, E, R, S, T, L, and V, respectively. In some antibodies, positions H1, H5, H11, H17, H20, H23, H28, H38, H42, H43, H54, H56, H58, H66, H67, H75, H76, H80, H81, H83, H93, H94, H108, and H109 in the VH region are occupied by E, V, V, T, I, K, T, R, G, K, D, E, I, R, V, T, D, M, E, R, S, T, L, and V, respectively. In some antibodies, positions H1, H5, H11, H17, H20, H23, H28, H38, H42, H43, H54, H56, H66, H67, H75, H76, H80, H81, H83, H91, H93, H94, H108, and H109 in the VH region are occupied by E, V, V, T, I, K, T, R, G, K, D, E, R, V, T, D, M, E, R, F, S, T, L, and V, respectively. In some antibodies, positions H1, H5, H11, H17, H20, H23, H28, H38, H42, H43, H54, H56, H66, H67, H75, H76, H80, H81, H83, H93, H94, H108, and H109 in the VH region are occupied by E, V, V, T, I, K, T, R, G, K, D, E, R, V, T, D, M, E, R, S, T, L, and V, respectively.

In some such antibodies, at least one of the following positions in the VL region is occupied by the amino acid as specified: L7 is occupied by S, L10 is occupied by S, L15 is occupied by L, L83 is occupied by V, L86 is occupied by Y, and L106 is occupied by I. In some antibodies, positions L7, L10, L15, L83, L86, and L106 are occupied by S, S, L, V, Y, and Y, respectively.

In some such antibodies, at least one of the following positions in the VL region is occupied by the amino acid as specified: L7 is T or S, L10 is T or S, L15 is I or L, L17 is Q or E, L24 is K or R, L37 is L or Q, L45 is K or R, L83 is L or V, L86 is H or Y, L100 is A or Q, L106 is L or I.

In some antibodies, positions L7, L10, L15, L83, L86, and L106 in the VL region are occupied by S, S, L, V, Y, and I, respectively. In some antibodies, positions L7, L10, L15, L17, L24, L37, L45, L83, L86, L100, and L106 in the VL region are occupied by S, S, L, E, R, Q, R, V, Y, Q, and I, respectively.

In some antibodies, the mature heavy chain variable region has an amino acid sequence of any one of SEQ ID NOs:76-80 and SEQ ID NOs:90-91 and the mature light chain variable region has an amino acid sequence of any one of SEQ ID NO:83-85. In some antibodies, the mature heavy chain variable region has an amino acid sequence of any one of SEQ ID NOs:76-80 and the mature light chain variable region has an amino acid sequence of any one of SEQ ID NO:83-85. In some antibodies, the mature heavy chain variable region has an amino acid sequence of any one of SEQ ID NOs:90-91 and the mature light chain variable region has an amino acid sequence of any one of SEQ ID NO:83-85.

In some antibodies, the mature heavy chain variable region has an amino acid sequence of SEQ ID NO:76 and the mature light chain variable region has an amino acid sequence of SEQ ID NO:83. In some antibodies, the mature heavy chain variable region has an amino acid sequence of SEQ ID NO:76 and the mature light chain variable region has an amino acid sequence of SEQ ID NO:84. In some antibodies, the mature heavy chain variable region has an amino acid sequence of SEQ ID NO:76 and the mature light chain variable region has an amino acid sequence of SEQ ID NO:85.

In some antibodies, the mature heavy chain variable region has an amino acid sequence of SEQ ID NO:77 and the mature light chain variable region has an amino acid sequence of SEQ ID NO:83. In some antibodies, the mature heavy chain variable region has an amino acid sequence of SEQ ID NO:77 and the mature light chain variable region has an amino acid sequence of SEQ ID NO:84. In some antibodies, the mature heavy chain variable region has an amino acid sequence of SEQ ID NO:77 and the mature light chain variable region has an amino acid sequence of SEQ ID NO:85.

In some antibodies, the mature heavy chain variable region has an amino acid sequence of SEQ ID NO:78 and the mature light chain variable region has an amino acid sequence of SEQ ID NO:83. In some antibodies, the mature heavy chain variable region has an amino acid sequence of SEQ ID NO:78 and the mature light chain variable region has an amino acid sequence of SEQ ID NO:84. In some antibodies, the mature heavy chain variable region has an amino acid sequence of SEQ ID NO:78 and the mature light chain variable region has an amino acid sequence of SEQ ID NO:85.

In some antibodies, the mature heavy chain variable region has an amino acid sequence of SEQ ID NO:79 and the mature light chain variable region has an amino acid sequence of SEQ ID NO:83. In some antibodies, the mature heavy chain variable region has an amino acid sequence of SEQ ID NO:79 and the mature light chain variable region has an amino acid sequence of SEQ ID NO:84. In some antibodies, the mature heavy chain variable region has an amino acid sequence of SEQ ID NO:79 and the mature light chain variable region has an amino acid sequence of SEQ ID NO:85.

In some antibodies, the mature heavy chain variable region has an amino acid sequence of SEQ ID NO:80 and the mature light chain variable region has an amino acid sequence of SEQ ID NO:83. In some antibodies, he mature heavy chain variable region has an amino acid sequence of SEQ ID NO:80 and the mature light chain variable region has an amino acid sequence of SEQ ID NO:84. In some antibodies, the mature heavy chain variable region has an amino acid sequence of SEQ ID NO:80 and the mature light chain variable region has an amino acid sequence of SEQ ID NO:85.

In some antibodies, the mature heavy chain variable region has an amino acid sequence of SEQ ID NO:90 and the mature light chain variable region has an amino acid sequence of SEQ ID NO:83. In some antibodies, the mature heavy chain variable region has an amino acid sequence of SEQ ID NO:90 and the mature light chain variable region has an amino acid sequence of SEQ ID NO:84. In some antibodies, the mature heavy chain variable region has an amino acid sequence of SEQ ID NO:90 and the mature light chain variable region has an amino acid sequence of SEQ ID NO:85.

In some antibodies, the mature heavy chain variable region has an amino acid sequence of SEQ ID NO:91 and the mature light chain variable region has an amino acid sequence of SEQ ID NO:83. In some antibodies, the mature heavy chain variable region has an amino acid sequence of SEQ ID NO:91 and the mature light chain variable region has an amino acid sequence of SEQ ID NO:84. In some antibodies, the mature heavy chain variable region has an amino acid sequence of SEQ ID NO:91 and the mature light chain variable region has an amino acid sequence of SEQ ID NO:85.

For example, the antibody can be a chimeric antibody. For example, the antibody can be a veneered antibody.

The antibody can be an intact mouse, chimeric, veneered or humanized antibody or a binding fragment, single-chain antibody Fab fragment, Fab'2 fragment, or single chain Fv. Some of the antibodies have a human IgG1 isotype, while others may have a human IgG2 or IgG4 isotype. Some antibodies have the mature light chain variable region fused to a light chain constant region and the mature heavy chain variable region fused to a heavy chain constant region. The heavy chain constant region of some antibodies is a mutant form of a natural human heavy chain constant region which has reduced binding to a Fcγ receptor relative to the natural human heavy chain constant region. In some antibodies, the mature heavy chain variable region is fused to a heavy chain constant region having the sequence of SEQ ID NO:103 with or without the C-terminal lysine and/or the mature light chain variable region is fused to a light chain constant region having the sequence of SEQ ID NO:104.

Some antibodies may have at least one mutation in the constant region, such as a mutation that reduces complement fixation or activation by the constant region, for example, a mutation at one or more of positions 241, 264, 265, 270, 296, 297, 318, 320, 322, 329 and 331 by EU numbering. Some antibodies have an alanine at positions 318, 320 and 322. Some antibodies can be at least 95% w/w pure. The antibody can be conjugated to a therapeutic, cytotoxic, cytostatic, neurotrophic, or neuroprotective agent.

In another aspect, the invention provides a pharmaceutical composition comprising any of the antibodies disclosed herein and a pharmaceutically-acceptable carrier.

In another aspect, the invention provides a nucleic acid encoding the heavy chain and/or light chain of any of the antibodies disclosed herein, a recombinant expression vector comprising the nucleic acid and a host cell transformed with the recombinant expression vector. For example, the nucleic acid can have a sequence comprising any one of SEQ ID NOs:30-31, 93-99, 100-102, and 105-106. In another example, the nucleic acid can have a sequence comprising any one of SEQ ID NOs:30-31, 93-97, 100-102, and 105-106. In another example, the nucleic acid can have a sequence comprising any one of SEQ ID NOs:30-31, 98-99, 100-102, and 105-106.

In another aspect, the invention provides a vector comprising a nucleic acid encoding a mature heavy chain variable region and a mature light chain variable region operably linked to one or more regulatory sequences to effect expression in a mammalian cell of any of the antibodies disclosed herein, a host cell comprising the nucleic acid, and a method of expressing an antibody in a mammalian cell comprising incorporating the nucleic acid into the genome of a transgenic animal, whereby the antibody is expressed.

Some vectors comprise a nucleic acid further encoding a heavy chain constant region fused to the mature heavy chain variable region and a light chain constant region fused to the mature light chain variable region. In some vectors, the encoded heavy chain constant region has the sequence of SEQ ID NO:103 with or without the C-terminal lysine and the encoded light chain constant region has the sequence of SEQ ID NO:104. In some vectors, the heavy chain constant region is encoded by the sequence of SEQ ID NO: 105 and the light chain constant region is encoded by the sequence of SEQ ID NO: 106.

In some vectors, the expressed antibody encoded by the nucleic acid is a scFv. In some vectors, the expressed antibody encoded by the nucleic acid is a Fab fragment.

In some vectors, the one or more regulatory sequences include one or more of a promoter, enhancer, ribosome binding site, and transcription termination signal. In some vectors, the nucleic acid further encodes signal peptides fused to the mature heavy and light chain variable regions. In some vectors, the nucleic acid is codon-optimized for expression in a host cell. In some vectors, the one or more regulatory sequences include a eukaryotic promoter. In some vectors, the nucleic acid further encodes a selectable gene.

In another aspect, the invention provides first and second vectors respectively comprising nucleic acids encoding a mature heavy chain variable region and a mature light chain variable region, each operably linked to one or more regulatory sequences to effect expression in a mammalian cell of any of the antibodies disclosed herein, a host cell comprising the nucleic acids, and a method of expressing an antibody in a mammalian cell comprising incorporating the nucleic acids into the genome of a transgenic animal, whereby the antibody is expressed.

In some vectors, the nucleic acids respectively further encode a heavy chain constant region fused to the mature heavy chain variable region and a light chain constant region fused to the mature light chain variable region. In some vectors, the encoded heavy chain constant region has the sequence of SEQ ID NO:103 with or without the C-terminal lysine and the encoded light chain constant region has the sequence of SEQ ID NO:104. In some vectors, the heavy chain constant region is encoded by the sequence of SEQ ID NO: 105 and the light chain constant region is encoded by the sequence of SEQ ID NO: 106.

In yet another aspect, the invention provides methods of humanizing any non-human antibody described herein, for example, mouse antibody 3D6, wherein 3D6 is characterized by a mature heavy chain variable region of SEQ ID NO:7 and a mature light chain variable region of SEQ ID NO:11. Such methods can involve selecting one or more acceptor antibodies, synthesizing a nucleic acid encoding a humanized heavy chain comprising CDRs of the mouse heavy chain and a nucleic acid encoding a humanized light chain comprising CDRs of the mouse antibody light chain, and expressing the nucleic acids in a host cell to produce a humanized antibody.

Methods of producing antibodies, such as a humanized, chimeric or veneered antibody, for example humanized, chimeric or veneered forms of 3D6, are also provided. In such methods, cells transformed with nucleic acids encoding the heavy and light chains of the antibody are cultured so that the cells secrete the antibody. The antibody can then be purified from the cell culture media.

Cell lines producing any of the antibodies disclosed herein can be produced by introducing a vector encoding heavy and light chains of the antibody and a selectable marker into cells, propagating the cells under conditions to select for cells having increased copy number of the vector, isolating single cells from the selected cells; and banking cells cloned from a single cell selected based on yield of antibody.

Some cells can be propagated under selective conditions and screened for cell lines naturally expressing and secreting the antibody in an amount of at least 100 mg/L/$10^6$ cells/24 hours. Single cells can be isolated from the selected cells. Cells cloned from a single cell can then be banked. Single cells can be selected based on desirable properties, such as the yield of the antibody. Exemplary cell lines are cell lines expressing 3D6.

The invention also provides methods of inhibiting or reducing aggregation of tau in a subject having or at risk of developing a tau-mediated amyloidosis, comprising administering to the subject an effective regime of an antibody disclosed herein, thereby inhibiting or reducing aggregation of tau in the subject. Exemplary antibodies include humanized versions of 3D6.

Also provided are methods of treating or effecting prophylaxis of a tau-related disease in a subject, comprising administering an effective regime of an antibody disclosed herein and thereby treating or effecting prophylaxis of the disease. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). In some methods, the tau-related disease is Alzheimer's disease. In some methods the patient is an ApoE4 carrier.

Also provided are methods of reducing aberrant transmission of tau comprising administering an effective regime of an antibody disclosed herein and thereby reducing transmission of tau.

Also provided are methods of inducing phagocytosis of tau comprising administering an effective regime of an antibody disclosed herein and thereby inducing phagocytosis of tau.

Also provided are methods of inhibiting tau aggregation or deposition comprising administering an effective regime of an antibody disclosed herein thereby inhibiting tau aggregation or deposition.

Also provided are methods of inhibiting formation of tau tangles comprising administering an effective regime of an antibody disclosed herein.

The invention also provides a method of detecting tau protein deposits in a subject having or at risk of a disease associated with tau aggregation or deposition comprising administering to a subject an antibody disclosed herein, and detecting the antibody bound to tau in the subject. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). In some embodiments, the antibody is administered by intravenous injection into the body of the subject. In some embodiments, the antibody is administered directly to the brain of the subject by intracranial injection or by drilling a hole through the skull of the subject. In some embodiments, the antibody is labeled. In some embodiments, the antibody is labeled with a fluorescent label, a paramagnetic label, or a radioactive label. In some embodiments, the radioactive label is detected using positron emission tomography (PET) or single-photon emission computed tomography (SPECT).

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of the antibody bound to tau in the subject, administering the treatment to the subject, measuring a second level of tau protein deposits in the in subject after treatment by administering to a subject the antibody, and detecting the antibody bound to tau in the subject, wherein a decrease in the level of tau protein deposits indicates a positive response to treatment.

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of antibody bound to tau in the subject, administering the treatment to the subject, measuring a second level of tau protein deposits in the in subject after treatment by administering to a subject the antibody, and detecting a second amount of antibody bound to tau in the subject, wherein no change in the level of tau protein deposits or a small increase in tau protein deposits indicates a positive response to treatment.

BRIEF DESCRIPTION OF THE DRAWINGS

FIGS. 3A, 3B, and 3C depict results of ELISA screening assays for selected mouse monoclonal anti-tau antibodies.

BRIEF DESCRIPTION OF THE SEQUENCES

Figure 1:
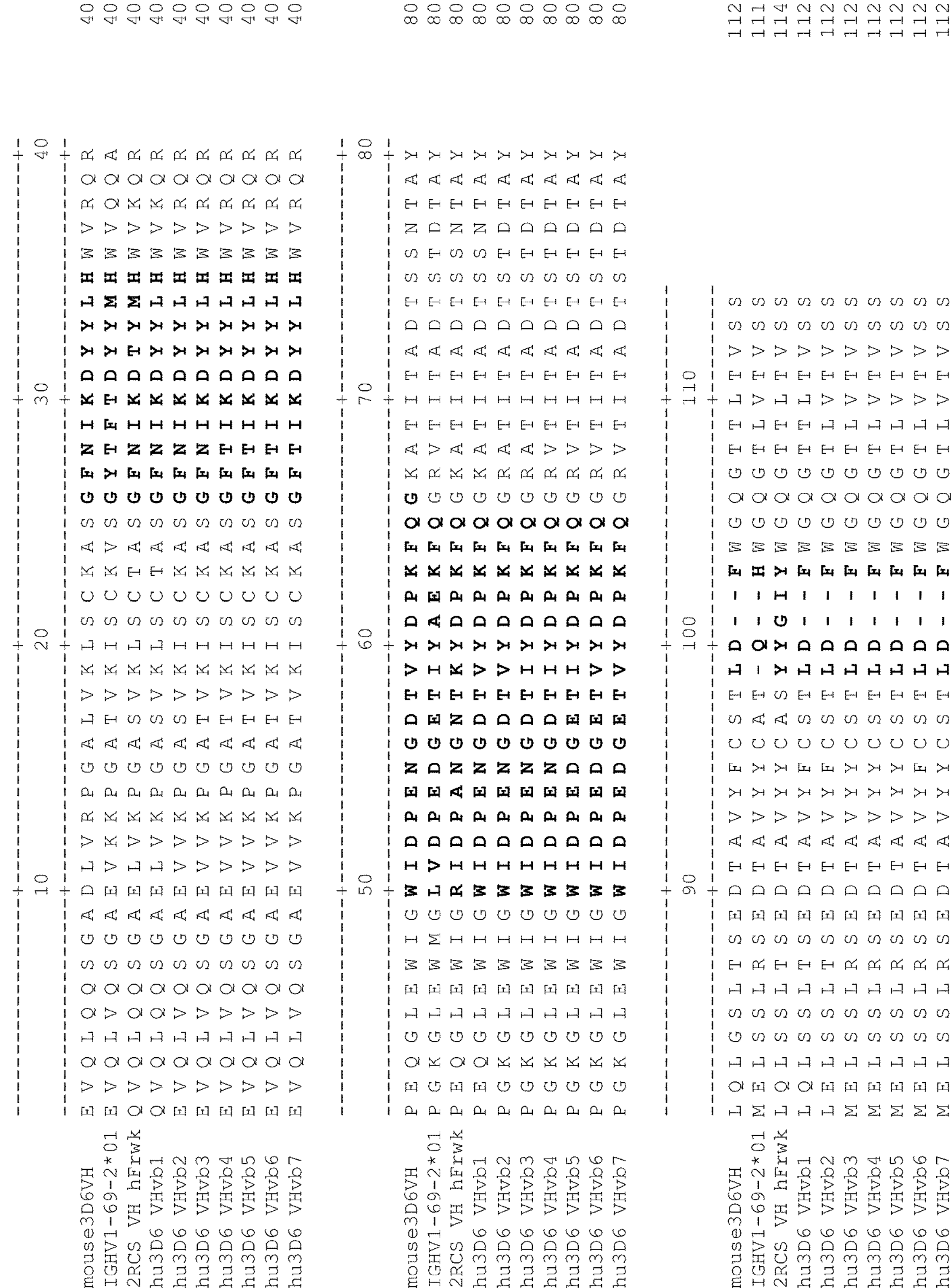
FIG. 1 depicts an alignment of heavy chain variable regions of the mouse 3D6 antibody (SEQ ID NO:7) and humanized versions of the 3D6 antibody (hu3D6VHvb1, hu3D6VHvb2, hu3D6VHvb3, hu3D6VHvb4, hu3D6VHvb5, hu3D6VHvb6, and hu3D6VHvb7) with human germline heavy chain variable region sequence IGHV1-69-2*01 (SEQ ID NO:25) and with human acceptor heavy chain variable region sequence 2RCS VH hFrwk (SEQ ID NO:75). hu3D6VHvb1 is SEQ ID NO:76, hu3D6VHvb2 is SEQ ID NO:77, hu3D6VHvb3 is SEQ ID NO:78, hu3D6VHvb4 is SEQ ID NO:79, hu3D6VHvb5 is SEQ ID NO:80, hu3D6VHvb6 is SEQ ID NO:90, and hu3D6VHvb7 is SEQ ID NO:91. The CDRs as defined by Kabat/Chothia Composite are in boldface.

SEQ ID NO:1 sets forth the amino acid sequence of an isoform of human tau (Swiss-Prot P10636-8).

SEQ ID NO:2 sets forth the amino acid sequence of an isoform of human tau (Swiss-Prot P10636-7).

SEQ ID NO:3 sets forth the amino acid sequence of an isoform of human tau (Swiss-Prot P10636-6), (4R0N human tau).

SEQ ID NO:4 sets forth the amino acid sequence of an isoform of human tau (Swiss-Prot P10636-5)

SEQ ID NO:5 sets forth the amino acid sequence of an isoform of human tau (Swiss-Prot P10636-4).

SEQ ID NO:6 sets forth the amino acid sequence of an isoform of human tau (Swiss-Prot P10636-2).

SEQ ID NO:7 sets forth the amino acid sequence of the heavy chain variable region of the mouse 3D6 antibody.

SEQ ID NO:8 sets forth the amino acid sequence of Kabat/Chothia composite CDR-H1 of the mouse 3D6 antibody.

SEQ ID NO:9 sets forth the amino acid sequence of Kabat CDR-H2 of the mouse 3D6 antibody.

The amino acid sequence of Kabat CDR-H3 of the mouse 3D6 antibody is LDF.

SEQ ID NO:11 sets forth the amino acid sequence of the light chain variable region of the mouse 3D6 antibody and of the mouse 6A10 antibody.

SEQ ID NO:12 sets forth the amino acid sequence of Kabat CDR-L1 of the mouse 3D6 antibody and of the mouse 6A10 antibody.

SEQ ID NO:13 sets forth the amino acid sequence of Kabat CDR-L2 of the mouse 3D6 antibody and of the mouse 6A10 antibody.

SEQ ID NO:14 sets forth the amino acid sequence of Kabat CDR-L3 of the mouse 3D6 antibody and of the mouse 6A10 antibody.

SEQ ID NO:15 sets forth the amino acid sequence of heavy chain variable region of the humanized 3D6 antibody hu3D6VHv1.

SEQ ID NO:16 sets forth the amino acid sequence of heavy chain variable region of the humanized 3D6 antibody hu3D6VHv2.

SEQ ID NO:17 sets forth the amino acid sequence of heavy chain variable region of the humanized 3D6 antibody hu3D6VHv1b.

SEQ ID NO:18 sets forth the amino acid sequence of heavy chain variable region of the humanized 3D6 antibody hu3D6VHv1bA11.

SEQ ID NO:19 sets forth the amino acid sequence of heavy chain variable region of the humanized 3D6 antibody hu3D6VHv5:

SEQ ID NO:20 sets forth the amino acid sequence of the light chain variable region of the humanized 3D6 antibody hu3D6VLv1.

SEQ ID NO:21 sets forth the amino acid sequence of the light chain variable region of the humanized 3D6 antibody hu3D6VLv2.

SEQ ID NO:22 sets forth the amino acid sequence of the light chain variable region of the humanized 3D6 antibody hu3D6VLv3.

SEQ ID NO:23 sets forth the amino acid sequence of the light chain variable region of the humanized 3D6 antibody hu3D6VLv4.

SEQ ID NO:24 sets forth the amino acid sequence of the heavy chain variable acceptor Acc. #BAC01986.1.

SEQ ID NO:25 sets forth the amino acid sequence of the heavy chain variable acceptor Acc. #IMGT #IGHV1-69-2*01.

SEQ ID NO:26 sets forth the amino acid sequence of the heavy chain variable acceptor Acc. #IMGT #IGKJ1*01.

SEQ ID NO:27 sets forth the amino acid sequence of the light chain variable acceptor Acc. #IMGT #IGKV2-30*02

SEQ ID NO:28 sets forth the amino acid sequence of the light chain variable acceptor Acc. #IMGT #IGKJ2*01.

SEQ ID NO:29 sets forth the amino acid sequence of the light chain variable acceptor Acc. #AAZ09048.1.

SEQ ID NO:30 sets forth a nucleic acid sequence encoding the heavy chain variable region of the mouse 3D6 antibody.

SEQ ID NO:31 sets forth a nucleic acid sequence encoding the light chain variable region of the mouse 3D6 antibody.

SEQ ID NO:32 sets forth the amino acid sequence of Kabat CDR-H1 of the mouse 3D6 antibody.

SEQ ID NO:33 sets forth the amino acid sequence of Chothia CDR-H1 of the mouse 3D6 antibody.

SEQ ID NO:34 sets forth the amino acid sequence of Chothia CDR-H2 of the mouse 3D6 antibody.

SEQ ID NO:35 sets forth the amino acid sequence of AbM CDR-H2 of the mouse 3D6 antibody.

SEQ ID NO:36 sets forth the amino acid sequence of Contact CDR-L1 of the mouse 3D6 antibody.

SEQ ID NO:37 sets forth the amino acid sequence of Contact CDR-L2 of the mouse 3D6 antibody.

SEQ ID NO:38 sets forth the amino acid sequence of Contact CDR-L3 of the mouse 3D6 antibody.

SEQ ID NO:39 sets forth the amino acid sequence of Contact CDR-H1 of the mouse 3D6 antibody.

SEQ ID NO:40 sets forth the amino acid sequence of Contact CDR-H2 of the mouse 3D6 antibody.

SEQ ID NO:41 sets forth the amino acid sequence of Contact CDR-H3 of the mouse 3D6 antibody.

SEQ ID NO:42 sets forth the amino acid sequence of an alternate Kabat-Chothia Composite CDR-H1 of a humanized 3D6 antibody (as in hu3D6VHv5, hu3D6VHv1bA11B6G2, hu3D6VHv1bA11B6H3, hu3D6VHv1e, and hu3D6VHv1f).

SEQ ID NO:43 sets forth the amino acid sequence of an alternate Kabat CDR-H2 of a humanized 3D6 antibody (as in hu3D6VHv5 and hu3D6VHv1bA11B6H3).

Figure 2:
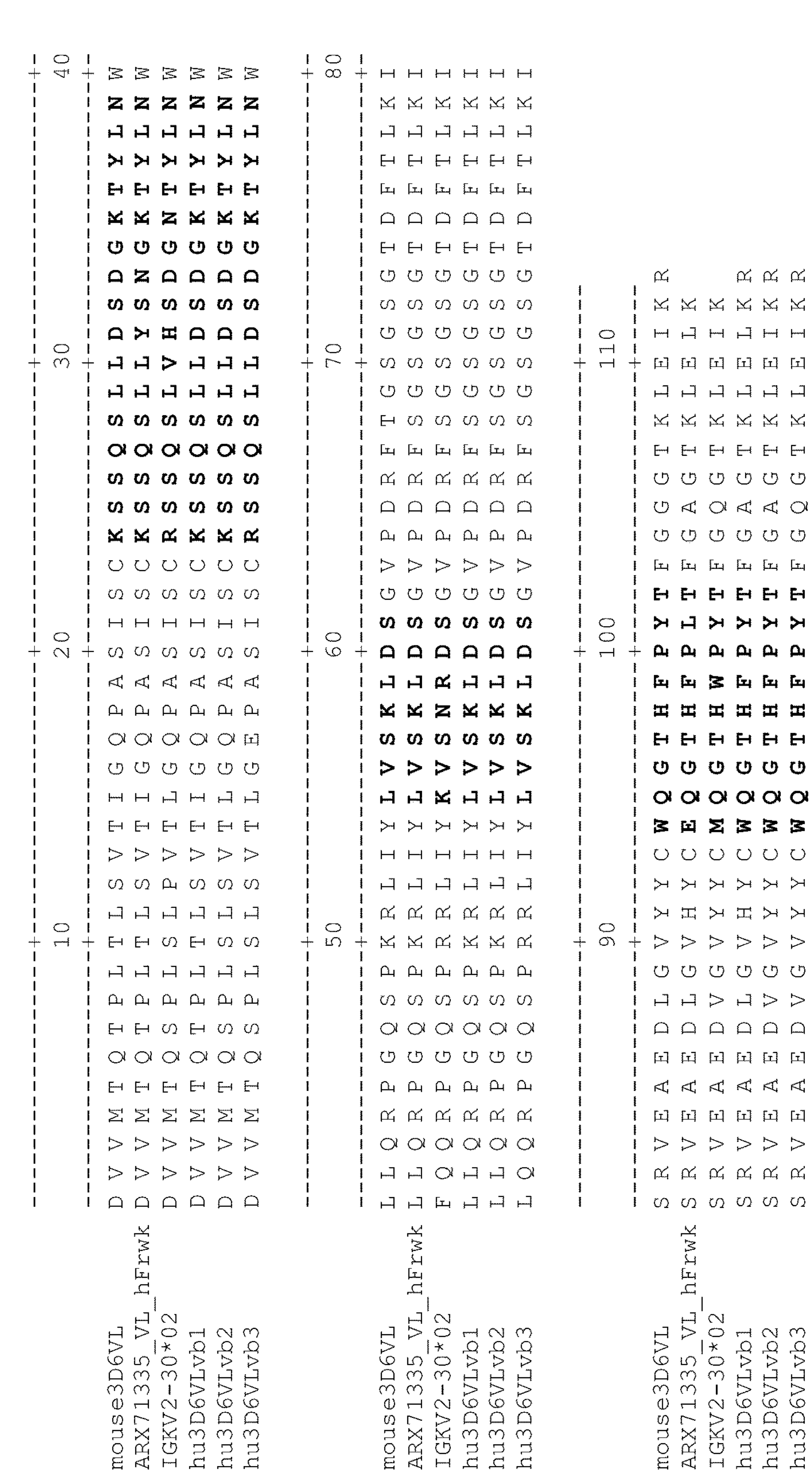
FIG. 2 depicts an alignment of light chain variable regions of the mouse 3D6 antibody (SEQ ID NO: 11) and humanized versions of the 3D6 antibody (hu3D6VLvb1, hu3D6VLvb2, and hu3D6VLvb3) with human germline light chain variable region sequence IGKV2-30*02 (SEQ ID NO:27) and with human acceptor ARX71335_VL_hFrwk (SEQ ID NO:82). hu3D6VLvb1 is SEQ ID NO:83, hu3D6VLvb2 is SEQ ID NO:84, and hu3D6VLvb3 is SEQ ID NO:85. The CDRs as defined by Kabat are in boldface.

SEQ ID NO:44 sets forth the consensus amino acid sequence among the heavy chain variable regions of the mouse 3D6 and selected humanized 3D6 antibodies (VHv1, VHv2, VHv1b, VHv1bA11, and VHv5) (labeled "Majority' in FIG. 2 of PCT/IB2017/052544.

SEQ ID NO:45 sets forth the consensus amino acid sequence between the light chain variable regions of the mouse 3D6 and selected humanized 3D6 antibodies (labeled "Majority' in FIG. 3 of PCT/IB2017/052544).

SEQ ID NO:46 sets forth the amino acid sequence of heavy chain variable region of the humanized 3D6 antibody hu3D6VHv1bA11B6G2.

SEQ ID NO:47 sets forth the amino acid sequence of heavy chain variable region of the humanized 3D6 antibody hu3D6VHv1bA11B6H3.

SEQ ID NO:48 sets forth the amino acid sequence of heavy chain variable region of the humanized 3D6 antibody hu3D6VHv1c.

SEQ ID NO:49 sets forth the amino acid sequence of heavy chain variable region of the humanized 3D6 antibody hu3D6VHv1d.

SEQ ID NO:50 sets forth the amino acid sequence of heavy chain variable region of the humanized 3D6 antibody hu3D6VHv1e.

SEQ ID NO:51 sets forth the amino acid sequence of heavy chain variable region of the humanized 3D6 antibody hu3D6VHv1f.

SEQ ID NO:52 sets forth the amino acid sequence of heavy chain variable region of the humanized 3D6 antibody hu3D6VHv3.

SEQ ID NO:53 sets forth the amino acid sequence of heavy chain variable region of the humanized 3D6 antibody hu3D6VHv3b.

SEQ ID NO:54 sets forth the amino acid sequence of heavy chain variable region of the humanized 3D6 antibody hu3D6VHv3c.

SEQ ID NO:55 sets forth the amino acid sequence of heavy chain variable region of the humanized 3D6 antibody hu3D6VHv4.

SEQ ID NO:56 sets forth the amino acid sequence of heavy chain variable region of the humanized 3D6 antibody hu3D6VHv4b.

SEQ ID NO:57 sets forth the amino acid sequence of heavy chain variable region of the humanized 3D6 antibody hu3D6VHv4c.

SEQ ID NO:58 sets forth the amino acid sequence of an alternate Kabat-Chothia Composite CDR-H1 of a humanized 3D6 antibody (as in hu3D6VH1c).

SEQ ID NO:59 sets forth the amino acid sequence of an alternate Kabat-Chothia Composite CDR-H1 of a humanized 3D6 antibody (as in hu3D6VHv1d, hu3D6VHv3c, and hu3D6VHv4c).

SEQ ID NO:60 sets forth the amino acid sequence of an alternate Kabat-Chothia Composite CDR-H1 of a humanized 3D6 antibody (as in hu3D6VHv3b and hu3D6VHv4b).

SEQ ID NO:61 sets forth the amino acid sequence of an alternate Kabat CDR-H2 of a humanized 3D6 antibody (as in hu3D6VHv1bA11B6G2).

SEQ ID NO:62 sets forth the amino acid sequence of an alternate Kabat CDR-H2 of a humanized 3D6 antibody (as in hu3D6VHv1c, hu3D6VHv3b, AND hu3D6VHv4b.

SEQ ID NO:63 sets forth the amino acid sequence of an alternate Kabat CDR-H2 of a humanized 3D6 antibody (as in hu3D6VHv1d, hu3D6VHv1f, hu3D6VHv3c, and hu3D6VHv4c).

SEQ ID NO:64 sets forth the amino acid sequence of an alternate Kabat CDR-H2 of a humanized 3D6 antibody (as in hu3D6VHv1e).

SEQ ID NO:65 sets forth the amino acid sequence of an alternate Kabat CDR-H3 of a humanized 3D6 antibody (as in hu3D6VHv1f).

SEQ ID NO:66 sets forth the amino acid sequence of the heavy chain variable region of the mouse 6A10 antibody.

SEQ ID NO:67 sets forth the amino acid sequence of Kabat/Chothia composite CDR-H1 of the mouse 6A10 antibody.

SEQ ID NO:68 sets forth the amino acid sequence of Kabat CDR-H2 of the mouse 6A10 antibody.

SEQ ID NO:69 sets forth the amino acid sequence of Kabat CDR-H3 of the mouse 6A10 antibody.

SEQ ID NO:70 sets for the amino acid sequence of the VH region of mouse antibody (pdb code 1CR9) used as a structure template for heavy chain humanization.

SEQ ID NO:71 sets forth the consensus amino acid sequence among the heavy chain variable regions of the selected humanized 3D6 antibodies (VHv1, VHv1b, VHv1bA11, VHv1bA11B6G2, VHv1bA11B6H3, VHv1c, VHv1d, VHv1e, VHv1f, VHv2, VHv3, VHv3b, VHv3c, VHv4, VHv4b, VHv4c, and VHv5) (labeled "Majority' in FIGS. 4A and 4B of PCT/IB2017/052544).

SEQ ID NO:72 sets forth the amino acid sequence of the heavy chain of a chimeric 3D6 antibody.

SEQ ID NO:73 sets forth the amino acid sequence of the light chain of a chimeric 3D6 antibody.

SEQ ID NO:74 sets forth the amino acid sequence of heavy chain variable structural model Acc. #5MYX-VH_mSt.

SEQ ID NO:75 sets forth the amino acid sequence of heavy chain variable acceptor Acc. #2RCS-VH_huFrwk.

SEQ ID NO:76 sets forth the amino acid sequence of heavy chain variable region of the humanized 3D6 antibody hu3D6VHvb1.

SEQ ID NO:77 sets forth the amino acid sequence of heavy chain variable region of the humanized 3D6 antibody hu3D6VHvb2.

SEQ ID NO:78 sets forth the amino acid sequence of heavy chain variable region of the humanized 3D6 antibody hu3D6VHvb3.

SEQ ID NO:79 sets forth the amino acid sequence of heavy chain variable region of the humanized 3D6 antibody hu3D6VHvb4.

SEQ ID NO:80 sets forth the amino acid sequence of heavy chain variable region of the humanized 3D6 antibody hu3D6VHvb5.

SEQ ID NO:81 sets forth the amino acid sequence of light chain variable structural model Acc. #5MYX-VL_mSt.

SEQ ID NO:82 sets forth the amino acid sequence of light chain variable acceptor Acc. #ARX71335-VL_huFrwk.

SEQ ID NO:83 sets forth the amino acid sequence of light chain variable region of the humanized 3D6 antibody hu3D6VLvb1.

SEQ ID NO:84 sets forth the amino acid sequence of light chain variable region of the humanized 3D6 antibody hu3D6VLvb2.

SEQ ID NO:85 sets forth the amino acid sequence of light chain variable region of the humanized 3D6 antibody hu3D6VLvb3.

SEQ ID NO:86 sets forth the amino acid sequence of an alternate Kabat-Chothia Composite CDR-H1 of a humanized 3D6 antibody (as in hu3D6VHvb4 and hu3D6VHvb5).

SEQ ID NO:87 sets forth the amino acid sequence of an alternate Kabat CDR-H2 of a humanized 3D6 antibody (as in hu3D6VHvb3 and hu3D6VHvb4).

SEQ ID NO:88 sets forth the amino acid sequence of an alternate Kabat CDR-H2 of a humanized 3D6 antibody (as in hu3D6VHvb5).

SEQ ID NO:89 sets forth the amino acid sequence of an alternate Kabat CDR-L1 of a humanized 3D6 antibody (as in hu3D6VLvb3).

SEQ ID NO:90 sets forth the amino acid sequence of heavy chain variable region of the humanized 3D6 antibody hu3D6VHvb6.

SEQ ID NO:91 sets forth the amino acid sequence of heavy chain variable region of the humanized 3D6 antibody hu3D6VHvb7.

SEQ ID NO:92 sets forth the amino acid sequence of an alternate Kabat CDR-H2 of a humanized 3D6 antibody (as in hu3D6VHvb6 and hu3D6VHvb7).

SEQ ID NO:93 sets forth a nucleic acid sequence encoding the heavy chain variable region of the humanized 3D6 antibody hu3D6VHvb1.

SEQ ID NO:94 sets forth a nucleic acid sequence encoding the heavy chain variable region of the humanized 3D6 antibody hu3D6VHvb2.

SEQ ID NO:95 sets forth a nucleic acid sequence encoding the heavy chain variable region of the humanized 3D6 antibody hu3D6VHvb3.

SEQ ID NO:96 sets forth a nucleic acid sequence encoding the heavy chain variable region of the humanized 3D6 antibody hu3D6VHvb4.

SEQ ID NO:97 sets forth a nucleic acid sequence encoding the heavy chain variable region of the humanized 3D6 antibody hu3D6VHvb5.

SEQ ID NO:98 sets forth a nucleic acid sequence encoding the heavy chain variable region of the humanized 3D6 antibody hu3D6VHvb6.

SEQ ID NO:99 sets forth a nucleic acid sequence encoding the heavy chain variable region of the humanized 3D6 antibody hu3D6VHvb7.

SEQ ID NO:100 sets forth a nucleic acid sequence encoding the light chain variable region of the humanized 3D6 antibody hu3D6VLvb1.

SEQ ID NO:101 sets forth a nucleic acid sequence encoding the light chain variable region of the humanized 3D6 antibody hu3D6VLvb2.

SEQ ID NO:102 sets forth a nucleic acid sequence encoding the light chain variable region of the humanized 3D6 antibody hu3D6VLvb3.

SEQ ID NO:103 sets forth the amino acid sequence of an exemplary IgG1 heavy chain constant region.

SEQ ID NO:104 sets forth the amino acid sequence of an exemplary kappa light chain constant region.

SEQ ID NO:105 sets forth a nucleic acid sequence encoding an exemplary IgG1 heavy chain constant region.

SEQ ID NO:106 sets forth a nucleic acid sequence encoding an exemplary kappa light chain constant region.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity and/or avidity of at least $10^6$, $10^7$, $10^8$, $10^9$, $10^{10}$, $10^{11}$, or $10^{12}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3. When the application discloses a VL sequence with R as the C-terminal residue, the R can alternatively be considered as being the N-terminal residue of the light chain constant region. Thus, the application should also be understood as disclosing the VL sequence without the C-terminal R.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, MD, 1987 and 1991), the Chothia definition (Chothia & Lesk, *J. Mol. Biol.* 196:901-917, 1987; Chothia et al., *Nature* 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24-L34 | L24-L34 | L24-L34 | L24-L34 | L30-L36 |
| L2 | L50-L56 | L50-L56 | L50-L56 | L50-L56 | L46-L55 |
| L3 | L89-L97 | L89-L97 | L89-L97 | L89-L97 | L89-L96 |
| H1 | H31-H35B | H26-H32 . . . H34* | H26-H35B* | H26-H35B | H30-H35B |
| H2 | H50-H65 | H52-H56 | H50-H65 | H50-H58 | H47-H58 |
| H3 | H95-H102 | H95-H102 | H95-H102 | H95-H102 | H93-H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The term "antibody" includes intact antibodies and binding fragments thereof. Typically, fragments compete with the intact antibody from which they were derived for specific binding to the target including separate heavy chains, light chains Fab, Fab', $F(ab')_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.,* 79:315-321 (1990); Kostelny et al., *J. Immunol.,* 148:1547-53 (1992)). In some bispecific antibodies, the two different heavy/light chain pairs include a humanized 3D6 heavy chain/light chain pair and a heavy chain/light chain pair specific for a different epitope on tau than that bound by 3D6.

In some bispecific antibodies, one heavy chain/light chain pair is a humanized 3D6 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., *Science* 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the reference antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include tau-related disease-affected regions, or at least not known or suspect to include diseased regions of a given type. Control samples can be obtained from individuals not afflicted with the tau-related disease. Alternatively, control samples can be obtained from patients afflicted with the tau-related disease. Such samples can be obtained at the same time as a biological sample thought to comprise the tau-related disease or on a different occasion. A biological sample and a control sample can both be obtained from the same tissue. Preferably, control samples consist essentially or entirely of normal, healthy regions and can be used in comparison to a biological sample thought to comprise tau-related disease-affected regions. Preferably, the tissue in the control sample is the same type as the tissue in the biological sample. Preferably, the tau-related disease-affected cells thought to be in the biological sample arise from the same cell type (e.g., neurons or glia) as the type of cells in the control sample.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

The term "positive response to treatment" refers to a more favorable response in an individual patient or average response in a population of patients relative to an average response in a control population not receiving treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses insubstantial variations, such as values within a standard margin of error of measurement (e.g., SEM) of a stated value.

Statistical significance means p≤0.05.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that bind to tau. Some antibodies specifically bind to epitopes within the microtubule binding region (MTBR) region of human tau. Some antibodies bind to tau irrespective of phosphorylation state. Some antibodies of the invention serve to inhibit or delay tau-associated pathologies and associated symptomatic deterioration. Although an understanding of mechanism is not required for practice of the invention, a reduction in toxicity may occur as a result of the antibody inducing phagocytosis of tau, inhibiting tau from inter or intramolecular aggregation, or from binding to other molecules, by stabilizing a non-toxic conformation, by inhibiting intercellular or intracellular transmission of pathogenic tau forms, by blockade of tau phosphorylation, by preventing binding of tau to cells, or by inducing proteolytic cleavage of tau, among other mechanisms. The antibodies of the invention or agents that induce such antibodies can be used in methods of treating or effecting prophylaxis of Alzheimer's and other diseases associated with tau.

II. Target Molecules

Unless otherwise apparent from the context, reference to tau means a natural human form of tau including all isoforms irrespective of whether posttranslational modification (e.g., phosphorylation, glycation, or acetylation) is present. There are six major isoforms (splice variants) of tau occurring in the human brain. The longest of these variants has 441 amino acids, of which the initial met residue is cleaved. Residues are numbered according to the 441 isoform. Thus, for example, reference to a phosphorylation at position 404 means position 404 of the 441 isoform, or corresponding position of any other isoform when maximally aligned with the 441 isoform. The amino acid sequences of the isoforms and Swiss-Prot numbers are indicated below.

```
P10636-8
                                              (SEQ ID NO: 1)
        10          20          30          40
MAEPRQEFEV  MEDHAGTYGL  GDRKDQGGYT  MHQDQEGDTD

        50          60          70          80
AGLKESPLQT  PTEDGSEEPG  SETSDAKSTP  TAEDVTAPLV

        90         100         110         120
DEGAPGKQAA  AQPHTEIPEG  TTAEEAGIGD  TPSLEDEAAG

       130         140         150         160
HVTQARMVSK  SKDGTGSDDK  KAKGADGKTK  IATPRGAAPP

       170         180         190         200
GQKGQANATR  IPAKTPPAPK  TPPSSGEPPK  SGDRSGYSSP
```

-continued

```
       210         220         230         240
GSPGTPGSRS  RTPSLPTPPT  REPKKVAVVR  TPPKSPSSAK

       250         260         270         280
SRLQTAPVPM  PDLKNVKSKI  GSTENLKHQP  GGGKVQIINK

       290         300         310         320
KLDLSNVQSK  CGSKDNIKHV  PGGGSVQIVY  KPVDLSKVTS

       330         340         350         360
KCGSLGNIHH  KPGGGQVEVK  SEKLDFKDRV  QSKIGSLDNI

       370         380         390         400
THVPGGGNKK  IETHKLTFRE  NAKAKTDHGA  EIVYKSPVVS

       410         420         430         440
GDTSPRHLSN  VSSTGSIDMV  DSPQLATLAD  EVSASLAKQG  L
```

```
P10636-7
                                              (SEQ ID NO: 2)
        10          20          30          40
MAEPRQEFEV  MEDHAGTYGL  GDRKDQGGYT  MHQDQEGDTD

        50          60          70          80
AGLKESPLQT  PTEDGSEEPG  SETSDAKSTP  TAEAEEAGIG

        90         100         110         120
DTPSLEDEAA  GHVTQARMVS  KSKDGTGSDD  KKAKGADGKT

       130         140         150         160
KIATPRGAAP  PGQKGQANAT  RIPAKTPPAP  KTPPSSGEPP

       170         180         190         200
KSGDRSGYSS  PGSPGTPGSR  SRTPSLPTPP  TREPKKVAVV

       210         220         230         240
RTPPKSPSSA  KSRLQTAPVP  MPDLKNVKSK  IGSTENLKHQ

       250         260         270         280
PGGGKVQIIN  KKLDLSNVQS  KCGSKDNIKH  VPGGGSVQIV

       290         300         310         320
YKPVDLSKVT  SKCGSLGNIH  HKPGGGQVEV  KSEKLDFKDR

       330         340         350         360
VQSKIGSLDN  ITHVPGGGNK  KIETHKLTFR  ENAKAKTDHG

       370         380         390         400
AEIVYKSPVV  SGDTSPRHLS  NVSSTGSIDM  VDSPQLATLA

       410
DEVSASLAKQ  GL
```

```
P10636-6 (4R0N human tau)
                                              (SEQ ID NO: 3)
        10          20          30          40
MAEPRQEFEV  MEDHAGTYGL  GDRKDQGGYT  MHQDQEGDTD

        50          60          70          80
AGLKAEEAGI  GDTPSLEDEA  AGHVTQARMV  SKSKDGTGSD

        90         100         110         120
DKKAKGADGK  TKIATPRGAA  PPGQKGQANA  TRIPAKTPPA

       130         140         150         160
PKTPPSSGEP  PKSGDRSGYS  SPGSPGTPGS  RSRTPSLPTP

       170         180         190         200
PTREPKKVAV  VRTPPKSPSS  AKSRLQTAPV  PMPDLKNVKS

       210         220         230         240
KIGSTENLKH  QPGGGKVQII  NKKLDLSNVQ  SKCGSKDNIK

       250         260         270         280
HVPGGGSVQI  VYKPVDLSKV  TSKCGSLGNI  HHKPGGGQVE

       290         300         310         320
VKSEKLDFKD  RVQSKIGSLD  NITHVPGGGN  KKIETHRLTF

       330         340         350         360
RENAKAKTDH  GAEIVYKSPV  VSGDTSPRHL  SNVSSTGSID
```

-continued

```
       370        380
MVDSPQLATL ADEVSASLAK QGL
```

P10636-5

(SEQ ID NO: 4)

```
        10         20         30         40
MAEPRQEFEV MEDHAGTYGL GDRKDQGGYT MHQDQEGDTD

        50         60         70         80
AGLKESPLQT PTEDGSEEPG SETSDAKSTP TAEDVTAPLV

        90        100        110        120
DEGAPGKQAA AQPHTEIPEG TTAEEAGIGD TPSLEDEAAG

       130        140        150        160
HVTQARMVSK SKDGTGSDDK KAKGADGKTK IATPRGAAPP

       170        180        190        200
GQKGQANATR IPAKTPPAPK TPPSSGEPPK SGDRSGYSSP

       210        220        230        240
GSPGTPGSRS RTPSLPTPPT REPKKVAVVR TPPKSPSSAK

       250        260        270        280
SRLQTAPVPM PDLKNVKSKI GSTENLKHQP GGGKVQIVYK

       290        300        310        320
PVDLSKVTSK CGSLGNIHHK PGGGQVEVKS EKLDFKDRVQ

       330        340        350        360
SKIGSLDNIT HVPGGGNKKI ETHKLTFREN AKAKTDHGAE

       370        380        390        400
IVYKSPVVSG DTSPRHLSNV SSTGSIDMVD SPQLATLADE

       410
VSASLAKQGL
```

P10636-4

(SEQ ID NO: 5)

```
        10         20         30         40
MAEPRQEFEV MEDHAGTYGL GDRKDQGGYT MHQDQEGDTD

        50         60         70         80
AGLKESPLQT PTEDGSEEPG SETSDAKSTP TAEAEEAGIG

        90        100        110        120
DTPSLEDEAA GHVTQARMVS KSKDGTGSDD KKAKGADGKT

       130        140        150        160
KIATPRGAAP PGQKGQANAT RIPAKTPPAP KTPPSSGEPP

       170        180        190        200
KSGDRSGYSS PGSPGTPGSR SRTPSLPTPP TREPKKVAVV

       210        220        230        240
RTPPKSPSSA KSRLQTAPVP MPDLKNVKSK IGSTENLKHQ

       250        260        270        280
PGGGKVQIVY KPVDLSKVTS KCGSLGNIHH KPGGGQVEVK

       290        300        310        320
SEKLDFKDRV QSKIGSLDNI THVPGGGNKK IETHKLTFRE

       330        340        350        360
NAKAKTDHGA EIVYKSPVVS GDTSPRHLSN VSSTGSIDMV

       370        380
DSPQLATLAD EVSASLAKQG L
```

P10636-2

(SEQ ID NO: 6)

```
        10         20         30         40
MAEPRQEFEV MEDHAGTYGL GDRKDQGGYT MHQDQEGDTD

        50         60         70         80
AGLKAEEAGI GDTPSLEDEA AGHVTQARMV SKSKDGTGSD

        90        100        110        120
DKKAKGADGK TKIATPRGAA PPGQKGQANA TRIPAKTPPA
```

-continued

```
       130        140        150        160
PKTPPSSGEP PKSGDRSGYS SPGSPGTPGS RSRTPSLPTP

       170        180        190        200
PTREPKKVAV VRTPPKSPSS AKSRLQTAPV PMPDLKNVKS

       210        220        230        240
KIGSTENLKH QPGGGKVQIV YKRVDLSKVT SKCGSLGNIH

       250        260        270        280
HKRGGGQVEV KSEKLDFKDR VQSKIGSLDN ITHVRGGGNK

       290        300        310        320
KIETHKLTFR ENAKAKTDHG AEIVYKSPVV SGDTSPTHLS

       330        340        350
NVSSTGSIDM VDSPQLATLA DEVSASLAKQ GL
```

Reference to tau includes known natural variations about 30 of which are listed in the Swiss-Prot database and permutations thereof, as well as mutations associated with tau pathologies, such as dementia, Pick's disease, supranuclear palsy, etc. (see, e.g., Swiss-Prot database and Poorkaj, et al. Ann Neurol. 43:815-825 (1998)). Some examples of tau mutations numbered by the 441 isoform are a lysine to threonine mutation at amino acid residue 257 (K257T), an isoleucine to valine mutation at amino acid position 260 (I260V); a glycine to valine mutation at amino acid position 272 (G272V); an asparagine to lysine mutation at amino acid position 279 (N279K); an asparagine to histidine mutation at amino acid position 296 (N296H); a proline to serine mutation at amino acid position 301 (P301S); a proline to leucine mutation at amino acid 301 (P301L); a glycine to valine mutation at amino acid position 303 (G303V); a serine to asparagine mutation at position 305 (S305N); a glycine to serine mutation at amino acid position 335 (G335S); a valine to methionine mutation at position 337 (V337M); a glutamic acid to valine mutation at position 342 (E342V); a lysine to isoleucine mutation at amino acid position 369 (K3691); a glycine to arginine mutation at amino acid position 389 (G389R); and an arginine to tryptophan mutation at amino acid position 406 (R406W).

Tau can be phosphorylated at one or more amino acid residues including tyrosine at amino acid positions 18, 29, 97, 310, and 394 serine at amino acid positions 184, 185, 198, 199, 202, 208, 214, 235, 237, 238, 262, 293, 324, 356, 396, 400, 404, 409, 412, 413, and 422; and threonine at amino acids positions 175, 181, 205, 212, 217, 231, and 403. Unless otherwise apparent from context, reference to tau, or their fragments includes the natural human amino acid sequences including isoforms, mutants, and allelic variants thereof.

III. Antibodies

A. Binding Specificity and Functional Properties

The invention provides antibodies that bind to tau. Some antibodies specifically bind to epitopes within the microtubule binding region (MTBR) region of human tau. Some antibodies bind to tau irrespective of phosphorylation state. Some antibodies bind to an epitope not including a residue subject to phosphorylation. These antibodies can be obtained by immunizing with a tau polypeptide purified from a natural source or recombinantly expressed. Antibodies can be screened for binding tau in unphosphorylated form as well as a form in which one or more residues susceptible to phosphorylation are phosphorylated. Such antibodies preferably bind with indistinguishable affinities or at least within a factor of 1.5, 2 or 3-fold to phosphorylated tau compared to non-phosphorylated tau (i.e., are "pan-specific"). 3D6 is an example of a pan-specific monoclonal antibody. The invention also provides antibodies binding to the same epitope as any of the foregoing antibodies, such as, for example, the epitope of 3D6. Also included are antibodies competing for binding to tau with any of the foregoing antibodies, such as, for example, competing with 3D6.

Unless otherwise apparent from context, reference to 3D6 should be understood as referring to any of the mouse, chimeric, veneered, and humanized forms of this antibody. This antibody specifically binds within the MTBR region of SEQ ID NO:1). This antibody is further characterized by its ability to bind both phosphorylated and unphosphorylated tau, both non-pathological and pathological forms and conformations of tau, and misfolded/aggregated forms of tau. An antibody designated 6A10 is another such exemplary mouse antibody. Unless otherwise apparent from context, reference to 6A10 should be understood as referring to any of the mouse, chimeric, veneered, and humanized forms of this antibody. Kabat/Chothia Composite CDRs of the heavy chain of 6A10 are designated SEQ ID NOs:67, 68, and 69, respectively, and Kabat CDRs of the light chain of 6A10 are designated SEQ ID NOs:12, 13, and 14, respectively. Mouse 6A10 shares 82.1% of VH sequence identity and 100% VL sequence identity with the VH chain and VL chain, respectively, of mouse 3D6.

Some antibodies of the invention bind to the same or overlapping epitope as an antibody designated 3D6. The sequences of the heavy and light chain mature variable regions of this antibody are designated SEQ ID NOs:7 and 11, respectively.

Kabat/Chothia Composite CDRs of the heavy chain of 3D6 are designated SEQ ID NOs:8, 9, and a sequence of LDF, respectively, and Kabat CDRs of the light chain of 3D6 are designated SEQ ID NOs:12, 13, and 14, respectively.

Table 2 indicates the 3D6 CDRs as defined by Kabat, Chothia, Composite of Chothia and Kabat (also referred to herein as "Kabat/Chothia Composite"), AbM, and Contact.

amino acid substitutions (e.g., conservative substitutions), deletions, or insertions are also included in the invention. Monoclonal antibodies having at least one or all six CDR(s) as defined by any conventional definition, but preferably Kabat, that are 90%, 95%, 99% or 100% identical to corresponding CDRs of 3D6 are also included.

The invention also provides antibodies having some or all (e.g., 3, 4, 5, and 6) CDRs entirely or substantially from 3D6. Such antibodies can include a heavy chain variable region that has at least two, and usually all three, CDRs entirely or substantially from the heavy chain variable region of 3D6 and/or a light chain variable region having at least two, and usually all three, CDRs entirely or substantially from the light chain variable region of 3D6. The antibodies can include both heavy and light chains. A CDR is substantially from a corresponding 3D6 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 3D6 in the amino acid sequence of the mature heavy and/or light chain variable regions and maintain their functional properties, and/or differ from 3D6 by a small number of functionally inconsequential amino acid substitutions (e.g., conservative substitutions), deletions, or insertions.

Some antibodies identified by such assays can bind to monomeric, misfolded, aggregated, phosphorylated, or unphosphorylated forms of tau or otherwise. Likewise, some antibodies are immunoreactive on non-pathological and pathological forms and conformations of tau.

B. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for

TABLE 2

3D6 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24-L34 | L24-L34 | L24-L34 | L24-L34 | L30-L36 |
| | SEQ ID NO: 12 | SEQ ID NO: 12 | SEQ ID NO: 12 | SEQ ID NO: 12 | SEQ ID NO: 36 |
| L2 | L50-L56 | L50-L56 | L50-L56 | L50-L56 | L46-L55 |
| | SEQ ID NO: 13 | SEQ ID NO: 13 | SEQ ID NO: 13 | SEQ ID NO: 13 | SEQ ID NO: 37 |
| L3 | L89-L97 | L89-L97 | L89-L97 | L89-L97 | L89-L96 |
| | SEQ ID NO: 14 | SEQ ID NO: 14 | SEQ ID NO: 14 | SEQ ID NO: 14 | SEQ ID NO: 38 |
| H1 | H31-H35B | H26-H32 | H26-H35B | H26-H35B | H30-H35B |
| | SEQ ID NO: 32 | SEQ ID NO: 33 | SEQ ID NO: 8 | SEQ ID NO: 8 | SEQ ID NO: 39 |
| H2 | H50-H65 | H52-H56 | H50-H65 | H50-H58 | H47-H58 |
| | SEQ ID NO: 9 | SEQ ID NO: 34 | SEQ ID NO: 9 | SEQ ID NO: 35 | SEQ ID NO: 40 |
| H3 | H95-H102 | H95-H102 | H95-H102 | H95-H102 | H93-H101 |
| | LDF | LDF | LDF | LDF | SEQ ID NO: 41 |

Other antibodies can be obtained by mutagenesis of cDNA encoding the heavy and light chains of an exemplary antibody, such as 3D36. Monoclonal antibodies that are at least 7000, 8000, 9000, 9500, 9600, 9700, 9800, or 9900 identical to 3D36 or any other exemplified antibody or antibody chain in amino acid sequence of the mature heavy and/or light chain variable regions and maintain its functional properties, and/or which differ from the respective antibody by a small number of functionally inconsequential example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical. To be classified as humanized under the 2014 World Health Organization (WHO) International non-proprietary names (INN) definition of humanized antibodies, an antibody must have at least 85% identity to human germline antibody sequences (i.e., prior to somatic hypermutation). Mixed antibodies are antibodies for which one antibody chain (e.g., heavy chain) meets the threshold but the other chain (e.g., light chain) does not meet the threshold. An antibody is classified as chimeric if neither chain meets the threshold, even though the variable framework regions for both chains were substantially human with some murine backmutations. See, Jones et al. (2016) The INNs and outs of antibody nonproprietary names, mAbs 8:1, 1-9, DOI: 10.1080/19420862.2015.1114320. See also "WHO-INN: International nonproprietary names (INN) for biological and biotechnological substances (a review)" (Internet) 2014, incorporated herein by reference. For the avoidance of doubt, the term "humanized" as used herein is not intended to be limited to the 2014 WHO INN definition of humanized antibodies. Some of the humanized antibodies provided herein have at least 85% sequence identity to human germline sequences and some of the humanized antibodies provided herein have less than 85% sequence identity to human germline sequences. Some of the heavy chains of the humanized antibodies provided herein have from about 60% to 100% sequence identity to human germ line sequences, such as, for example, in the range of about 60% to 69%, 70% to 79%, 80% to 84%, or 85% to 89%. Some heavy chains fall below the 2014 WHO INN definition and have, for example, about 64%, 65%, 66%, 67%, 68%, 69%, 70%, 71%, 72%, 73%, 74%, 75%, 76%, 77%, 78%, 79%, 80%, 81%, or 82%, 83%, or 84% sequence identity to human germ line sequences, while other heavy chains meet the 2014 WHO INN definition and have about 85%, 86%, 87%, 88%, 89% or greater sequence identity to human germ line sequences. Some of the light chains of the humanized antibodies provided herein have from about 60% to 100% sequence identity to human germ line sequences, such as, for example, in the range of about 80% to 84% or 85% to 89%. Some light chains fall below the 2014 WHO INN definition and have, for example, about 81%, 82%, 83% or 84% sequence identity to human germ line sequences, while other light chains meet the 2014 WHO INN definition and have about 85%, 86%, 87%, 88%, 89% or greater sequence identity to human germ line sequences. Some humanized antibodies provided herein that are "chimeric" under the 2014 WHO INN definition have heavy chains with less than 85% identity to human germ line sequences paired with light chains having less than 85% identity to human germ line sequences. Some humanized antibodies provided herein are "mixed" under the 2014 WHO INN definition, for example, having a heavy chain with at least 85% sequence identity to human germ line sequences paired with a light chain having less than 85% sequence identity to human germ line sequences, or vice versa. Some humanized antibodies provided herein meet the 2014 WHO INN definition of "humanized" and have a heavy chain with at least 85% sequence identity to human germ line sequences paired with a light chain having at least 85% sequence identity to human germ line sequences. Additional humanized antibodies of the invention meet the 2014 WHO INN definition of "mixed."

Although humanized antibodies often incorporate all six CDRs (defined by any conventional definition but preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.,* 320: 415-428, 2002; Iwahashi et al., *Mol. Immunol.* 36:1079-1091, 1999; Tamura et al, *J. Immunol.,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity and/or for meeting the WHO INN definition of "humanized". However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

An example of an acceptor sequence for the heavy chain is the human mature heavy chain variable region of humanized 48G7 Fab with PDB accession code 2RCS-VH_huFrwk (SEQ ID NO:75). The variable domains of 3D6 and 48G7 Fab also share identical lengths for the CDR-H1, H2 loops. Another example of an acceptor sequence for the heavy chain is the human mature heavy chain variable region IMGT #IGHV1-69-2*01 (SEQ ID NO:25). IMGT #IGHV1-69-2*01 (SEQ ID NO:25) shares the canonical form of mouse 3D6 heavy chain CDR-H1 and H2. IMGT

#IGHV1-69-2*01 (SEQ ID NO:25) belongs to human heavy chain subgroup 1. An example of an acceptor sequence for the light chain is the human mature light chain variable region with PDB accession code human antibody ARX71335 VL (SEQ ID NO:82). The variable light domain of 3D6 and ARX71335 antibody also share identical lengths for the CDR-L1, L2 and L3 loops. Another example of an acceptor sequence for the light chain is the human mature light chain variable region with IMGT #IGKV2-30*02 (SEQ ID NO:27). IMGT #IGKV2-30*02 (SEQ ID NO:27) has the same canonical classes for CDR-L1, CDR-L2 and L3 as mouse 3D6. IMGT #IGKV2-30*02 (SEQ ID NO:27) belongs to human kappa subgroup 2.

If more than one human acceptor antibody sequence is selected, a composite or hybrid of those acceptors can be used, and the amino acids used at different positions in the humanized light chain and heavy chain variable regions can be taken from any of the human acceptor antibody sequences used. For example, the human mature heavy chain variable regions of IMGT #IGHV1-69-2*01 (SEQ ID NO:25) and PDB accession code #2RCS-VH_huFrwk (SEQ ID NO:75) were used as acceptor sequences for humanization of the 3D6 mature heavy chain variable region. An example of a positions in which these two acceptors differ is position H17 (T or S). Humanized versions of the 3D6 heavy chain variable region can include either amino acid at this position. For example, the human mature light chain variable regions IMGT #IGKV2-30*02 (SEQ ID NO:27) and PDB code #ARX71335-VL_huFrwk (SEQ ID NO:82) were used as acceptor sequences for humanization of the 3D6 mature light chain variable region. An example of a position in which these two acceptors differ is position L100 (Q or A). Humanized versions of the 3D6 light chain variable region can include either amino acid at this position.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;

(2) is adjacent to a CDR region or within a CDR as defined by Chothia but not Kabat;

(3) otherwise interacts with a CDR region (e.g., is within about 6 Å of a CDR region), (e.g., identified by modeling the light or heavy chain on the solved structure of a homologous known immunoglobulin chain); or (4) is a residue participating in the VL-VH interface.

The invention provides humanized forms of the murine 3D6 antibody including 7 exemplified humanized heavy chain mature variable regions (hu3D6VHvb1 (SEQ ID NO:76), hu3D6VHvb2 (SEQ ID NO:77), hu3D6VHvb3 (SEQ ID NO:78), hu3D6VHvb4 (SEQ ID NO:79), hu3D6VHvb5 (SEQ ID NO:80), hu3D6VHvb6 (SEQ ID NO:90), and hu3D6VHvb7 (SEQ ID NO:91)) and 3 exemplified humanized light chain mature variable regions (hu3D6VLvb1 (SEQ ID NO:83), hu3D6VLvb2 (SEQ ID NO:84), and hu3D6VLvb3 (SEQ ID NO:85)).

In an embodiment, humanized sequences are generated using a two-stage PCR protocol that allows introduction of multiple mutations, deletions, and insertions using QuikChange site-directed mutagenesis [Wang, W. and Malcolm, B. A. (1999) BioTechniques 26:680-682)].

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, *J. Mol. Biol.* 196:901-917 (1987); Thornton & Martin, *J. Mol. Biol.* 263:800-815 (1996)). Framework residues that support antigen-binding loop conformations and play a role in fine-tuning the fit of an antibody to antigen are sometimes referred to as vernier residues (Foote & Winter, *J. Mol. Biol* 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Other framework residues that are candidates for substitution are N-terminal glutamine residues (Q) that may be replaced with glutamic acid (E) to minimize potential for pyroglutamate conversion [Y. Diana Liu, et al., 2011, J. Biol. Chem., 286: 11211-11217]. Glutamic acid (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control.

Exemplary humanized antibodies are humanized forms of the mouse 3D6, designated Hu3D6.

The mouse antibody 3D6 comprises mature heavy and light chain variable regions having amino acid sequences comprising SEQ ID NO:7 and SEQ ID NO:11, respectively. The invention provides 7 exemplified humanized mature heavy chain variable regions: hu3D6VHvb1, hu3D6VHvb2, hu3D6VHvb3, hu3D6VHvb4, hu3D6VHvb5, hu3D6VHvb6, and hu3D6VHvb7. The invention further provides 3 exemplified mature light chain variable regions hu3D6VLvb1, hu3D6VLvb2, and hu3D6VLvb3. FIGS. 1 and 2 show alignments of the heavy chain variable region and light chain variable region, respectively, of murine 3D6 and various humanized antibodies.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 31 variable region framework positions were considered as candidates for substitutions in the 3 exemplified human mature light chain variable regions and the 7 exemplified human mature heavy chain variable regions, as further specified in the examples: L7 (T7S, from germ line), L10 (T10S, from germ line), L15 (I15L, from germ line), L17 (Q17E, to enhance stability), L37 (L37Q, from germ line), L45 (K45R, from germ line), L83 (L83V, from germ line), L86 (H86Y, from mouse 3D6), L100 (A100Q, from germ line), L106 (L1061, from germ line), H1 (Q1E, from mouse 3D6), H5 (Q5V, from germ line), H11 (L11V, from germ line), H17 (S17T, from germ line), H20 (L20I, from germ line), H23 (T23K, from germ line), H38 (K38R, from mouse 3D6), H42 (E42G, from germ line), H43 (Q43K, from germ line), H66 (K66R, from germ line), H67 (A67V, from germ line), H75 (S75T, from germ line, H76 (N76D, from germ line), H80 (L80M, from germ line), H81 (Q81E, from germ line), H83 (T83R, from germ line), H91 (Y91F, from mouse 3D6), H93 (A93S, from mouse 3D6), H94 (S94T, from mouse 3D6), H108 (T108L, from germ line), and H109 (L109V, from germ line). Here and elsewhere in describing substitutions, comments in parentheses indicate one rationale for a substitution. Some substitutions have multiple rationales. The following 5 variable region CDR positions were considered as candidates for substitutions in the 3 exemplified human mature light chain variable regions and 7 exemplified human mature heavy chain variable regions, as further specified in the examples: L24 (K24R, from germ line), H28 (N28T, from germ line), H54 (N54D, from germ line), H56 (D56E, from germline), and H58 (V58I, from germ line). In some humanized 3D6 antibodies, Kabat CDR-H2 has an amino acid sequence comprising SEQ ID NO:87. In some humanized 3D6 antibodies, Kabat-Chothia Composite CDR-H1 has an amino acid sequence comprising SEQ ID NO:86, and Kabat CDR-H2 has an amino acid sequence comprising SEQ ID NO:87. In some humanized 3D6 antibodies, Kabat-Chothia Composite CDR-H1 has an amino acid sequence comprising SEQ ID NO:86 and Kabat CDR-H2 has an amino acid sequence comprising SEQ ID NO:88. In some humanized 3D6 antibodies, Kabat-Chothia Composite CDR-H1 has an amino acid sequence comprising SEQ ID NO:86 and Kabat CDR-H2 has an amino acid sequence comprising SEQ ID NO:92. In some humanized 3D6 antibodies, Kabat CDR-L1 has an amino acid sequence comprising SEQ ID NO:89.

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions VHvb1/VLvb1, VHvb1/VLvb2, VHvb1/VLvb3, VHvb2/VLvb1, VHvb2/VLvb2, VHvb2/VLvb3, VHvb3/VLvb1, VHvb3/VLvb2, VHvb3/VLvb3, VHvb4/VLvb1, VHvb4/VLvb2, VHvb4/VLvb3, VHvb5/VLvb1, VHvb5/VLvb2, VHvb5/VLvb3, VHvb6/VLvb1, VHvb6/VLvb2, VHvb6/VLvb3, VHvb7/VLvb1, VHvb7/VLvb2, VHvb7/VLvb3.

Exemplified antibodies include any permutations or combinations of the exemplified mature heavy chain variable regions hu3D6VHvb1 (SEQ ID NO:76), hu3D6VHvb2 (SEQ ID NO:77), hu3D6VHvb3 (SEQ ID NO:78), hu3D6VHvb4 (SEQ ID NO:79), hu3D6Hvb5 (SEQ ID NO:80), hu3D6VHvb6 (SEQ ID NO:90), and hu3D6VHvb7 (SEQ ID NO:91) with any of the humanized 3D6VL light chain variable regions hu3D6VLv1 (SEQ ID NO:20), hu3D6VLv2 (SEQ ID NO:21), hu3D6VLv3 (SEQ ID NO:22), and hu3D6VLv4 (SEQ ID NO:22). Exemplified antibodies include any permutations or combinations of the exemplified mature light chain variable regions hu3D6VLvb1 (SEQ ID NO:83), hu3D6VLvb2 (SEQ ID NO:84), or hu3D6VLvb3 (SEQ ID NO:85) with any of the humanized 3D6V6 heavy chain variable regions hu3D6VHv1 (SEQ ID NO:15); hu3D6VHv2 (SEQ ID NO:16); hu3D6VHv1b (SEQ ID NO:17); hu3D6VHv1bA11 (SEQ ID NO:18); hu3D6VHv5 (SEQ ID NO:19); hu3D6VHv1bA11B6G2 (SEQ ID NO:46); hu3D6VHv1bA11B6H3 (SEQ ID NO:47); hu3D6VHv1c (SEQ ID NO:48); hu3D6VHv1d (SEQ ID NO:49); hu3D6VHv1e (SEQ ID NO:50); hu3D6VHv1f (SEQ ID NO:51); hu3D6VHv3 (SEQ ID NO:52); hu3D6VHv3b (SEQ ID NO:53); hu3D6VHv3c (SEQ ID NO:54); hu3D6VHv4 (SEQ ID NO:55); hu3D6VHv4b (SEQ ID NO:56); and hu3D6VHv4c (SEQ ID NO:57).

The invention provides variants of the 3D6 humanized antibody in which the humanized mature heavy chain variable region shows at least 90%, 95%, 96%, 97%, 98%, or 99% identity to hu3D6VHvb1 (SEQ ID NO:76), hu3D6VHvb2 (SEQ ID NO:77), hu3D6VHvb3 (SEQ ID NO:78), hu3D6VHvb4 (SEQ ID NO:79), hu3D6Hvb5 (SEQ ID NO:80), hu3D6VHvb6 (SEQ ID NO:90), or hu3D6VHvb7 (SEQ ID NO:91) and the humanized mature light chain variable region shows at least 90%, 95%, 96%, 97%, 98%, or 99% identity to hu3D6VLvb1 (SEQ ID NO:83), hu3D6VLvb2 (SEQ ID NO:84), or hu3D6VLvb3 (SEQ ID NO:85). In some such antibodies at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36 of the backmutations or other mutations in SEQ ID NOs:76-80, SEQ ID NOs:90-91, and SEQ ID NOs:83-85) are retained. Some such humanized antibodies contain the same set of backmutations or other mutations as in the exemplified sequences defining sequence identity.

Thus for example, the invention includes humanized antibodies having a mature heavy chain variable region with at least 90%, 95%, 96%, 97%, 98%, 99% or 100% sequence identity to the mature heavy chain variable region of SEQ ID NO:77, and the same set of mutations as listed in Table 6 of SEQ ID NO:77, and three CDRs of SEQ ID NO:77, and a mature light chain region with at least 90%, 95%, 96%, 97%, 98%, 99% or 100% sequence identity to SEQ ID 84 or 85, and the same set of mutations as listed in Table 7 for SEQ ID NO:84 or 85 respectively, and three CDRs of SEQ ID NO:84 or 85 respectively. Some antibodies comprise a mature heavy chain variable region of SEQ ID NO:77 and a mature light chain variable region of SEQ ID NO:84 or 85.

The invention also includes humanized antibodies having a mature heavy chain variable region with at least 90%, 95%, 96%, 97%, 98%, 99% or 100% sequence identity to the mature heavy chain variable region of SEQ ID NO:90, and the same set of mutations as listed in Table 6 for SEQ ID NO:90, and three CDRs of SEQ ID NO:90, and a mature light chain region with at least 90%, 95%, 96%, 97%, 98%, 99% or 100% sequence identity to SEQ ID NO:84 or 85, and the same set of mutations as listed in Table 7 for SEQ ID NO:84 or 85 respectively, and three CDRs of SEQ ID NO:84 or 85 respectively. Some antibodies comprise a mature heavy chain variable region of SEQ ID NO:90 and a mature light chain variable region of SEQ ID NO:84 or 85.

In some humanized 3D6 antibodies, at least one of the following positions in the VH region is occupied by the amino acid as specified: H93 is occupied by S and H94 is occupied by T. In some humanized 3D6 antibodies, positions H93 and H94 (Vernier residues) are occupied by S and T, respectively, as is the case in, e.g., huVHvb1, huVHvb2, huVHvb3, huVHvb4, huVHvb5, huVHvb6, and huVHvb7.

In some humanized 3D6 antibodies, position H91 (interface residue) in the VH region is occupied by F, as is the case in, e.g., huVHvb1, huVHvb2, and huVHvb6.

In some humanized 3D6 antibodies, at least one of the following positions in the VH region is occupied by the amino acid as specified: H1 is occupied by E, H5 is occupied by V, H11 is occupied by V, H20 is occupied I, H23 is occupied by K, H38 is occupied by R, H42 is occupied by G, H43 is occupied by K, H66 is occupied by R, H75 is occupied by T, H76 is occupied by D, H81 is occupied by E, H108 is occupied by L, H109 is occupied by V. In some humanized 3D6 antibodies, positions H1, H5, H11, H20, H23, H38, H42, H43, H66, H75, H76, H81, H108, and H109 in the VH region are occupied by E, V, V, I, K, R, G, K, R, T, D, E, L, and V, respectively, as is the case in, e.g., huVHvb2, huVHvb3, huVHvb4, huVHvb5, huVHvb6, and huVHvb7.

In some humanized 3D6 antibodies, at least one of the following positions in the VH region is occupied by the amino acid as specified: H17 is occupied by T, H80 is occupied by M, H83 is occupied by R. In some humanized 3D6 antibodies, positions H17, H80, and H83 in the VH region are occupied by T, M, and R, respectively, as is the case in, e.g., huVHvb3, huVHvb4, huVHvb5, huVHvb6, and huVHvb7.

In some humanized 3D6 antibodies, position H58 (CDR-H2 residue) in the VH region is occupied by I, as is the case in, e.g., huVHvb3, huVHvb4, and huVHvb5.

In some humanized 3D6 antibodies, at least one of the following positions in the VH region is occupied by the amino acid as specified: H28 is occupied by T, H67 is occupied by V. In some humanized 3D6 antibodies, positions H28 and H67 in the VH region are occupied by T and V, respectively, as is the case in e.g., in huVHvb4, huVHvb5, huVHvb6, and huVHvb7.

In some humanized 3D6 antibodies, at least one of the following positions in the VH region is occupied by the amino acid as specified: H54 is occupied by D, H56 is occupied by E. In some humanized 3D6 antibodies, positions H54 and H56 (CDR-H2 residues) in the VH region are occupied by D and E, respectively, as is the case in, e.g., huVHvb6 and huVHvh7.

In some humanized 3D6 antibodies, at least one of the following positions in the VH region is occupied by the amino acid as specified: H1 is occupied by Q or E, H5 is occupied by Q or V, H11 is occupied by L or V, H17 is occupied by S or T, H20 is occupied by L or I, H23 is occupied by T or K, H28 is occupied by N or T, H38 is occupied by K or R, H42 is occupied by E or G, H43 is occupied by Q or K, H54 is occupied by N or D, H56 is occupied by D or E, H58 is occupied by V or I, H66 is occupied by K or R, H67 is occupied by A or V, H75 is occupied by S or T, H76 is occupied by N or D, H80 is occupied by L or M, H81 is occupied by Q or E, H83 is occupied by T or R, H91 is occupied by F or Y, H93 is occupied by S, H94 is occupied by T, H108 is occupied by T or L, H109 is occupied by L or V.

In some humanized 3D6 antibodies, positions H91, H93, and H94 in the VH region are occupied by F, S, and T, respectively, as in huVHvb1. In some humanized 3D6 antibodies, positions H1, H5, H11, H20, H23, H38, H42, H43, H66, H75, H76, H81, H91, H93, H94, H108, and H109 in the VH region are occupied by E, V, V, I, K, R, G, K, R, T, D, E, F, S, T, L, and V, respectively, as in huVHvb2. In some humanized 3D6 antibodies, positions H1, H5, H11, H17, H20, H23, H38, H42, H43, H58, H66, H75, H76, H80, H81, H83, H93, H94, H108, and H109 in the VH region are occupied by E, V, V, T, I, K, R, G, K, I, R, T, D, M, E, R, S, T, L, and V, respectively, as in huVHvb3. In some humanized 3D6 antibodies, positions H1, H5, H11, H17, H20, H23, H28, H38, H42, H43, H58, H66, H67, H75, H76, H80, H81, H83, H93, H94, H108, and H109 in the VH region are occupied by E, V, V, T, I, K, T, R, G, K, I, R, V, T, D, M, E, R, S, T, L, and V, respectively, as in huVHvb4. In some humanized 3D6 antibodies, positions H1, H5, H11, H17, H20, H23, H28, H38, H42, H43, H54, H56, H58, H66, H67, H75, H76, H80, H81, H83, H93, H94, H108, and H109 in the VH region are occupied by E, V, V, T, I, K, T, R, G, K, D, E, I, R, V, T, D, M, E, R, S, T, L, and V, respectively, as in huVHvb5. In some humanized 3D6 antibodies, positions H1, H5, H11, H17, H20, H23, H28, H38, H42, H43, H54, H56, H66, H67, H75, H76, H80, H81, H83, H91, H93, H94, H108, and H109 in the VH region are occupied by E, V, V, T, I, K, T, R, G, K, D, E, R, V, T, D, M, E, R, F, S, T, L, and V, respectively, as in huVHvb6. In some humanized 3D6 antibodies, positions H1, H5, H11, H17, H20, H23, H28, H38, H42, H43, H54, H56, H66, H67, H75, H76, H80, H81, H83, H93, H94, H108, and H109 in the VH region are occupied by E, V, V, T, I, K, T, R, G, K, D, E, R, V, T, D, M, E, R, S, T, L, and V, respectively, as in huVHvb7.

In some humanized 3D6 antibodies, at least one of the following positions in the VL region is occupied by the amino acid as specified: L7 is occupied by S, L10 is occupied by S, L15 is occupied by L, L83 is occupied by V, L86 is occupied by Y, and L106 is occupied by I. In some humanized 3D6 antibodies, positions L7, L10, L15, L83, L86, and L106 are occupied by S, S, L, V, Y, and Y, respectively, as is the case in, e.g., huVHvb2 and huVLvb3.

In some humanized 3D6 antibodies, at least one of the following positions in the VL region is occupied by the amino acid as specified: L7 is T or S, L10 is T or S, L15 is I or L, L17 is Q or E, L24 is K or R, L37 is L or Q, L45 is K or R, L83 is L or V, L86 is H or Y, L100 is A or Q, L106 is L or I.

In some humanized 3D6 antibodies, positions L7, L10, L15, L83, L86, and L106 in the VL region are occupied by S, S, L, V, Y, and I, respectively, as in huVLvb2. In some humanized 3D6 antibodies, positions L7, L10, L15, L17, L24, L37, L45, L83, L86, L100, and L106 in the VL region are occupied by S, S, L, E, R, Q, R, V, Y, Q, and I, respectively, as in huVLvb3.

In some humanized 3D6 antibodies, the variable heavy chain has ≥85% identity to human sequence. In some humanized 3D6 antibodies, the variable light chain has ≥85% identity to human sequence. In some humanized 3D6 antibodies, each of the variable heavy chain and variable light chain has ≥85% identity to human germline sequence. In some humanized 3D6 antibodies, the three heavy chain CDRs are as defined by Kabat/Chothia Composite (SEQ ID NOs:8, 9, and a sequence of LDF) and the three light chain CDRs are as defined by Kabat/Chothia Composite (SEQ ID NOs:12, 13, and 14); provided that position H28 is occupied by N or T, position H54 is occupied by N or D, position H56 is occupied by D or E, position H58 is occupied by V or I, and position L24 is occupied by K or R. In some humanized 3D6 antibodies, Kabat/Chothia Composite CDR-H1 has an amino acid sequence comprising SEQ ID NO:86. In some humanized 3D6 antibodies, Kabat CDR-H2 has an amino acid sequence comprising SEQ ID NO:87, SEQ ID NO:88, or SEQ ID NO:92. In some humanized 3D6 antibodies, Kabat CDR-L1 has an amino acid sequence comprising SEQ ID NO:89.

The CDR regions of such humanized antibodies can be identical or substantially identical to the CDR regions of 3D6, The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu3D6 heavy and light chains by a small number (e.g., typically no more than 1, 2, 3, 5, 10, or 15) of replacements, deletions or insertions. Such differences are usually in the framework but can also occur in the CDRs.

A possibility for additional variation in humanized 3D6 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 3D6 variants (whether or not conservative) have no substantial effect on the binding affinity or potency of the humanized mAb, that is, its ability to bind to tau.

The humanized 3D6 antibodies are further characterized by their ability to bind both phosphorylated and unphosphorylated tau and misfolded/aggregated forms of tau. Some humanized antibodies are characterized by binding to human tau or possession of other functional property, such as inhibition of tau binding to neuronal cells or disaggregation of tau, the same as or more strongly than mouse 3D6 (e.g., up to 2×, 5×, 10× or 20×) that of mouse 3D6. Such properties can be compared by any of the assays described in the examples.

C. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. Numbering conventions for constant regions include EU numbering (Edelman, G. M. et al., Proc. Natl. Acad. USA, 63, 78-85 (1969)), Kabat numbering (Kabat, *Sequences of Proteins of Immunological Interest* (National Institutes of Health, Bethesda, MD, 1991, IMGT unique numbering (Lefranc M.-P. et al., IMGT unique numbering for immunoglobulin and T cell receptor constant domains and Ig superfamily C-like domains, Dev. Comp. Immunol., 29, 185-203 (2005), and IMGT exon numbering (Lefranc, supra).

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine. In some antibodies, the isotype is human IgG2 or IgG4.

An exemplary human light chain kappa constant region has the amino acid sequence of SEQ ID NO: 104 (with or without the N-terminal arginine). An exemplary human IgG1 heavy chain constant region has the amino acid sequence of SEQ ID NO: 103 (with or without the C-terminal lysine). Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 with or without the C-terminal lysine. Reference to a human constant region includes a constant region with any natural allotype or any permutation of residues occupying positions in natural allotypes.

D. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NO:105, which encodes a human IgG1 constant region (SEQ ID NO:103), and SEQ ID NO:106, which encodes a human kappa light chain constant region (SEQ ID NO:104).

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809). Antibodies can also be administered in the form of nucleic acids encoding the antibody heavy and/or light chains. If both heavy and light chains are present, the chains are preferably linked as a single chain antibody. Antibodies for passive administration can also be prepared e.g., by affinity chromatography from sera of patients treated with peptide immunogens.

The DNA can be delivered in naked form (i.e., without colloidal or encapsulating materials). Alternatively a number of viral vector systems can be used including retroviral systems (see, e.g., Lawrie and Tumin, Cur. Opin. Genet. Develop. 3, 102-109 (1993)) including retrovirus derived vectors such MMLV, HIV-1, and ALV; adenoviral vectors {see, e.g., Bett et al, J. Virol. 67, 591 1 (1993)); adeno-associated virus vectors {see, e.g., Zhou et al., J. Exp. Med. 179, 1867 (1994)), lentiviral vectors such as those based on HIV or FIV gag sequences, viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al, WO 94/12629 and Xiao & Brandsma, Nucleic Acids. Res. 24, 2630-2622 (1996)).

DNA encoding an immunogen, or encoding the antibody heavy and/or light chains, or a vector containing the same, can be packaged into liposomes. Suitable lipids and related analogs are described by U.S. Pat. Nos. 5,208,036, 5,264, 618, 5,279,833, and 5,283,185. Vectors and DNA encoding an immunogen, or encoding the antibody heavy and/or light chains can also be adsorbed to or associated with particulate carriers, examples of which include polymethyl methacrylate polymers and polylactides and poly(lactide-co-glycolides), (see, e.g., McGee et al., J. Micro Encap. 1996).

Vectors or segments therefrom encoding the antibody heavy and/or light chains can be incorporated in cells ex vivo, for example to cells explanted from an individual patient (e.g., lymphocytes, bone marrow aspirates, tissue biopsy) or universal donor hematopoietic stem cells, followed by reimplantation of the cells into a patient, usually after selection for cells which have incorporated the transgenes. (see, e.g., WO 2017/091512). Exemplary patient-derived cells include patient derived induced pluripotent stem cells (iPSCs) or other types of stem cells (embryonic, hematopoietic, neural, or mesenchymal).

A vector or segment therefrom encoding the antibody heavy and/or light chains can be introduced into any region of interest in cells ex vivo, such as an albumin gene or other safe harbor gene. Cells incorporating the vector can be implanted with or without prior differentiation Cells can be implanted into a specific tissue, such as a secretory tissue or a location of pathology, or systemically, such as by infusion into the blood. For example, cells can be implanted into a secretory tissue of a patient, such as the liver, optionally with prior differentiation to cells present in that tissue, such as hepatocytes in the case of a liver. Expression of the antibody in the liver results in secretion of the antibody to the blood.

E. Antibody Screening Assays

Antibodies can be initially screened for the intended binding specificity as described above. Active immunogens can likewise be screened for capacity to induce antibodies with such binding specificity. In this case, an active immunogen is used to immunize a laboratory animal and the resulting sera tested for the appropriate binding specificity.

Antibodies having the desired binding specificity can then be tested in cellular and animal models. The cells used for such screening are preferentially neuronal cells. A cellular model of tau pathology has been reported in which neuroblastoma cells are transfected with a four-repeat domain of tau, optionally with a mutation associated with tau pathology (e.g., delta K280, see Khlistunova, Current Alzheimer Research 4, 544-546 (2007)). In another model, tau is induced in the neuroblastoma N2a cell line by the addition of doxycyclin. The cell models enable one to study the toxicity of tau to cells in the soluble or aggregated state, the appearance of tau aggregates after switching on tau gene expression, the dissolution of tau aggregates after switching the gene expression off again, and the efficiency of antibodies in inhibiting formation of tau aggregates or disaggregating them.

Antibodies can also be screened in transgenic animal models of diseases associated with tau. Such transgenic animals can include a tau transgene (e.g., any of the human isoforms) and optionally a human APP transgene among others, such as a kinase that phosphorylates tau, ApoE, presenilin or alpha synuclein. Such transgenic animals are disposed to develop at least one sign or symptom of a disease associated with tau.

An exemplary transgenic animal is the K3 line of mice (Itner et al., Proc. Natl. Acad. Sci. USA 105(41):15997-6002 (2008)). These mice have a human tau transgene with a K 369 I mutation (the mutation is associated with Pick's disease) and a Thy 1.2 promoter. This model shows a rapid course of neurodegeneration, motor deficit and degeneration of afferent fibers and cerebellar granule cells. Another exemplary animal is the JNPL3 line of mice. These mice have a human tau transgene with a P301L mutation (the mutation is associated with frontotemporal dementia) and a Thy 1.2 promoter (Taconic, Germantown, N.Y., Lewis, et al., Nat Genet. 25:402-405 (2000)). These mice have a more gradual course of neurodegeneration. The mice develop neurofibrillary tangles in several brain regions and spinal cord, which is hereby incorporated by reference in its entirety). This is an excellent model to study the consequences of tangle development and for screening therapy that may inhibit the generation of these aggregates. Another advantage of these animals is the relatively early onset of pathology. In the homozygous line, behavioral abnormalities associated with tau pathology can be observed at least as early as 3 months, but the animals remain relatively healthy at least until 8 months of age. In other words, at 8 months, the animals ambulate, feed themselves, and can perform the behavioral tasks sufficiently well to allow the treatment effect to be monitored. Active immunization of these mice for 6-13 months with—AI wI KLH-PHF-1 generated titers of about 1,000 and showed fewer neurofibrillary tangles, less pSer422, and reduced weight loss relative to untreated control mice.

The activity of antibodies can be assessed by various criteria including reduction in amount of total tau or phosphorylated tau, reduction in other pathological characteristics, such as amyloid deposits of Aβ, and inhibition or delay or behavioral deficits. Antibodies can be tested for passage of antibodies across the blood brain barrier into the brain of a transgenic animal. Antibodies or fragments inducing an antibody can also be tested in non-human primates that naturally or through induction develop symptoms of diseases characterized by tau. Tests on an antibody are usually performed in conjunction with a control in which a parallel experiment is conduct except that the antibody or active agent is absent (e.g., replaced by vehicle). Reduction, delay or inhibition of signs or symptoms disease attributable to an antibody or active agent under test can then be assessed relative to the control.

IV. Patients Amenable to Treatment

The presence of neurofibrillary tangles has been found in several diseases including Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), and progressive supranuclear palsy (PSP). The present regimes can also be used in treatment or prophylaxis of any of these diseases. Because of the widespread association between neurological diseases and conditions and tau, the present regimes can be used in treatment or prophylaxis of any subject showing elevated levels of tau or phosphorylated tau (e.g., in the CSF) compared with a mean value in individuals without neurological disease. The present regimes can also be used in treatment or prophylaxis of neurological disease in individuals having a mutation in tau associated with neurological disease. The present methods are particularly suitable for treatment or prophylaxis of Alzheimer's disease, and especially in patients.

Patients amenable to treatment include individuals at risk of disease but not showing symptoms, as well as patients presently showing symptoms. Patients at risk of disease include those having a known genetic risk of disease. Such individuals include those having relatives who have experienced this disease, and those whose risk is determined by analysis of genetic or biochemical markers. Genetic markers of risk include mutations in tau, such as those discussed above, as well as mutations in other genes associated with neurological disease. For example, the ApoE4 allele in heterozygous and even more so in homozygous form is associated with risk of Alzheimer's disease. Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of AD, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF tau or phospho-tau and Aβ42 levels. Elevated tau or phospho-tau and decreased Aβ42 levels signify the presence of AD. Some mutations associated with Parkinson's disease. Ala30Pro or Ala53, or mutations in other genes associated with Parkinson's disease such as leucine-rich repeat kinase, PARK8. Individuals can also be diagnosed with any of the neurological diseases mentioned above by the criteria of the DSM IV TR.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

V. Nucleic Acids

The invention further provides nucleic acids encoding any of the heavy and light chains described above (e.g., SEQ ID NO:7, SEQ ID NO:11, SEQ ID NOs:76-80, SEQ ID NOs: 90-91, and SEQ ID NOs:83-85). Exemplary nucleic acids include SEQ ID NOs: 30-31, 93-99, 100-102, and 105-106. Optionally, such nucleic acids further encode a signal peptide and can be expressed with the signal peptide linked to the heavy chain variable region or to the light chain variable region. Coding sequences of nucleic acids can be operably linked with regulatory sequences to ensure expression of the coding sequences, such as a promoter, enhancer, ribosome binding site, transcription termination signal, and the like. The regulatory sequences can include a promoter, for example, a prokaryotic promoter or a eukaryotic promoter. The nucleic acids encoding heavy or light chains can be codon-optimized for expression in a host cell. The nucleic acids encoding heavy and light chains can encode a selectable gene. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

VI. Conjugated Antibodies

Conjugated antibodies that specifically bind to antigens, such as tau, are useful in detecting the presence of tau; monitoring and evaluating the efficacy of therapeutic agents being used to treat patients diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP); inhibiting or reducing aggregation of tau; inhibiting or reducing tau fibril formation; reducing or clearing tau deposits; stabilizing non-toxic conformations of tau; or treating or effecting prophylaxis of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) in a patient. For example, such antibodies can be conjugated with other therapeutic moieties, other proteins, other antibodies, and/or detectable labels. See WO 03/057838; U.S. Pat. No. 8,455,622. Such therapeutic moieties can be any agent that can be used to treat, combat, ameliorate, prevent, or improve an unwanted condition or disease in a patient, such as Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

Conjugated therapeutic moieties can include cytotoxic agents, cytostatic agents, neurotrophic agents, neuroprotective agents, radiotherapeutic agents, immunomodulators, or any biologically active agents that facilitate or enhance the activity of the antibody. A cytotoxic agent can be any agent that is toxic to a cell. A cytostatic agent can be any agent that inhibits cell proliferation. A neurotrophic agent can be any agent, including chemical or proteinaceous agents, that promotes neuron maintenance, growth, or differentiation. A neuroprotective agent can be agent, including chemical or proteinaceous agents, that protects neurons from acute insult or degenerative processes. An immunomodulator can be any agent that stimulates or inhibits the development or maintenance of an immunologic response. A radiotherapeutic agent can be any molecule or compound that emits radiation. If such therapeutic moieties are coupled to a tau-specific antibody, such as the antibodies described herein, the coupled therapeutic moieties will have a specific affinity for tau-related disease-affected cells over normal cells. Consequently, administration of the conjugated antibodies directly targets cancer cells with minimal damage to surrounding normal, healthy tissue. This can be particularly useful for therapeutic moieties that are too toxic to be administered on their own. In addition, smaller quantities of the therapeutic moieties can be used.

Some such antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio)propionate for ricin. See Pietersz et al., *Cancer Res.* 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., Leukemia 18:1215-1222 (2004).

Some such antibodies can be linked to radioisotopes. Examples of radioisotopes include, for example, yttrium$^{90}$ (90Y), indium$^{111}$ (111In), $^{131}$I, $^{99}$mTc, radiosilver-111, radiosilver-199, and Bismuth$^{213}$. Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.,* 48 Suppl 1:S91-S95 (2001).

Some such antibodies can be linked to other therapeutic moieties. Such therapeutic moieties can be, for example, cytotoxic, cytostatic, neurotrophic, or neuroprotective. For example, antibodies can be conjugated with toxic chemotherapeutic drugs such as maytansine, geldanamycin, tubulin inhibitors such as tubulin binding agents (e.g., auristatins), or minor groove binding agents such as calicheamicin. Other representative therapeutic moieties include agents known to be useful for treatment, management, or amelioration of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., MAbs. 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within tau or can bind to a different target antigen.

Antibodies can also be coupled with a detectable label. Such antibodies can be used, for example, for diagnosing Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP), and/or for assessing efficacy of treatment. Such antibodies are particularly useful for performing such determinations in subjects having or being susceptible to Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP), or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I,) carbon ($^{14}$C), sulfur ($^{5}$S), tritium (3H), indium ($^{115}$In, $^{113}$In, $^{112}$In $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Ph, $^{97}$Ru, $^{68}$Ge, $^{57}$Co, $^{65}$Zn, $^{85}$Sr, $^{32}$P, $^{153}$Gd, $^{169}$Yb $^{51}$Cr, $^{54}$Mn, $^{75}$Se, $^{113}$Sn, and $^{117}$Tin; positron emitting metals using various positron emission tomographies; nonradioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.,* 48 Suppl 1:S91-S95 (2001).

Therapeutic moieties, other proteins, other antibodies, and/or detectable labels may be coupled or conjugated, directly or indirectly through an intermediate (e.g., a linker), to an antibody of the invention. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., Immunol. Rev., 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

VII. Pharmaceutical Compositions and Methods of Use

In prophylactic applications, an antibody or a pharmaceutical composition the same is administered to a patient susceptible to, or otherwise at risk of a disease (e.g., Alzheimer's disease) in regime (dose, frequency and route of administration) effective to reduce the risk, lessen the severity, or delay the onset of at least one sign or symptom of the disease. In particular, the regime is preferably effective to inhibit or delay tau or phospho-tau and paired filaments formed from it in the brain, and/or inhibit or delay its toxic effects and/or inhibit/or delay development of behavioral deficits. In therapeutic applications, an antibody is administered to a patient suspected of, or already suffering from a disease (e.g., Alzheimer's disease) in a regime (dose, frequency and route of administration) effective to ameliorate or at least inhibit further deterioration of at least one sign or symptom of the disease. In particular, the regime is preferably effective to reduce or at least inhibit further increase of levels of tau, phosphor-tau, or paired filaments formed from it, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses of vary depending on many different factors, such as means of administration, target site, physiological state of the patient, whether the patient is an ApoE carrier, whether the patient is human or an animal, other medications administered, and whether treatment is prophylactic or therapeutic.

Exemplary dosage ranges for antibodies are from about 0.01 to 60 mg/kg, or from about 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

Antibodies are preferably administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal, intraocular, or intramuscular. Preferred routes for administration of antibodies are intravenous and subcutaneous. Preferred routes for active immunization are subcutaneous and intramuscular. This type of injection is most typically performed in the arm or leg muscles. In some methods, agents are injected directly into a particular tissue where deposits have accumulated, for example intracranial injection.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Alzheimer's disease, the present regimes can be combined with immunotherapy against A3 (WO/2000/072880), cholinesterase inhibitors or memantine or in the case of Parkinson's disease immunotherapy against alpha synuclein WO/2008/103472, Levodopa, dopamine agonists, COMT inhibitors, MAO-B inhibitors, Amantadine, or anticholinergic agents.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-60 mg/kg (e.g., 0.5, 3, 10, 30, or 60 mg/kg), or 0.5-5 mg/kg body weight (e.g., 0.5, 1, 2, 3, 4 or 5 mg/kg) or 10-4000 mg or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

A. Diagnostics and Monitoring Methods

In Vivo Imaging, Diagnostic Methods, and Optimizing Immunotherapy

The invention provides methods of in vivo imaging tau protein deposits (e.g., neurofibrillary tangles and tau inclusions) in a patient. The methods work by administering a humanized antibody of the invention to the patient and then detecting the antibody after it has bound. A clearing response to the administered antibodies can be avoided or reduced by using antibody fragments lacking a full-length constant region, such as Fabs. In some methods, the same antibody can serve as both a treatment and diagnostic reagent.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for tau is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using positron emission tomography (PET) or single-photon emission computed tomography (SPECT).

The methods of in vivo imaging of tau protein deposits are useful to diagnose or confirm diagnosis of a tauopathy, such as Alzheimer's disease, frontotemporal lobar degeneration, progressive supranuclear palsy and Pick's disease, or susceptibility to such a disease. For example, the methods can be used on a patient presenting with symptoms of dementia. If the patient has abnormal neurofibrillary tangles, then the patient is likely suffering from Alzheimer's disease. Alternatively, if the patient has abnormal tau inclusions, then depending on the location of the inclusions, the patient may be suffering from frontotemporal lobar degeneration. The methods can also be used on asymptomatic patients. Presence of abnormal tau protein deposits indicates susceptibility to future symptomatic disease. The methods are also useful for monitoring disease progression and/or response to treatment in patients who have been previously diagnosed with a tau-related disease.

Diagnosis can be performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning tau immunotherapy treatment, and measured values thereafter compared with the baseline values. A decrease in values relative to baseline signals a positive response to treatment.

In some patients, diagnosis of a tauopathy may be aided by performing a PET scan. A PET scan can be performed using, for example, a conventional PET imager and auxiliary equipment. The scan typically includes one or more regions of the brain known in general to be associated with tau protein deposits and one or more regions in which few if any deposits are generally present to serve as controls.

The signal detected in a PET scan can be represented as a multidimensional image. The multidimensional image can be in two dimensions representing a cross-section through the brain, in three dimensions, representing the three dimensional brain, or in four dimensions representing changes in the three dimensional brain over time. A color scale can be used with different colors indicating different amounts of label and, inferentially, tau protein deposit detected. The results of the scan can also be presented numerically, with numbers relating to the amount of label detected and consequently amount of tau protein deposits. The label present in a region of the brain known to be associated with deposits for a particular tauopathy (e.g., Alzheimer's disease) can be compared with the label present in a region known not to be associated with deposits to provide a ratio indicative of the extent of deposits within the former region. For the same radiolabeled ligand, such ratios provide a comparable measure of tau protein deposits and changes thereof between different patients.

In some methods, a PET scan is performed concurrent with or in the same patient visit as an MRI or CAT scan. An MRI or CAT scan provides more anatomical detail of the brain than a PET scan. However, the image from a PET scan can be superimposed on an MRI or CAT scan image more precisely indicating the location of PET ligand and inferentially tau deposits relative to anatomical structures in the brain. Some machines can perform both PET scanning and MRI or CAT scanning without the patient changing positions between the scans facilitating superimposition of images.

Suitable PET ligands include radiolabeled antibodies of the invention (e.g., a mouse, humanized, chimeric or veneered 3D6 antibody). The radioisotope used can be, for example, $C^{11}$, $N^{13}$, $O^{15}$, $F^{18}$, or $I^{123}$. The interval between administering the PET ligand and performing the scan can depend on the PET ligand and particularly its rate of uptake and clearing into the brain, and the half-life of its radiolabel.

PET scans can also be performed as a prophylactic measure in asymptomatic patients or in patients who have symptoms of mild cognitive impairment but have not yet been diagnosed with a tauopathy but are at elevated risk of developing a tauopathy. For asymptomatic patients, scans are particularly useful for individuals considered at elevated risk of tauopathy because of a family history, genetic or biochemical risk factors, or mature age. Prophylactic scans can commence for example, at a patient age between 45 and 75 years. In some patients, a first scan is performed at age 50 years.

Prophylactic scans can be performed at intervals of for example, between six months and ten years, preferably between 1-5 years. In some patients, prophylactic scans are performed annually. If a PET scan performed as a prophylactic measure indicates abnormally high levels of tau protein deposits, immunotherapy can be commenced and subsequent PET scans performed as in patients diagnosed with a tauopathy. If a PET scanned performed as a prophylactic measure indicates levels of tau protein deposits within normal levels, further PET scans can performed at intervals of between six months and 10 years, and preferably 1-5 years, as before, or in response to appearance of signs and symptoms of a tauopathy or mild cognitive impairment. By combining prophylactic scans with administration of tau-directed immunotherapy if and when an above normal level of tau protein deposits is detected, levels of tau protein deposits can be reduced to, or closer to, normal levels, or at least inhibited from increasing further, and the patient can remain free of the tauopathy for a longer period than if not receiving prophylactic scans and tau-directed immunotherapy (e.g., at least 5, 10, 15 or 20 years, or for the rest of the patient's life).

Normal levels of tau protein deposits can be determined by the amount of neurofibrillary tangles or tau inclusions in the brains of a representative sample of individuals in the general population who have not been diagnosed with a particular tauopathy (e.g., Alzheimer's disease) and are not considered at elevated risk of developing such disease (e.g., a representative sample of disease-free individuals under 50 years of age). Alternatively, a normal level can be recognized in an individual patient if the PET signal according to the present methods in a region of the brain in which tau protein deposits are known to develop is not different (within the accuracy of measurement) from the signal from a region of the brain in which it is known that such deposits do not normally develop. An elevated level in an individual can be recognized by comparison to the normal levels (e.g., outside mean and variance of a standard deviation) or simply from an elevated signal beyond experimental error in a region of the brain associated with tau protein deposits compared with a region not known to be associated with deposits. For purposes of comparing the levels of tau protein deposits in an individual and population, the tau protein deposits should preferably be determined in the same region(s) of the brain, these regions including at least one region in which tau protein deposits associated with a particular tauopathy (e.g., Alzheimer's disease) are known to form. A patient having an elevated level of tau protein deposits is a candidate for commencing immunotherapy.

After commencing immunotherapy, a decrease in the level of tau protein deposits can be first seen as an indication that the treatment is having the desired effect. The observed decrease can be, for example, in the range of 1-100%, 1-50%, or 1-25% of the baseline value. Such effects can be measured in one or more regions of the brain in which deposits are known to form or can be measured from an average of such regions. The total effect of treatment can be approximated by adding the percentage reduction relative to baseline to the increase in tau protein deposits that would otherwise occur in an average untreated patient.

Maintenance of tau protein deposits at an approximately constant level or even a small increase in tau protein deposits can also be an indication of response to treatment albeit a suboptimal response. Such responses can be compared with a time course of levels of tau protein deposits in patients with a particular tauopathy (e.g., Alzheimer's disease) that did not receive treatment, to determine whether the immunotherapy is having an effect in inhibiting further increases of tau protein deposits.

Monitoring of changes in tau protein deposits allows adjustment of the immunotherapy or other treatment regime in response to the treatment. PET monitoring provides an indication of the nature and extent of response to treatment. Then a determination can be made whether to adjust treatment and if desired treatment can be adjusted in response to the PET monitoring. PET monitoring thus allows for tau-directed immunotherapy or other treatment regime to be adjusted before other biomarkers, MRI or cognitive measures have detectably responded. A significant change means that comparison of the value of a parameter after treatment relative to basement provides some evidence that treatment has or has not resulted in a beneficial effect. In some instances, a change of values of a parameter in a patient itself provides evidence that treatment has or has not resulted in a beneficial effect. In other instances, the change of values, if any, in a patient, is compared with the change of values, if any, in a representative control population of patients not undergoing immunotherapy. A difference in response in a particular patient from the normal response in the control patient (e.g., mean plus variance of a standard deviation) can also provide evidence that an immunotherapy regime is or is not achieving a beneficial effect in a patient.

In some patients, monitoring indicates a detectable decline in tau protein deposits but that the level of tau protein deposits remains above normal. In such patients, if there are no unacceptable side effects, the treatment regime can be continued as is or even increased in frequency of administration and/or dose if not already at the maximum recommended dose.

If the monitoring indicates levels of tau protein deposits in a patient have already been reduced to normal, or near-normal, levels of tau protein deposits, the immunotherapy regime can be adjusted from one of induction (i.e., that reduces the level of tau protein deposits) to one of maintenance (i.e., that maintains tau protein deposits at an approximately constant level). Such a regime can be affected by reducing the dose and or frequency of administering immunotherapy.

In other patients, monitoring can indicate that immunotherapy is having some beneficial effect but a suboptimal effect. An optimal effect can be defined as a percentage reduction in the level of tau protein deposits within the top half or quartile of the change in tau protein deposits (measured or calculated over the whole brain or representative region(s) thereof in which tau protein deposits are known to form) experienced by a representative sample of tauopathy patients undergoing immunotherapy at a given time point after commencing therapy. A patient experiencing a smaller decline or a patient whose tau protein deposits remains constant or even increases, but to a lesser extent than expected in the absence of immunotherapy (e.g., as inferred from a control group of patients not administered immunotherapy) can be classified as experiencing a positive but suboptimal response. Such patients can optionally be subject to an adjustment of regime in which the dose and or frequency of administration of an agent is increased.

In some patients, tau protein deposits may increase in similar or greater fashion to tau deposits in patients not receiving immunotherapy. If such increases persist over a period of time, such as 18 months or 2 years, even after any increase in the frequency or dose of agents, immunotherapy can if desired be discontinued in favor of other treatments.

The foregoing description of diagnosing, monitoring, and adjusting treatment for tauopathies has been largely focused on using PET scans. However, any other technique for visualizing and/or measuring tau protein deposits that is amenable to the use of tau antibodies of the invention (e.g., a mouse, humanized, chimeric or veneered 3D6 antibody) can be used in place of PET scans to perform such methods.

Also provided are methods of detecting an immune response against tau in a patient suffering from or susceptible to diseases associated with tau. The methods can be used to monitor a course of therapeutic and prophylactic treatment with the agents provided herein. The antibody profile following passive immunization typically shows an immediate peak in antibody concentration followed by an exponential decay. Without a further dose, the decay approaches pretreatment levels within a period of days to months depending on the half-life of the antibody administered. For example, the half-life of some human antibodies is of the order of 20 days.

In some methods, a baseline measurement of antibody to tau in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

Also provided are methods of detecting tau in a subject, for example, by measuring tau in a sample from a subject or by in vivo imaging of tau in a subject. Such methods are useful to diagnose or confirm diagnosis of diseases associated with tau, or susceptibility thereto. The methods can also be used on asymptomatic subjects. The presence of tau indicates susceptibility to future symptomatic disease. The methods are also useful for monitoring disease progression and/or response to treatment in subjects who have been previously diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

Biological samples obtained from a subject having, suspected of having, or at risk of having Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) can be contacted with the antibodies disclosed herein to assess the presence of tau. For example, levels of tau in such subjects may be compared to those present in healthy subjects. Alternatively, levels of tau in such subjects receiving treatment for the disease may be compared to those of subjects who have not been treated for Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). Some such tests involve a biopsy of tissue obtained from such subjects. ELISA assays may also be useful methods, for example, for assessing tau in fluid samples.

VII. Kits

The invention further provides kits (e.g., containers) comprising an antibody disclosed herein and related materials, such as instructions for use (e.g., package insert). The instructions for use may contain, for example, instructions for administration of the antibody and optionally one or more additional agents. The containers of antibody may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

VIII. Other Applications

The antibodies can be used for detecting tau, or fragments thereof, in the context of clinical diagnosis or treatment or in research. For example, the antibodies can be used to detect the presence of tau in a biological sample as an indication that the biological sample comprises tau deposits. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of tau) to the biological sample(s) is increased, decreased, or the same relative to antibody binding to the control sample(s). Increased binding of the antibody to the biological sample(s) relative to the control sample(s) indicates the presence of tau in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of the tau in a biological sample to monitor and evaluate the efficacy of a therapeutic agent being used to treat a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). A biological sample from a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) is evaluated to establish a baseline for the binding of the antibodies to the sample (i.e., a baseline for the presence of the tau in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of tau) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of tau) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of tau), it can be concluded that the therapeutic agent was effective in treating the Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) in the patient. The decrease in antibody binding can be statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

The antibodies can also be used as research reagents for laboratory research in detecting tau, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify tau, or binding partners of tau, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of Tau Monoclonal Antibodies

Monoclonal antibodies against tau were generated as follows. Immunizations were performed with either recombinant N-terminally His-tagged 383 a.a. human tau (4R0N), containing a P301S mutation [immunogen A] or recombinant 383 a.a. human tau (4R0N), containing a P301S mutation, lacking an N-terminal His-tag [immunogen B]. Immunogens were emulsified in RIBI adjuvant.

Five week old female Balb/c mice were intraperitoneally immunized with 25 μg of immunogen A on day 0, and 10 μg of immunogen A each on days 7, 14, 21, 27, 34, 48, 55, and 62. Mice were immunized with 10 μg of immunogen B on days 76 and 90. On days 43 and 98, mice were bled and titered against immunogen A; on day 101 the animals with highest titers were boosted with a terminal immunization of 50 μg immunogen B, which was delivered ½ intraperitoneally and ½ intravenously. Fused hybridomas were screened via ELISA against both immunogens, and positives with the highest signal were epitope mapped (see Example 2).

Example 2. Epitope Mapping of Antibody 3D6

A range of overlapping biotinylated peptides spanning the entire 383aa 4R0N human tau protein were used for mapping the murine 3D6 antibody. Additional peptides were used to model potential post-translational modifications of the C- and N-terminal ends of the protein.

Biotinylated peptides were bound to separate wells of a streptavidin-coated ELISA plate. The plate was blocked and treated with murine 3D6, followed by incubation with a horseradish peroxidase-conjugated anti-mouse antibody. After thorough washing, OPD was applied to the plate and allowed to develop. The plate was read at 450 nm absorbance. Background subtraction was performed with absorbance values from wells containing no primary antibody, and a threshold for positive binding was set to 0.2 absorbance units. Binding was mapped to sites within the MTBR region.

Example 3. Design of Humanized 3D6 Antibodies

The starting point or donor antibody for humanization was the mouse antibody 3D6. The heavy chain variable amino acid sequence of mature m3D6 is provided as SEQ ID NO:7. The light chain variable amino acid sequence of mature m3D6 is provided as SEQ ID NO:11. The heavy chain Kabat/Chothia Composite CDR1, CDR2, and CDR3 amino acid sequences are provided as SEQ ID NO: 8, SEQ ID NO: 9, and a sequence of LDF, respectively. The light chain Kabat CDR1, CDR2, and CDR3 amino acid sequences are provided as SEQ ID NOs12-14 respectively. Kabat numbering is used throughout.

The variable kappa (Vk) of 3D6 belongs to mouse Kabat subgroup 2 which corresponds to human Kabat subgroup 2 and the variable heavy (Vh) to mouse Kabat subgroup 2c which corresponds to human Kabat subgroup 1 [Kabat E. A., et al., (1991), Sequences of Proteins of Immunological Interest, Fifth Edition. NIH Publication No. 91-3242]. 16 residue Chothia CDR-L1 belongs to canonical class 4, 7 residue Chothia CDR-L2 to class 1, 9 residue Chothia CDR-L3 to class 1 in Vk [Martin A. C, and Thornton J. M. (1996) J. Mol. Biol. 263:800-15. [Martin & Thornton, 1996]. 10 residue Chothia CDR-H1 belongs to class 1, 17 residue Chothia CDR-H2 to class 2 [Martin & Thornton, 1996]]. CDR-H3 has no canonical classes. A search was made over the protein sequences in the PDB database [Deshpande N, et al., (2005) Nucleic Acids Res. 33: D233-7.] to find structures which would provide a rough structural model of 3D6. To build up a Fv model of 3D6, a structure of murine anti-pyroglutamate-Abeta antibody Fab c #24 (pdb code 5MYX) [Piechotta, A. et al., 2017, J Biol Chem. 292: 12713-12724] with a resolution of 1.4 A was used. It retained the same canonical structure for the loops as 3D6.

The frameworks of 3D6 VH share a high degree of sequence similarity with the corresponding regions of humanized 48G7 Fab PDB: 2RCS, designed by Wedemayer, G. J., et al. (1997; Science 276: 1665-1669). The variable domains of 3D6 and 48G7 fab also share identical lengths for the CDR-H1, H2 loops. Similarly, the frameworks of 3D6 VL share a high degree of sequence similarity with the corresponding regions of human antibody ARX71335 VL, cloned by Dafferner, A. J., et al. (2017; Direct Submission). The variable light domain of 3D6 and ARX71335 antibody also share identical lengths for the CDR-L1, L2 and L3 loops. Accordingly, the framework regions of 48G7 VH (2RCS-VH) and ARX71335 VL were chosen as the acceptor sequences for the CDRs of 3D6. A model of the 3D6 CDRs grafted onto the respective human frame-works for VH and VL was built and used as a guidance for further backmutations.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Residues were changed to align with corresponding human germ line sequence, where possible, to enhance humanness and to reduce potential immunogenicity. For humanized VLvb2 and VLvb3 variants, mutations were introduced to render the sequences more similar to human germ line gene IGKV2-30*02 (SEQ ID NO:27) For humanized VHvb2, VHvb3, VHvb4, VHvb5, VHvb6, and VHvb6 variants, mutations were introduced to render the sequences more similar to human germ line gene IGHV1-69-2*01 (SEQ ID NO:25)

Versions of hu3D6-VH and hu3D6-VL were designed to enable assessment of various framework residues for their contributions to antigen binding, thermostability, and immunogenicity, and for optimization of glycosylation, aggregation, N-term heterogeneity, thermostability, surface exposed charged patches, surface exposed charge patches, deamination, and proteinase susceptibility. The positions considered for mutation include those that . . .

- define the canonical CDR conformations (summarized in Martin, A. C. R. (2010) Protein sequence and structure analysis of antibody variable domains. In: Kontermann R and Dubel S (eds). Antibody Engineering. Heidelberg, Germany: Springer International Publishing AG.),
- are within the Vernier zone (Foote J and Winter G. (1992) Antibody framework residues affecting the conformation of the hypervariable loops. *J Mol Biol.* 224(2): 487-99.),
- localize to the VH/VL domain interface (summarized in Leger O J P and Saldanha J. (2000) Preparation of recombinant antibodies from immune rodent spleens and the design of their humanisation by CDR grafting. In: Shepherd P and Dean C (eds). *Monoclonal Antibodies: a Practical Approach*. Oxford, UK: Oxford University Press.),
- are susceptible to post-translational modifications, such as glycosylation or pyroglutamination,
- are occupied by residues that are predicted to clash with CDRs, according to the model of 3D6 CDRs grafted onto VH and VL frameworks, or
- are occupied by residues that are rare among sequenced human antibodies, where either the parental mouse 3D6 residue or some other residue is much more prevalent within human antibody repertoire.

Alignments of the murine 3D6 and various humanized antibodies are shown for the light chain variable regions (Table 4 and FIG. 2), and heavy chain variable regions (Table 3 and FIG. 1).

7 humanized heavy chain variable region variants and 3 humanized light chain variable region variants were constructed containing different permutations of substitutions: hu3D6VHvb1, hu3D6VHvb2, hu3D6VHvb3, hu3D6VHvb4, hu3D6HVb5, hu3D6VHvb6, or hu3D6VHvb7 (SEQ ID NOs:76-80 and 90-91, respectively); and hu3D6VLvb1, hu3D6VLvb2, or hu3D6VLvb3 (SEQ ID NOs:83-85, respectively) (Tables 3 and 4). The exemplary humanized Vk and Vh designs, with backmutations and other mutations based on selected human frameworks, are shown in Tables 3 and 4, respectively. The bolded areas in Tables 3 and 4 indicate the CDRs as defined by Kabat/Chothia Composite. SEQ ID NOs:76-80 and SEQ ID NOs:90-91 contain backmutations and other mutations as shown in Table 5. The amino acids at positions in hu3D6VHvb1, hu3D6VHvb2, hu3D6VHvb3, hu3D6VHvb4, hu3D6VHvb5, hu3D6VHvb6, and hu3D6VHvb7 are listed in Table 6. The amino acids at positions in hu3D6VLvb1, hu3D6VLvb2, and hu3D6VLvb3 are listed in Table 7. The percentage humanness for humanized VH chains hu3D6VHvb1, hu3D6VHvb2, hu3D6VHvb3, hu3D6VHvb4, hu3D6HVb5, hu3D6VHvb6, and hu3D6VHvb7 (SEQ ID NOs:76-80 and 90-91, respectively) and humanized VL chains hu3D6VLvb1, hu3D6VLvb2, and hu3D6VLvb3 (SEQ ID NOs:83-85, respectively) is shown in Table 8.

TABLE 3

| Kabat residue # | Linear residue # | FR or CDR | Mouse 3D6 VH (SEQ ID NO: 7) | IMGT# IGHV1-69-2*01 (SEQ ID NO: 25) | 2RCS-VH_huFrwk (SEQ ID NO: 75) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|---|---|
| 1 | 1 | Fr1 | E | E | Q | Q | E | E | E | E | E | E |
| 2 | 2 | Fr1 | V | V | V | V | V | V | V | V | V | V |
| 3 | 3 | Fr1 | Q | Q | Q | Q | Q | Q | Q | Q | Q | Q |
| 4 | 4 | Fr1 | L | L | L | L | L | L | L | L | L | L |
| 5 | 5 | Fr1 | Q | V | Q | Q | V | V | V | V | V | V |
| 6 | 6 | Fr1 | Q | Q | Q | Q | Q | Q | Q | Q | Q | Q |
| 7 | 7 | Fr1 | S | S | S | S | S | S | S | S | S | S |
| 8 | 8 | Fr1 | G | G | G | G | G | G | G | G | G | G |
| 9 | 9 | Fr1 | A | A | A | A | A | A | A | A | A | A |
| 10 | 10 | Fr1 | D | E | E | E | E | E | E | E | E | E |
| 11 | 11 | Fr1 | L | V | L | L | V | V | V | V | V | V |
| 12 | 12 | Fr1 | V | K | V | V | V | V | V | V | V | V |
| 13 | 13 | Fr1 | R | K | K | K | K | K | K | K | K | K |
| 14 | 14 | Fr1 | P | P | P | P | P | P | P | P | P | P |
| 15 | 15 | Fr1 | G | G | G | G | G | G | G | G | G | G |
| 16 | 16 | Fr1 | A | A | A | A | A | A | A | A | A | A |
| 17 | 17 | Fr1 | L | T | S | S | S | T | T | T | T | T |
| 18 | 18 | Fr1 | V | V | V | V | V | V | V | V | V | V |
| 19 | 19 | Fr1 | K | K | K | K | K | K | K | K | K | K |
| 20 | 20 | Fr1 | L | I | L | L | I | I | I | I | I | I |
| 21 | 21 | Fr1 | S | S | S | S | S | S | S | S | S | S |
| 22 | 22 | Fr1 | C | C | C | C | C | C | C | C | C | C |
| 23 | 23 | Fr1 | K | K | T | T | K | K | K | K | K | K |
| 24 | 24 | Fr1 | A | V | A | A | A | A | A | A | A | A |
| 25 | 25 | Fr1 | S | S | S | S | S | S | S | S | S | S |
| **26** | **26** | **CDR-H1** | **G** | **G** | **G** | **G** | **G** | **G** | **G** | **G** | **G** | **G** |
| **27** | **27** | **CDR-H1** | **F** | **Y** | **F** | **F** | **F** | **F** | **F** | **F** | **F** | **F** |
| **28** | **28** | **CDR-H1** | **N** | **T** | **N** | **N** | **N** | **N** | **T** | **T** | **T** | **T** |
| **29** | **29** | **CDR-H1** | **I** | **F** | **I** | **I** | **I** | **I** | **I** | **I** | **I** | **I** |
| **30** | **30** | **CDR-H1** | **K** | **T** | **K** | **K** | **K** | **K** | **K** | **K** | **K** | **K** |
| **31** | **31** | **CDR-H1** | **D** | **D** | **D** | **D** | **D** | **D** | **D** | **D** | **D** | **D** |
| **32** | **32** | **CDR-H1** | **Y** | **Y** | **T** | **Y** | **Y** | **Y** | **Y** | **Y** | **Y** | **Y** |
| **33** | **33** | **CDR-H1** | **Y** | **Y** | **Y** | **Y** | **Y** | **Y** | **Y** | **Y** | **Y** | **Y** |
| **34** | **34** | **CDR-H1** | **L** | **M** | **M** | **L** | **L** | **L** | **L** | **L** | **L** | **L** |
| **35** | **35** | **CDR-H1** | **H** | **H** | **H** | **H** | **H** | **H** | **H** | **H** | **H** | **H** |

TABLE 3-continued

| Kabat residue # | Linear residue # | FR or CDR | Mouse 3D6 VH (SEQ ID NO: 7) | IMGT# IGHV1-69-2*01 (SEQ ID NO: 25) | 2RCS-VH_huFrwk (SEQ ID NO: 75) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|---|---|
| **35A** | | **CDR-H1** | — | | — | — | — | — | — | — | — | — |
| **35B** | | **CDR-H1** | — | | — | — | — | — | — | — | — | — |
| 36 | 36 | Fr2 | W | W | W | W | W | W | W | W | W | W |
| 37 | 37 | Fr2 | V | V | V | V | V | V | V | V | V | V |
| 38 | 38 | Fr2 | R | Q | K | K | R | R | R | R | R | R |
| 39 | 39 | Fr2 | Q | Q | Q | Q | Q | Q | Q | Q | Q | Q |
| 40 | 40 | Fr2 | R | A | R | R | R | R | R | R | R | R |
| 41 | 41 | Fr2 | P | P | P | P | P | P | P | P | P | P |
| 42 | 42 | Fr2 | E | G | E | E | G | G | G | G | G | G |
| 43 | 43 | Fr2 | Q | K | Q | Q | K | K | K | K | K | K |
| 44 | 44 | Fr2 | G | G | G | G | G | G | G | G | G | G |
| 45 | 45 | Fr2 | L | L | L | L | L | L | L | L | L | L |
| 46 | 46 | Fr2 | E | E | E | E | E | E | E | E | E | E |
| 47 | 47 | Fr2 | W | W | W | W | W | W | W | W | W | W |
| 48 | 48 | Fr2 | I | M | I | I | I | I | I | I | I | I |
| 49 | 49 | Fr2 | G | G | G | G | G | G | G | G | G | G |
| **50** | **50** | **CDR-H2** | **W** | **L** | **R** | **W** | **W** | **W** | **W** | **W** | **W** | **W** |
| **51** | **51** | **CDR-H2** | **I** | **V** | **I** | **I** | **I** | **I** | **I** | **I** | **I** | **I** |
| **52** | **52** | **CDR-H2** | **D** | **D** | **D** | **D** | **D** | **D** | **D** | **D** | **D** | **D** |
| **52A** | **53** | **CDR-H2** | **P** | **P** | **P** | **P** | **P** | **P** | **P** | **P** | **P** | **P** |
| **52B** | | **CDR-H2** | — | — | — | — | — | — | — | — | — | — |
| **52C** | | **CDR-H2** | — | — | — | — | — | — | — | — | — | — |
| **53** | **54** | **CDR-H2** | **E** | **E** | **A** | **E** | **E** | **E** | **E** | **E** | **E** | **E** |
| **54** | **55** | **CDR-H2** | **N** | **D** | **N** | **N** | **N** | **N** | **N** | **D** | **D** | **D** |
| **55** | **56** | **CDR-H2** | **G** | **G** | **G** | **G** | **G** | **G** | **G** | **G** | **G** | **G** |
| **56** | **57** | **CDR-H2** | **D** | **E** | **N** | **D** | **D** | **D** | **D** | **E** | **E** | **E** |
| **57** | **58** | **CDR-H2** | **T** | **T** | **T** | **T** | **T** | **T** | **T** | **T** | **T** | **T** |
| **58** | **59** | **CDR-H2** | **V** | **I** | **K** | **V** | **V** | **I** | **I** | **I** | **V** | **V** |
| **59** | **60** | **CDR-H2** | **Y** | **Y** | **Y** | **Y** | **Y** | **Y** | **Y** | **Y** | **Y** | **Y** |
| **60** | **61** | **CDR-H2** | **D** | **A** | **D** | **D** | **D** | **D** | **D** | **D** | **D** | **D** |
| **61** | **62** | **CDR-H2** | **P** | **E** | **P** | **P** | **P** | **P** | **P** | **P** | **P** | **P** |
| **62** | **63** | **CDR-H2** | **K** | **K** | **K** | **K** | **K** | **K** | **K** | **K** | **K** | **K** |
| **63** | **64** | **CDR-H2** | **F** | **F** | **F** | **F** | **F** | **F** | **F** | **F** | **F** | **F** |
| **64** | **65** | **CDR-H2** | **Q** | **Q** | **Q** | **Q** | **Q** | **Q** | **Q** | **Q** | **Q** | **Q** |
| **65** | **66** | **CDR-H2** | **G** | **G** | **G** | **G** | **G** | **G** | **G** | **G** | **G** | **G** |
| 66 | 67 | Fr3 | K | R | K | K | R | R | R | R | R | R |
| 67 | 68 | Fr3 | A | V | A | A | A | A | V | V | V | V |
| 68 | 69 | Fr3 | T | T | T | T | T | T | T | T | T | T |
| 69 | 70 | Fr3 | I | I | I | I | I | I | I | I | I | I |
| 70 | 71 | Fr3 | T | T | T | T | T | T | T | T | T | T |
| 71 | 72 | Fr3 | A | A | A | A | A | A | A | A | A | A |
| 72 | 73 | Fr3 | D | D | D | D | D | D | D | D | D | D |
| 73 | 74 | Fr3 | T | T | T | T | T | T | T | T | T | T |
| 74 | 75 | Fr3 | S | S | S | S | S | S | S | S | S | S |
| 75 | 76 | Fr3 | S | T | S | S | T | T | T | T | T | T |
| 76 | 77 | Fr3 | N | D | N | N | D | D | D | D | D | D |
| 77 | 78 | Fr3 | T | T | T | T | T | T | T | T | T | T |
| 78 | 79 | Fr3 | A | A | A | A | A | A | A | A | A | A |
| 79 | 80 | Fr3 | Y | Y | Y | Y | Y | Y | Y | Y | Y | Y |
| 80 | 81 | Fr3 | L | M | L | L | L | M | M | M | M | M |
| 81 | 82 | Fr3 | Q | E | Q | Q | E | E | E | E | E | E |
| 82 | 83 | Fr3 | L | L | L | L | L | L | L | L | L | L |
| 82A | 84 | Fr3 | G | S | S | S | S | S | S | S | S | S |
| 82B | 85 | Fr3 | S | S | S | S | S | S | S | S | S | S |
| 82C | 86 | Fr3 | L | L | L | L | L | L | L | L | L | L |
| 83 | 87 | Fr3 | T | R | T | T | T | R | R | R | R | R |
| 84 | 88 | Fr3 | S | S | S | S | S | S | S | S | S | S |
| 85 | 89 | Fr3 | E | E | E | E | E | E | E | E | E | E |
| 86 | 90 | Fr3 | D | D | D | D | D | D | D | D | D | D |
| 87 | 91 | Fr3 | T | T | T | T | T | T | T | T | T | T |
| 88 | 92 | Fr3 | A | A | A | A | A | A | A | A | A | A |
| 89 | 93 | Fr3 | V | V | V | V | V | V | V | V | V | V |
| 90 | 94 | Fr3 | Y | Y | Y | Y | Y | Y | Y | Y | Y | Y |
| 91 | 95 | Fr3 | F | Y | Y | F | F | Y | Y | Y | F | Y |
| 92 | 96 | Fr3 | C | C | C | C | C | C | C | C | C | C |
| 93 | 97 | Fr3 | S | A | A | S | S | S | S | S | S | S |
| 94 | 98 | Fr3 | T | T | S | T | T | T | T | T | T | T |
| **95** | **99** | **CDR-H3** | **L** | | **Y** | **L** | **L** | **L** | **L** | **L** | **L** | **L** |
| **96** | | **CDR-H3** | — | | **Y** | — | — | — | — | — | — | — |
| **97** | | **CDR-H3** | — | | **G** | — | — | — | — | — | — | — |
| **98** | | **CDR-H3** | — | | — | — | — | — | — | — | — | — |
| **99** | | **CDR-H3** | — | | — | — | — | — | — | — | — | — |
| **100** | | **CDR-H3** | — | | — | — | — | — | — | — | — | — |
| **100A** | | **CDR-H3** | — | | — | — | — | — | — | — | — | — |

TABLE 3-continued

| Kabat residue # | Linear residue # | FR or CDR | Mouse 3D6 VH (SEQ ID NO: 7) | IMGT# IGHV1-69-2*01 (SEQ ID NO: 25) | 2RCS-VH_huFrwk (SEQ ID NO: 75) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|---|---|
| **100B** | | **CDR-H3** | — | | — | — | — | — | — | — | — | — |
| **100C** | | **CDR-H3** | — | | — | — | — | — | — | — | — | — |
| **100D** | | **CDR-H3** | — | | — | — | — | — | — | — | — | — |
| **100E** | | **CDR-H3** | — | | — | — | — | — | — | — | — | — |
| **100F** | | **CDR-H3** | — | | — | — | — | — | — | — | — | — |
| **100G** | | **CDR-H3** | — | | — | — | — | — | — | — | — | — |
| **100H** | | **CDR-H3** | — | | | — | — | — | — | — | — | — |
| **100I** | | **CDR-H3** | — | | | — | — | — | — | — | — | — |
| **100J** | | **CDR-H3** | — | | | — | — | — | — | — | — | — |
| **100K** | | **CDR-H3** | — | | | — | — | — | — | — | — | — |
| **101** | **100** | **CDR-H3** | **D** | **Q** | **I** | **D** | **D** | **D** | **D** | **D** | **D** | **D** |
| **102** | **101** | **CDR-H3** | **F** | **H** | **Y** | **F** | **F** | **F** | **F** | **F** | **F** | **F** |
| 103 | 102 | Fr4 | W | W | W | W | W | W | W | W | W | W |
| 104 | 103 | Fr4 | G | G | G | G | G | G | G | G | G | G |
| 105 | 104 | Fr4 | Q | Q | Q | Q | Q | Q | Q | Q | Q | Q |
| 106 | 105 | Fr4 | G | G | G | G | G | G | G | G | G | G |
| 107 | 106 | Fr4 | T | T | T | T | T | T | T | T | T | T |
| 108 | 107 | Fr4 | T | L | T | T | L | L | L | L | L | L |
| 109 | 108 | Fr4 | L | V | L | L | V | V | V | V | V | V |
| 110 | 109 | Fr4 | T | T | T | T | T | T | T | T | T | T |
| 111 | 110 | Fr4 | V | V | V | V | V | V | V | V | V | V |
| 112 | 111 | Fr4 | S | S | S | S | S | S | S | S | S | S |
| 113 | 112 | Fr4 | S | S | S | S | S | S | S | S | S | S |

TABLE 4

| Kabat residue # | Linear residue # | FR or CDR | Mouse VL 3D6 (SEQ ID NO: 11) | ARX71335-VL_huFrwk (SEQ ID NO: 82) | IMGT#IGKV2-30*02 (SEQ ID NO: 27) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|---|---|
| 1 | 1 | Fr1 | D | D | D | D | D | D |
| 2 | 2 | Fr1 | V | V | V | V | V | V |
| 3 | 3 | Fr1 | V | V | V | V | V | V |
| 4 | 4 | Fr1 | M | M | M | M | M | M |
| 5 | 5 | Fr1 | T | T | T | T | T | T |
| 6 | 6 | Fr1 | Q | Q | Q | Q | Q | Q |
| 7 | 7 | Fr1 | T | T | S | T | S | S |
| 8 | 8 | Fr1 | P | P | P | P | P | P |
| 9 | 9 | Fr1 | L | L | L | L | L | L |
| 10 | 10 | Fr1 | T | T | S | T | S | S |
| 11 | 11 | Fr1 | L | L | L | L | L | L |
| 12 | 12 | Fr1 | S | S | P | S | S | S |
| 13 | 13 | Fr1 | V | V | V | V | V | V |
| 14 | 14 | Fr1 | T | T | T | T | T | T |
| 15 | 15 | Fr1 | I | I | L | I | L | L |
| 16 | 16 | Fr1 | G | G | G | G | G | G |
| 17 | 17 | Fr1 | Q | Q | Q | Q | Q | E |
| 18 | 18 | Fr1 | P | P | P | P | P | P |
| 19 | 19 | Fr1 | A | A | A | A | A | A |
| 20 | 20 | Fr1 | S | S | S | S | S | S |
| 21 | 21 | Fr1 | I | I | I | I | I | I |
| 22 | 22 | Fr1 | S | S | S | S | S | S |
| 23 | 23 | Fr1 | C | C | C | C | C | C |
| **24** | **24** | **CDR-L1** | **K** | **K** | **R** | **K** | **K** | **R** |
| **25** | **25** | **CDR-L1** | **S** | **S** | **S** | **S** | **S** | **S** |
| **26** | **26** | **CDR-L1** | **S** | **S** | **S** | **S** | **S** | **S** |
| **27** | **27** | **CDR-L1** | **Q** | **Q** | **Q** | **Q** | **Q** | **Q** |
| **27A** | **28** | **CDR-L1** | **S** | **S** | **S** | **S** | **S** | **S** |
| **27B** | **29** | **CDR-L1** | **L** | **L** | **L** | **L** | **L** | **L** |
| **27C** | **30** | **CDR-L1** | **L** | **L** | **V** | **L** | **L** | **L** |
| **27D** | **31** | **CDR-L1** | **D** | **Y** | **H** | **D** | **D** | **D** |
| **27E** | **32** | **CDR-L1** | **S** | **S** | **S** | **S** | **S** | **S** |
| **27F** | | **CDR-L1** | — | | | | | |
| **28** | **33** | **CDR-L1** | **D** | **N** | **D** | **D** | **D** | **D** |
| **29** | **34** | **CDR-L1** | **G** | **G** | **G** | **G** | **G** | **G** |
| **30** | **35** | **CDR-L1** | **K** | **K** | **N** | **K** | **K** | **K** |
| **31** | **36** | **CDR-L1** | **T** | **T** | **T** | **T** | **T** | **T** |
| **32** | **37** | **CDR-L1** | **Y** | **Y** | **Y** | **Y** | **Y** | **Y** |
| **33** | **38** | **CDR-L1** | **L** | **L** | **L** | **L** | **L** | **L** |
| 34 | **39** | **CDR-L1** | **N** | **N** | **N** | **N** | **N** | **N** |

TABLE 4-continued

| Kabat residue # | Linear residue # | FR or CDR | Mouse VL 3D6 (SEQ ID NO: 11) | ARX71335-VL_huFrwk (SEQ ID NO: 82) | IMGT#IGKV2-30*02 (SEQ ID NO: 27) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|---|---|
| 35 | 40 | Fr2 | W | W | W | W | W | W |
| 36 | 41 | Fr2 | L | L | F | L | L | L |
| 37 | 42 | Fr2 | L | L | Q | L | L | Q |
| 38 | 43 | Fr2 | Q | Q | Q | Q | Q | Q |
| 39 | 44 | Fr2 | R | R | R | R | R | R |
| 40 | 45 | Fr2 | P | P | P | P | P | P |
| 41 | 46 | Fr2 | G | G | G | G | G | G |
| 42 | 47 | Fr2 | Q | Q | Q | Q | Q | Q |
| 43 | 48 | Fr2 | S | S | S | S | S | S |
| 44 | 49 | Fr2 | P | P | P | P | P | P |
| 45 | 50 | Fr2 | K | K | R | K | K | R |
| 46 | 51 | Fr2 | R | R | R | R | R | R |
| 47 | 52 | Fr2 | L | L | L | L | L | L |
| 48 | 53 | Fr2 | I | I | I | I | I | I |
| 49 | 54 | Fr2 | Y | Y | Y | Y | Y | Y |
| **50** | **55** | **CDR-L2** | **L** | **L** | **K** | **L** | **L** | **L** |
| **51** | **56** | **CDR-L2** | **V** | **V** | **V** | **V** | **V** | **V** |
| **52** | **57** | **CDR-L2** | **S** | **S** | **S** | **S** | **S** | **S** |
| **53** | **58** | **CDR-L2** | **K** | **K** | **N** | **K** | **K** | **K** |
| **54** | **59** | **CDR-L2** | **L** | **L** | **R** | **L** | **L** | **L** |
| **55** | **60** | **CDR-L2** | **D** | **D** | **D** | **D** | **D** | **D** |
| **56** | **61** | **CDR-L2** | **S** | **S** | **S** | **S** | **S** | **S** |
| 57 | 62 | Fr3 | G | G | G | G | G | G |
| 58 | 63 | Fr3 | V | V | V | V | V | V |
| 59 | 64 | Fr3 | P | P | P | P | P | P |
| 60 | 65 | Fr3 | D | D | D | D | D | D |
| 61 | 66 | Fr3 | R | R | R | R | R | R |
| 62 | 67 | Fr3 | F | F | F | F | F | F |
| 63 | 68 | Fr3 | T | S | S | S | S | S |
| 64 | 69 | Fr3 | G | G | G | G | G | G |
| 65 | 70 | Fr3 | S | S | S | S | S | S |
| 66 | 71 | Fr3 | G | G | G | G | G | G |
| 67 | 72 | Fr3 | S | S | S | S | S | S |
| 68 | 73 | Fr3 | G | G | G | G | G | G |
| 69 | 74 | Fr3 | T | T | T | T | T | T |
| 70 | 75 | Fr3 | D | D | D | D | D | D |
| 71 | 76 | Fr3 | F | F | F | F | F | F |
| 72 | 77 | Fr3 | T | T | T | T | T | T |
| 73 | 78 | Fr3 | L | L | L | L | L | L |
| 74 | 79 | Fr3 | K | K | K | K | K | K |
| 75 | 80 | Fr3 | I | I | I | I | I | I |
| 76 | 81 | Fr3 | S | S | S | S | S | S |
| 77 | 82 | Fr3 | R | R | R | R | R | R |
| 78 | 83 | Fr3 | V | V | V | V | V | V |
| 79 | 84 | Fr3 | E | E | E | E | E | E |
| 80 | 85 | Fr3 | A | A | A | A | A | A |
| 81 | 86 | Fr3 | E | E | E | E | E | E |
| 82 | 87 | Fr3 | D | D | D | D | D | D |
| 83 | 88 | Fr3 | L | L | V | L | V | V |
| 84 | 89 | Fr3 | G | G | G | G | G | G |
| 85 | 90 | Fr3 | V | V | V | V | V | V |
| 86 | 91 | Fr3 | Y | H | Y | H | Y | Y |
| 87 | 92 | Fr3 | Y | Y | Y | Y | Y | Y |
| 88 | 93 | Fr3 | C | C | C | C | C | C |
| **89** | **94** | **CDR-L3** | **W** | **E** | **M** | **W** | **W** | **W** |
| **90** | **95** | **CDR-L3** | **Q** | **Q** | **Q** | **Q** | **Q** | **Q** |
| **91** | **96** | **CDR-L3** | **G** | **G** | **G** | **G** | **G** | **G** |
| **92** | **97** | **CDR-L3** | **T** | **T** | **T** | **T** | **T** | **T** |
| **93** | **98** | **CDR-L3** | **H** | **H** | **H** | **H** | **H** | **H** |
| **94** | **99** | **CDR-L3** | **F** | **F** | **W** | **F** | **F** | **F** |
| **95** | **100** | **CDR-L3** | **P** | **P** | **P** | **P** | **P** | **P** |
| **95A** | | **CDR-L3** | — | — | — | — | — | — |
| **95B** | | **CDR-L3** | — | — | — | — | — | — |
| **95C** | | **CDR-L3** | — | — | — | — | — | — |
| **95D** | | **CDR-L3** | — | — | — | — | — | — |
| **95E** | | **CDR-L3** | — | — | — | — | — | — |
| **95F** | | **CDR-L3** | — | — | — | — | — | — |
| **96** | **101** | **CDR-L3** | **Y** | **L** | **Y** | **Y** | **Y** | **Y** |
| **97** | **102** | **CDR-L3** | **T** | **T** | **T** | **T** | **T** | **T** |
| 98 | 103 | Fr4 | F | F | F | F | F | F |
| 99 | 104 | Fr4 | G | G | G | G | G | G |
| 100 | 105 | Fr4 | G | A | Q | A | A | Q |
| 101 | 106 | Fr4 | G | G | G | G | G | G |
| 102 | 107 | Fr4 | T | T | T | T | T | T |
| 103 | 108 | Fr4 | K | K | K | K | K | K |

TABLE 4-continued

| Kabat residue # | Linear residue # | FR or CDR | Mouse VL 3D6 (SEQ ID NO: 11) | ARX71335-VL_huFrwk (SEQ ID NO: 82) | IMGT#IGKV2-30*02 (SEQ ID NO: 27) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|---|---|
| 104 | 109 | Fr4 | L | L | L | L | L | L |
| 105 | 110 | Fr4 | E | E | E | E | E | E |
| 106 | 111 | Fr4 | I | L | I | L | I | I |
| 106A | 112 | Fr4 | K | K | K | K | K | K |
| 107 | 113 | Fr4 | R | | | R | R | R |

TABLE 5

| $V_H$, $V_L$ Backmutations and Other Mutations for Humanized 3D6 | | |
|---|---|---|
| $V_H$ or $V_L$ Variant | $V_H$ or $V_L$ Exon Acceptor Sequence | Changes from Acceptor Framework (or CDR) Residues (based on Kabat/Chothia Composite CDRs) |
| Hu3D6VHvb1 (SEQ ID NO: 76) | PDB ID 2RCS-VH_huFrwk (SEQ ID NO: 75) IMGT# IGHV1-69-2*01 (SEQ ID NO: 25) | H91, H93, H94 |
| Hu3D6VHvb2 (SEQ ID NO: 77) | PDB ID 2RCS-VH_huFrwk (SEQ ID NO: 75) IMGT# IGHV1-69-2*01 (SEQ ID NO: 25) | H1, H5, H11, H20, H23, H38, H42, H43, H66, H67, H75, H76, H81, H91, H93, H94 |
| Hu3D6VHvb3 (SEQ ID NO: 78) | PDB ID 2RCS-VH_huFrwk (SEQ ID NO: 75) IMGT# IGHV1-69-2*01 (SEQ ID NO: 25) | H1, H5, H11, H17, H20, H23, H38, H42, H43, H58, H66, H67, H75, H76, H80, H81, H83, H93, H94, H108, H109 |
| Hu3D6VHvb4 (SEQ ID NO: 79) | PDB ID 2RCS-VH_huFrwk (SEQ ID NO: 75) IMGT# IGHV1-69-2*01 (SEQ ID NO: 25) | H1, H5, H11, H17, H20, H23, H28, H38, H42, H43, H58, H66, H67, H75, H76, H80, H81, H83, H93, H94, H108, H109 |
| Hu3D6VHvb5 (SEQ ID NO: 80) | PDB ID 2RCS-VH_huFrwk (SEQ ID NO: 75) IMGT# IGHV1-69-2*01 (SEQ ID NO: 25) | H1, H5, H11, H17, H20, H23, H28, H38, H42, H43, H54, H56, H58, H66, H67, H75, H76, H80, H81, H83, H93, H94, H108, H109 |
| Hu3D6 VHvb6 (SEQ ID NO: 90) | PDB ID 2RCS-VH_huFrwk (SEQ ID NO: 75) IMGT# IGHV1-69-2*01 (SEQ ID NO: 25) | H1, H5, H11, H17, H20, H23, H28, H38, H42, H43, H54, H56, H66, H67, H75, H76, H80, H81, H83, H91, H93, H94, H108, H109 |
| Hu3D6 VHvb7 (SEQ ID NO: 91) | PDB ID 2RCS-VH_huFrwk (SEQ ID NO: 75) IMGT# IGHV1-69-2*01 (SEQ ID NO: 25) | H1, H5, H11, H17, H20, H23, H28, H38, H42, H43, H54, H56, H66, H67, H75, H76, H80, H81, H83, H93, H94, H108, H109 |
| Hu3D6VLvb1 (SEQ ID NO: 83) | PDB ID ARX71335-VL_huFrwk (SEQ ID NO: 82); IMGT#IGKV2-30*02 (SEQ ID NO: 27) | |
| Hu3D6VLvb2 (SEQ ID NO: 84) | PDB ID ARX71335-VL_huFrwk (SEQ ID NO: 82); IMGT#IGKV2-30*02 (SEQ ID NO: 27) | L7, L10, L15, L83, L86, L106 |
| Hu3D6VLvb3 (SEQ ID NO: 85) | PDB ID ARX71335-VL_huFrwk (SEQ ID NO: 82); IMGT#IGKV2-30*02 (SEQ ID NO: 27) | L7, L10, L15, L17, L24, L37, L45, L83, L86, L100, L106 |

TABLE 6

Kabat Numbering of Framework (or CDR) Residues (based on Kabat/Chothia Composite CDRs) for Backmutations and Other Mutations in Heavy Chains of Humanized 3D6 Antibodies

| Residue | 2RCS-VH_huFrwk (SEQ ID NO: 75) | (Heavy Chain)IMGT# IGHV1-69-2*01 (SEQ ID NO: 25) | Mouse 3D6 (SEQ ID NO: 7) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|
| H1 | Q | E | E | Q | E | E | E | E | E | E |
| H5 | Q | V | Q | Q | V | V | V | V | V | V |
| H11 | L | V | L | L | V | V | V | V | V | V |
| H17 | S | T | L | S | S | T | T | T | T | T |
| H20 | L | I | L | L | I | I | I | I | I | I |
| H23 | T | K | K | T | K | K | K | K | K | K |
| H28 | N | T | N | N | N | N | T | T | T | T |
| H38 | K | Q | R | K | R | R | R | R | R | R |
| H42 | E | G | E | E | G | G | G | G | G | G |
| H43 | Q | K | Q | Q | K | K | K | K | K | K |
| H54 | N | D | N | N | N | N | N | D | D | D |
| H56 | N | E | D | D | D | D | D | E | E | E |
| H58 | K | I | V | V | V | I | I | I | V | V |
| H66 | K | R | K | K | R | R | R | R | R | R |
| H67 | A | V | A | A | A | A | V | V | V | V |
| H75 | S | T | S | S | T | T | T | T | T | T |
| H76 | N | D | N | N | D | D | D | D | D | D |
| H80 | L | M | L | L | L | M | M | M | M | M |
| H81 | Q | E | Q | Q | E | E | E | E | E | E |
| H83 | T | R | T | T | T | R | R | R | R | R |
| H91 | Y | Y | F | F | F | Y | Y | Y | F | Y |
| H93 | A | A | S | S | S | S | S | S | S | S |
| H94 | S | T | T | T | T | T | T | T | T | T |
| H108 | T | L | T | T | L | L | L | L | L | L |
| H109 | L | V | L | L | V | V | V | V | V | V |

TABLE 7

Kabat Numbering of Framework Residues (based on Kabat/Chothia Composite CDRs) for Backmutations and Other Mutations in Light Chains of Humanized 3D6 Antibodies

| Residue | ARX71335-VL_huFrwk (SEQ ID NO: 82) | (Light Chain) IMGT#IGKV2-30*02 (SEQ ID NO: 27) | Mouse 3D6 (SEQ ID NO: 11) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|
| L7 | T | S | T | T | S | S |
| L10 | T | S | T | T | S | S |
| L15 | I | L | I | I | L | L |
| L17 | Q | Q | Q | Q | Q | E |
| L24 | K | R | K | K | K | R |
| L37 | L | Q | L | L | L | Q |
| L45 | K | R | K | K | K | R |
| L83 | L | V | L | L | V | V |
| L86 | H | Y | Y | H | Y | Y |
| L100 | A | Q | G | A | A | Q |
| L106 | L | I | I | L | I | I |

TABLE 8

Percentage Humanness of Heavy and Light Chains of Humanized 3D6 Antibodies

| $V_H$ or $V_L$ Variant | % Humanness |
|---|---|
| Hu3D6VHvb1 (SEQ ID NO: 76) | 65.3% |
| Hu3D6VHvb2 (SEQ ID NO: 77) | 76.5% |
| Hu3D6VHvb3 (SEQ ID NO: 78) | 81.6% |
| Hu3D6VHvb4 (SEQ ID NO: 79) | 83.7% |
| Hu3D6VHvb5 (SEQ ID NO: 80) | 85.7% |
| Hu3D6 VHvb6 (SEQ ID NO: 90) | 83.7% |
| Hu3D6 VHvb7 (SEQ ID NO: 91) | 84.7% |
| Hu3D6VLvb1 (SEQ ID NO: 83) | 82.0% |

TABLE 8-continued

Percentage Humanness of Heavy and Light Chains of Humanized 3D6 Antibodies

| $V_H$ or $V_L$ Variant | % Humanness |
|---|---|
| Hu3D6VLvb2 (SEQ ID NO: 84) | 87.0% |
| Hu3D6VLvb3 (SEQ ID NO: 85) | 89.0% |

Positions at which canonical, vernier, or interface residues differ between mouse and human acceptor sequences are candidates for substitution. Examples of canonical/CDR interacting residues include Kabat residues H54 and H94 in Table 3. Examples of vernier residues include Kabat residues H28, H67, H93, and H94 in Table 3. Examples of interface/packing (VH+VL) residues include Kabat residues H91 and H93 in Table 3.

The rationales for selection of the positions indicated in Table 3 in the heavy chain variable region as candidates for substitution are as follows.

Heavy Chain Variable Regions hu3D6VHvb1 consists of the CDR-H1, H2, and H3 loops of 3D6-VH grafted onto the framework of 48G7-VH (RCS-VH), with backmutations at positions H91 (Y91F), H93 (A93S), and H94 (S94T).

hu3D6VHvb2 reverts all framework substitutions at positions that are key for defining the Chothia canonical classes, are part of the Vernier zone, or localize to the VH/VL domain interface or contribute to structural stability. 3D6-VH_vb2 incorporates backmutations or substitutions Q1E, Q5V, L11V, L20I, T23K, K38R, E42G, Q43K, K66R, S75T, N76D, Q81E, Y91F, A93S, S94T T108L, and L109V, to enable assessment of these positions' contributions to antigen-binding affinity and immunogenicity.

hu3D6VHvb3, hu3D6VHvb4, hu3D6VHvb5, hu3D6VHvb6, and hu3D6VHvb7 consists of further substitutions and either add to antibody stability and/or for optimization of glycosylation, aggregation, N-term heterogeneity, thermostability, surface exposed charged patches, surface exposed charge patches, deamination, and proteinase susceptibility.

Q1E: is a stability enhancing mutation to mitigate pyroglutamate formation potential (Liu, supra.) Q1E is a back-mutation.

Q5V: is a frequency-based and germ line-aligning mutation. Val is most frequent in human sequences at this position. Val is in human germ line gene IMGT #IGHV1-69-2*01 (SEQ ID NO:25) at this position.

L11V: is a germ line-aligning mutation. Val is in human germ line gene IMGT #IGHV1-69-2*01 (SEQ ID NO:25) at this position.

S17T: is a germ line-aligning mutation. Thr is in human germ line gene IMGT #IGHV1-69-2*01 (SEQ ID NO:25) at this position.

L201: is a germ line-aligning mutation. Ile is in human germ line gene IMGT #IGHV1-69-2*01 (SEQ ID NO:25) at this position.

T23K: is a frequency-based and germ line-aligning mutation. Lys is more frequent at this position. Lys is in human germ line gene IMGT #IGHV1-69-2*01 (SEQ ID NO:25) at this position.

N28T: This is a CDR-H1 residue substitution to Thr. N28T is a germ line-aligning mutation. Thr is in human germ line gene IMGT #IGHV1-69-2*01 (SEQ ID NO:25) at this position.

K38R: is a frequency-based back-mutation. Arg is most frequent at this position. Arg at this position is predicted to make two H-bonds with Glu 46 in addition to one H-bond each with Asp86 and Tyr 90 in heavy chain; therefore, Arg substitution may enhance stability over Lys at this position.

E42G: is a frequency-based and germ line-aligning mutation. Gly is in human germ line gene IMGT #IGHV1-69-2*01 (SEQ ID NO:25) at this position. Gly is most frequent at this position. Gly substitution is predicted not to affect stability.

Q43K: Lys side chain at this position is predicted to make H-bond with G42 besides main chain making H-bonds with Gln 39 and Arg 40, thereby Lys substitution may enhance stability over Q at this position. Q43K is a germ line-aligning mutation. Lys is in human germ line gene IMGT #IGHV1-69-2*01 (SEQ ID NO:25) at this position.

N54D and D56E are substitutions of CDR residues and are predicted to be non-antigen contact positions as per homology model. N54D and D56E substitutions are predicted to stabilize antibody structure. N54D and D56E are germ line-aligning mutations. Asp is at position H54, and Glu is at position H56 in human germ line gene IMGT #IGHV1-69-2*01 (SEQ ID NO:25).

V58I: is a substitution of a CDR-H2 residue. Germline gene IMGT #IGHV1-69-2*01 (SEQ ID NO:25) has Ile at this position. This residue is predicted not to contact antigen.

K66R: Arg at this position is predicted to make H-bonds with Ser 82a and Thr 83 in addition to making H-bond and salt-bridge with Asp 86. K66R is a germ line-aligning mutation. Arg is in human germ line gene IMGT #IGHV1-69-2*01 (SEQ ID NO:25) at this position.

A67V: is a substitution of a Vernier zone residue. Germ line gene IMGT #IGHV1-69-2*01 (SEQ ID NO:25) has Val at this position.

S75T: Ser at this position is predicted to make H-bond with Asp 72 and Tyr 76. Thr at this position is predicted to also make these contacts but being surface exposed residue Thr may enhance antibody stability. S75T is a germ line-aligning mutation. Thr is in human germ line gene IMGT #IGHV1-69-2*01 (SEQ ID NO:25) at this position.

N76D: Asp is a germ line-aligning mutation. Asp is in human germ line gene IMGT #IGHV1-69-2*01 (SEQ ID NO:25) at this position.

L80M: Met is a germ line-aligning mutation. Met is in human germ line gene IMGT #IGHV1-69-2*01 (SEQ ID NO:25) at this position.

Q81E: Glu is predicted to make H-bond plus salt-bridge with K19; hence Glu at this position enhances antibody stability. Q81E is a germ line-aligning mutation. Glu is in human germ line gene IMGT #IGHV1-69-2*01 (SEQ ID NO:25) at this position.

T83R enhances thermostability and increases humanness. Arg is a germ-line aligning mutation. Arg is in human germ line gene IMGT #IGHV1-69-2*01 (SEQ (ID NO: 25) at this position. Arg is most frequent at this position.

Y91F: is mutation of an interface residue, and is a back-mutation. Tyr at this position, may enhance antibody stability.

A93S: is a back-mutation of a Vernier zone and interface zone residue.

S94T: is a back-mutation of a Chothia defined canonical structural residue and vernier residue.

T108L: Leu is a germ line-aligning mutation. Leu is in human germ line gene IMGT #IGHV1-69-2*01 (SEQ ID NO:25) at this position. Leu at this position is predicted to make the antibody less immunogenic and to have no impact on antibody stability.

L109V: is a frequency-based mutation. Val is most frequent at this position. L109V is a germ line-aligning mutation. Val is in human germ line gene IMGT #IGHV1-69-2*01 (SEQ ID NO:25) at this position.

The rationales for selection of the positions indicated in Table 4 in the light chain variable region as candidates for substitution are as follows.

Kappa Light Chain Variable Regions hu3D6VLvb1 consists of the CDR-L1, L2, and L3 loops of 3D6-VL grafted onto the framework of ARX71335 VL.

hu3D6VLvb2 and hu3D6VLvb3

- reverts all framework substitutions at positions that are key for defining the Chothia canonical classes, are part of the Vernier zone, or locate to the VH/VL domain interface. Hu3D6-VLvb2 & Hu3D6-VLvb3 also include substitutions that contribute to structural stability; hu3D6-VL_vb2 incorporates backmutations T7S, I15L, L83V, H86Y and L106I, to enable assessment of these positions' contributions to antigen-binding affinity and immunogenicity.
- Hu3D6-VL_vb3 all substitutions mentioned for vb2 along with additional changes at Q17E, K24R, L37Q, K45R, and L106I T7S: is a germ line-aligning mutation. Ser is in human germ line gene IGKV2-30*02 (SEQ ID NO:27) at this position.

T10S: is a frequency-based and germ line-aligning mutation. Ser is frequent at this position. Ser is in human germ line gene IGKV2-30*02 (SEQ ID NO:27) at this position.

I15L: is a germline-aligning mutation. Leu is in human germ line gene IGKV2-30*02 (SEQ ID NO:27) at this position.

Q17E: Glu at this position is predicted to make H-bond with T14 and salt-bridge with Lys 107, both light chain residues, and to enhance antibody stability.

K24R: is a mutation of a CDR residue. Both Lys and Arg are predicted to make H-bond and salt-bridge with Asp 70 in the light chain. Arg is predicted to fit better in the conformation. Arg is also a germ line-aligning mutation. Arg is in human germ line gene IGKV2-30*02 (SEQ ID NO:27) at this position.

L37Q: This is predicted to be a deep buried residue, Leu is not predicted to interact with surrounding residues, whereas, Gln is predicted to make H-bonds with Q38 and Asp 82 in the light chain. Gln is also a germ line-aligning mutation. Gln is in human germ line gene IGKV2-30*02 (SEQ ID NO:27) at this position.

K45R: Although Lys is predicted to make H-bonds with S56 and Gly 57; Arg's predicted interaction with neighboring residues is much more extensive as it is predicted to form salt-bridges with D55, H-bond with Arg46 and double H-bonds with S56. Arg is also a germ line-aligning mutation. Arg is in human germ line gene IGKV2-30*02 (SEQ ID NO:27) at this position.

L83V: This is a frequency-based mutation of a residue predicted to be surface exposed. Val is also a germ line-aligning mutation. Val is in human germ line gene IGKV2-30*02 (SEQ ID NO:27) at this position.

H86Y: Murine 3D6 VL has Tyr at this position. Tyr is also the most frequent residue at this position.

A100Q: Ala is rare at this position. Ala is predicted to be surface-exposed residue and is not predicted to interact surrounding residues. Gln is most frequent at this position. and is also a germline-aligning mutation. Gln is in human germ line gene IGKV2-30*02 (SEQ ID NO:27) at this position. Gln is predicted to make H-bond with Ser 7 stabilizing intra-chain.

L106I: is a frequency-based and germ line-aligning mutation. Ile is most frequent at this position. Ile is in human germ line gene IGKV2-30*02 (SEQ ID NO:27) at this position.

The designs based on these human frameworks were:

```
heavy chain variable regions
>hu3D6VHvb1
                                              (SEQ ID NO: 76)
QVQLQQSGAELVKPGASVKLSCTASGFNIKDYYLHWVKQRPEQGLEWIGWI

DPENGDTVYDPKFQGKATITADTSSNTAYLQLSSLTSEDTAVYFCSTLDFW

GQGTTLTVSS

>hu3D6VHvb2
                                              (SEQ ID NO: 77)
EVQLVQSGAEVVKPGASVKISCKASGFNIKDYYLHWVRQRPGKGLEWIGWI

DPENGDTVYDPKFQGRATITADTSTDTAYLELSSLTSEDTAVYFCSTLDFW

GQGTLVTVSS

>hu3D6VHvb3
                                              (SEQ ID NO: 78)
EVQLVQSGAEVVKPGATVKISCKASGFNIKDYYLHWVRQRPGKGLEWIGWI

DPENGDTIYDPKFQGRATITADTSTDTAYMELSSLRSEDTAVYYCSTLDFW

GQGTLVTVSS

hu3D6VHvb4
                                              (SEQ ID NO: 79)
EVQLVQSGAEVVKPGATVKISCKASGFTIKDYYLHWVRQRPGKGLEWIGWI

DPENGDTIYDPKFQGRVTITADTSTDTAYMELSSLRSEDTAVYYCSTLDFW

GQGTLVTVSS

>hu3D6VHvb5
                                              (SEQ ID NO: 80)
EVQLVQSGAEVVKPGATVKISCKASGFTIKDYYLHWVRQRPGKGLEWIGWI

DPEDGETIYDPKFQGRVTITADTSTDTAYMELSSLRSEDTAVYYCSTLDFW

GQGTLVTVSS

>hu3D6VHvb6
                                              (SEQ ID NO: 90)
EVQLVQSGAEVVKPGATVKISCKASGFTIKDYYLHWVRQRPGKGLEWIGWI

DPEDGETVYDPKFQGRVTITADTSTDTAYMELSSLRSEDTAVYFCSTLDFW

GQGTLVTVSS

>hu3D6VHvb7
                                              (SEQ ID NO: 91)
EVQLVQSGAEVVKPGATVKISCKASGFTIKDYYLHWVRQRPGKGLEWIGWI

DPEDGETVYDPKFQGRVTITADTSTDTAYMELSSLRSEDTAVYYCSTLDFW

GQGTLVTVSS

kappa light chain variable regions
hu3D6VLvb1
                                              (SEQ ID NO: 83)
DVVMTQTPLTLSVTIGQPASISCKSSQSLLDSDGKTYLNWLLQRPGQSPKR

LIYLVSKLDSGVPDRFSGSGSGTDFTLKISRVEAEDLGVHYCWQGTHFPYT

FGAGTKLELKR

>hu3D6VLvb2
                                              (SEQ ID NO: 84)
DVVMTQSPLSLSVTLGQPASISCKSSQSLLDSDGKTYLNWLLQRPGQSPKR

LIYLVSKLDSGVPDRFSGSGSGTDFTLKISRVEAEDVGVYYCWQGTHFPYT

FGAGTKLEIKR
```

-continued

```
>hu3D6VLvb3
                                          (SEQ ID NO: 85)
DVVMTQSPLSLSVTLGEPASISCRSSQSLLDSDGKTYLNWLQQRPGQSPRR

LIYLVSKLDSGVPDRFSGSGSGTDFTLKISRVEAEDVGVYYCWQGTHFPYT

FGQGTKLEIKR
```

Humanized sequences are generated using a two-stage PCR protocol that allows introduction of multiple mutations, deletions, and insertions using QuikChange site-directed mutagenesis [Wang, W. and Malcolm, B. A. (1999) BioTechniques 26:680-682).

Example 4. Mouse Monoclonal Antibodies Bind Tau in ELISA Assays

Methods: Indirect ELISA: 96-well polystyrene plates were coated with capture antibodies anti-6×His (FIG. 3A) or polyclonal anti-tau (Dako #A0024, FIG. 3B) suspended in 1×PBS for 2 hr at RT or 16 hr at 4° C. Coating was removed, and plates were blocked for 1 hr with 1% BSA in 1×PBS, followed by incubation with human recombinant tau, either with (FIG. 3A) or without (FIG. 3B) a polyhistidine tag at the N-terminus of the protein. After washing, plates were incubated with indicated antibodies, washed, and incubated with HRP-conjugated goat anti-mouse secondary antibody. Plates were developed with TMB, and $A_{450}$ was measured with a plate reader.

Sandwich ELISA: 96-well polystyrene plates were coated with anti-mouse antibodies in 1×PBS for 2 hr at RT or 16 hr at 4° C. Coating was removed, and plates were blocked for 1 hr with 1% BSA in 1×PBS. The plate was next incubated with the Indicated antibodies at identical concentrations, diluted in 0.1% BSA in 1×PBS. Plates were successively treated with human tau, polyclonal rabbit anti-tau (Dako #A0024), and HRP-conjugated goat anti-rabbit antibody, all diluted in 0.1% BSA in PBS with washes occurring between each step. Streptavidin-HRP was added, plates were developed with TMB, and $A_{450}$ was measured with a plate reader. See FIG. 3C.

Results: A panel of hybridoma-produced antibodies were assayed for binding to tau via a number of different ELISA formats. Detection of tau was confirmed using an indirect format, using tau protein immobilized by its N-terminally fused polyhistidine tag (FIG. 3A). Binding to the native, untagged protein was also confirmed (FIG. 3B). To assess the solution affinity of the various antibodies, a sandwich ELISA format was used in which tested hybridoma antibodies were used as capture reagents (FIG. 3C).

Example 5. Affinity of Mouse Monoclonal Antibodies to Tau

Methods: SPR analysis was performed using a Biacore T200 to determine the binding kinetics of murine antibodies to recombinant human tau. To prepare a sensor surface, anti-mouse antibody (GE Life Sciences) was immobilized on sensor chip CM5 via amine coupling, and antibody was captured at a level to ensure maximum binding of 50 RU. Various concentrations of recombinant tau ranging from 10-0.14 nM were passed over the captured ligand at a flow rate of 50 μL/min in running buffer (HBS+0.05% P-20, 1 mg/mL BSA), for 180 sec association and 900 sec dissociation. Data were double-referenced to both an irrelevant sensor not containing antibody ligand, and 0 nM analyte concentration to account for the dissociation of ligand from the capture moiety. Data was then analyzed using a global 1:1 fit.

Figures 4, 5:
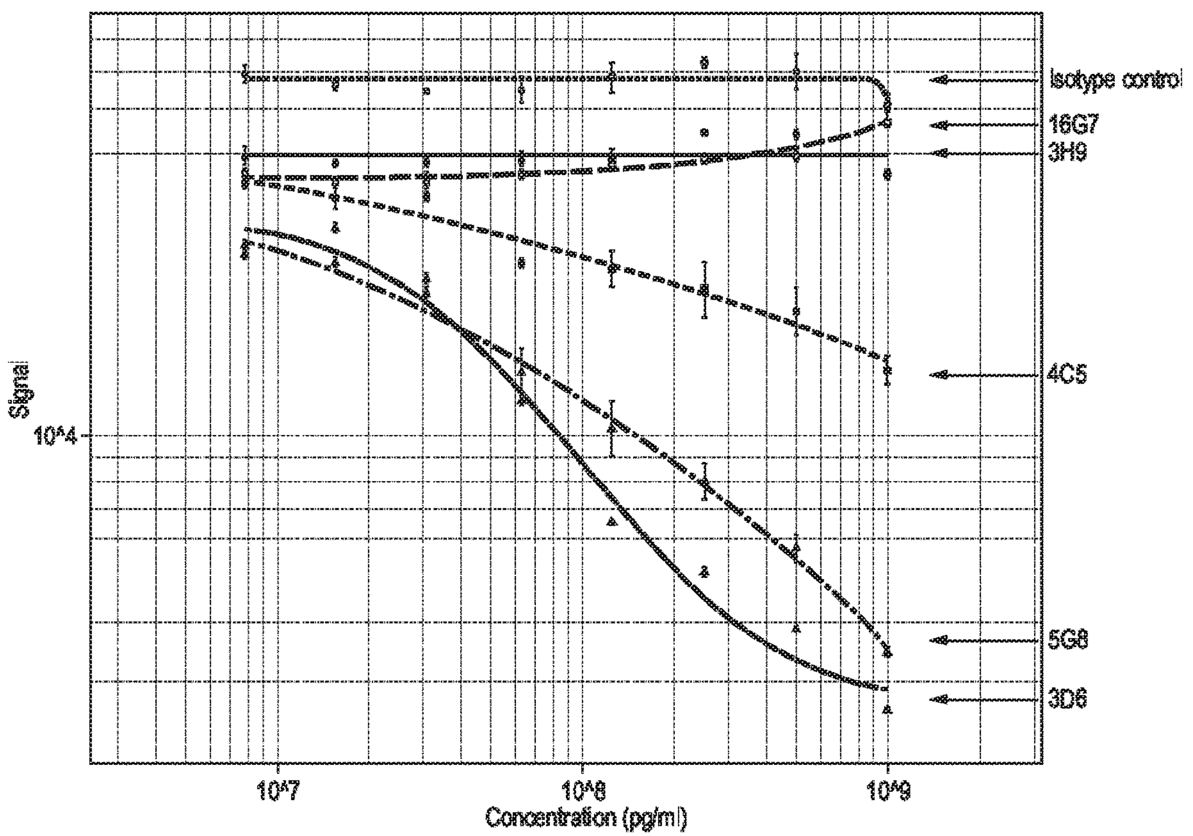
FIG. 4 depicts binding kinetics for selected mouse monoclonal anti-tau antibodies to recombinant human tau.
FIG. 5 depicts results of functional blocking assays for selected mouse monoclonal anti-tau antibodies.

Results: Multiple murine antibodies were selected based on their performance in a battery of ELISA assays, and their binding affinities were assessed via SPR. Antibodies were tested in parallel sets, and their binding association and dissociation rates were compared to select the highest binder to recombinant human tau. The highest binding affinity was observed with antibody clone 3D6. Binding affinities are shown in FIG. 4.

Example 6. Mouse Monoclonal Antibodies Prevent Binding of Human Tau to the Surface of Immortalized Neuronal Cells Methods: Inhibition_of Tau Binding to B103 Neuroblastoma Cells with anti-Tau Monoclonal Antibodies 1. Resuspend B103 cells in PBS at $5\times10^5$ cells/mL. Plate 50 μL of cell suspension per well in a MSD High Bind plate. This results in 25K cells/well. Cover the plate and allow cells to attach at 37° C., 5% $CO_2$, for 2 hrs.

2. Following cell attachment, remove PBS from wells by inverting plate and gently tapping to remove excess buffer. Add 50 μL of 3% MSD Blocker A in PBS or other suitable blocking buffer to each well and incubate plate at RT for 1 hr without shaking.

3. During the plate blocking step co-incubate Tau and anti-Tau antibodies as follows:

a. Start with anti-Tau antibody at 2 mg/mL and serial dilute in PBS, 1:2, for 7 additional dilutions.

b. Dilute Tau to 20 nM in PBS. The Tau concentration will be constant in each well.

c. Mix the Tau and anti-Tau antibody, 1:1, for a final Tau concentration of 10 nM and a starting concentration of anti-Tau of 1 mg/mL.

d. Incubate the mixture for approximately 1 hr at RT with shaking (600 rpm).

4. After plate blocking, step 2, remove blocking buffer from wells by inverting plate and gently tapping and wash plate 2× with PBS using a multichannel pipette. Ensure excess buffer is completely removed. Cool the plated cells to 4° C. prior to adding the Tau: anti-Tau complexes.

5. Add 50 μL of cooled complex, step 3, to the plated cells and incubate on ice for 30 minutes.

6. Wash plate 2× with chilled PBS as previously described.

7. Add 50 μL per well of the 16B5.SULFO-TAG for detection of cell surface bound Tau. Incubate for 30 minutes on ice.

8. Wash plate 2× with chilled PBS again as previously described.

9. Add 150 μL per well of 1× Read Buffer T Without Surfactant (diluted in H20) and read immediately on the MSD SECTOR™ 600 instrument. Avoid introducing bubbles when adding read buffer.

10. Report the MSD signals vs. concentration of anti-Tau.

Antibodies tested were anti-tau antibodies 3D6, 16G7, 3H9, 4C5, and 5G8, and isotype control.

Results:

Decreasing SulfoTag anti-tau signal occurring with increasing test antibody indicates functional blocking of the binding of tau to neuronal cell surfaces. No blocking was observed with isotype control, 16G7, or 3H9. Increasing amounts of functional blocking activity were observed with 4C5, 5G8, and 3D6. 3D6 demonstrated the deepest blocking activity of the antibodies tested. See FIG. 5.

Example 7. Disaggregation Activity

Methods: Aggregation of recombinant tau-Purified recombinant tau with an N-terminal 6×His tag was combined with equimolar amounts of low-molecular weight heparin in 1×PBS (pH 7.4), and incubated at 37° C. for 96 hr on a nutator. Aggregation of the sample was confirmed by binding to Thioflavin T.

Incubation with antibodies—Antibodies were incubated with aggregated, recombinant tau at the indicated molar ratios incubated at 37° C. for 96 hr without rotation or nutation. At the end of the experiment, aggregation was measured by incubating samples with 25 mM Thioflavin T, and measuring emitted fluorescence (450/482 ex/em). Signals were background subtracted to buffer samples.

Figure 6:
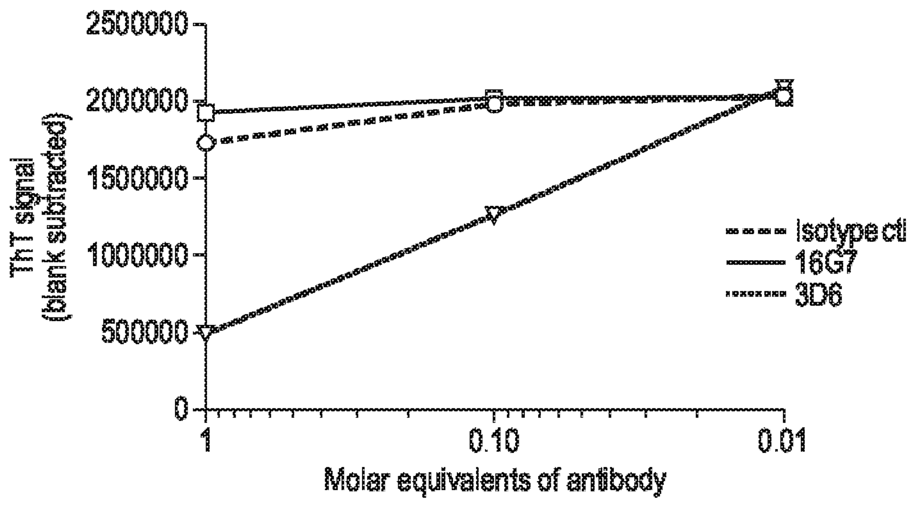
FIG. 6 depicts results of disaggregation assays for selected mouse monoclonal anti-tau antibodies.
Figure 7:
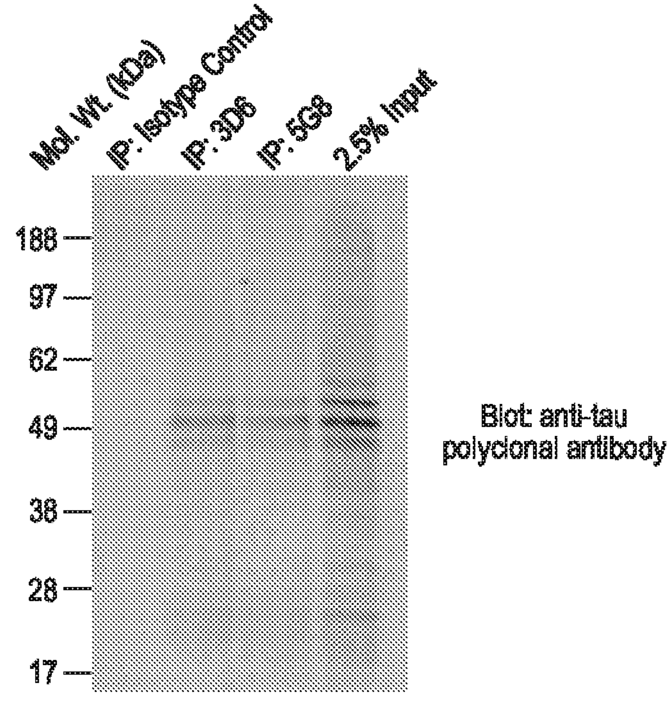
FIG. 7 depicts results of experiments showing that 3D6 and 5G8 immunocapture tau from human Alzheimer's disease tissue.

Results: As shown in FIG. 6, 3D6 preferentially disassembles intact tau fibrils. Varying molar ratios of 3D6 (triangles), isotype control (circles) and 16G7 (squares) were incubated with amyloid-containing tau fibrils for 96 hours. At the end of this period, the extent of aggregation was assessed by binding to Thioflavin T. 3D6 preferentially decreases the Thioflavin T signal present in the sample, compared to both an isotype control antibody as well as to 16G7, an anti-tau antibody that binds to a different region of tau.

Example 8. 3D6 and 5G8 Immunocapture Tau from Human Disease Tissue

Methods: High-salt soluble protein fractions were prepared to 1 mg/ml. For each immunoprecipitation, 200 μg of sample was used. 10 μg of the indicated antibody (either an isotype control, 3D6, or anti-tau antibody 5G8) was added to the high-salt sample preparations, and incubated for 2 hr. Protein G magnetic beads were then added to the mixtures, and incubated for a further hour to capture antibody/antigen complexes. Samples were thoroughly washed with 1×PBS, and beads were boiled in reducing/denaturing sample buffer to release captured proteins. Resulting samples were resolved by SDS-PAGE and Western blotting was performed using a polyclonal anti-tau antibody (Dako, #A0024).

Results: As shown in FIG. 7, 3D6 and 5G8 immunoprecipitated tau from Alzheimer disease tissue. High-salt soluble fractions were immunoprecipitated with the indicated antibody, and detected with a polyclonal anti-tau antibody directed towards a separate region of the tau molecule from the binding sites for 3D6 and tau antibody A. 3D6 robustly captured tau from this fraction. The input (high-salt soluble sample) is shown at right.

Example 9. Immunohistochemistry Immunoreactivity of 3D6

Frontotemporal cortices were obtained from patients without neurodegenerative disease or with Alzheimer disease, which was confirmed upon post-mortem assessment. Immunohistochemistry was performed on lightly acetone-fixed, 10 um slide-mounted cryosections. All staining steps were performed using a Leica BOND Rx autostainer, using Leica consumables. Either murine or a human form of 3D6 was incubated with tissue sections followed by addition of species-appropriate secondary antibodies conjugated to an HRP polymer. To prevent non-specific binding of endogenous immunoglobulin when using humanized antibodies on human tissue, the antibodies were non-covalently labeled with a biotin-conjugated anti-human monovalent Fab fragment in vitro before incubation on tissue. Tissue labeled with the primary antibody-biotin Fab fragment complex was further amplified using an avidin-biotin amplification system (Vector Laboratories, Burlingame, CA). The staining was visualized with a DAB chromogen, which produced a brown deposit. Negative control consisted of performing the entire immunohistochemical procedure on adjacent sections with an IgG isotype control antibody.

Antibodies tested were murine CD6, chimeric 3D6 (which contained VH and VL from the murine antibody with human constant regions, heavy chain SEQ ID NO:72 and light chain SEQ ID NO:73), and humanized variant hu3D6VHv5/hu3D6VLv2.

Staining performed with murine, chimeric, and humanized forms of 3D6 were qualitatively compared and assessed for the strength and intensity of staining, as well as localization of immunoreactivity. Intensity of staining was similar for chimeric and humanized forms of 3D6, and displayed similar localization patterns compared with the murine form of the antibody. Tau was detected in neurofibrillary tangles, fibrils, neuropil threads, and in degenerating axons. There was also notable somal staining detected.

Example 10. Affinity of Humanized Variants Towards Tau

Methods: Indirect ELISA 96-well polystyrene plates are coated with human recombinant tau suspended in 1×PBS for 2 h at RT or 16 h at 4° C. Coating is removed, and plates are blocked for 1 h with 1% BSA in 1×PBS. Humanized variant antibodies at 1 μg/mL in 0.1% BSA in 1×PBS are added to plates for 1 hour followed by washing, and HRP-conjugated goat anti-human antibody are added. Plates are developed with TMB, and $A_{450}$ is measured with a plate reader.

Sandwich ELISA 96-well polystyrene plates are coated with anti-human antibodies in 1×PBS for 2 hr at RT or 16 hr at 4° C. Coating is removed, and plates are blocked for 1 hr with 1% BSA in 1×PBS. Humanized variant antibodies at varying concentrations diluted in 0.1% BSA in 1×PBS are added to plates for 1 hour followed by washing, and biotinylated recombinant human tau diluted in 0.1% BSA in 1×PBS is added. After washing, Streptavidin-HRP is added, plates are developed with TMB, and $A_{450}$ is measured with a plate reader.

Example 11. Analysis of Humanized 3D6 Variants

Humanized 3D6 variants were analyzed for several characteristics, including target binding affinity, activity in cell-based assays, thermostability, expression titer, and presence of aggregation.

Plasmids were generated containing DNA encoding heavy chains hu3D6 VHvb1, h3D6VHvb2, hu3D6VHvb3, hu3D6VHvb4, hu3D6VHvb5, h3D6VHvb6 and h3D6VHvb7 and light chains hu3D6 VLvb1, hu3D6VLvb2, and hu3D6VLvb3. Different combinations of heavy and light chains were transiently expressed as intact antibodies in HEK-293 cells, and antibodies were purified from conditioned media using protein A chromatography. Purified antibodies were analyzed by size exclusion chromatography-high performance liquid chromatography (SEC-HPLC) to detect the presence of aggregation. Results are presented in Table 9, in column labeled "% Monomer."

Purified antibodies were analyzed by differential scanning calorimetry (DSC) to determine the thermostability of each variant. Thermostability values were determined using differential scanning calorimetry (DSC). All DSC scans were performed using a VP-Capillary DSC system (Malvern). All samples were prepared to 0.5 mg/mL in 1×PBS and referenced to 1×PBS. Approximately 0.5 mL of protein solution and buffer were introduced into the sample and reference cell. Calorimetric scan rates were carried out at scan rates of 60° C./hour, from 25° C. to 110° C. under constant pressure. Analysis was performed using origin software. Reported values are the temperature at which the maximal heat capacity of the Fab peak is recorded. Results are presented in Table 9, in column labeled "Thermostability (° C.)."

Titer was determined as follows. After expression in 293 suspension cells, antibodies were purified using Protein A chromatography utilizing standard methods. Following purification, the antibodies were exchanged into 1×PBS and protein concentrations were determined by absorbance at 280 nm. Titers were calculated by dividing the final yield of purified protein by the starting volume of the expression culture, and reported in milligrams per liter. Results are presented in Table 9, in column labeled "Expression titer (mg/L)."

Affinity of purified humanized variants to tau were determined by surface plasmon resonance (SPR). SPR analysis was performed using a Biacore T200 to determine the binding kinetics of humanized antibodies to recombinant human tau. To prepare a sensor surface, anti-human antibody (GE Life Sciences) was immobilized on sensor chip CM3 via amine coupling, and antibody was captured at a level to ensure maximum binding of 50 RU. Various concentrations of recombinant tau ranging from 50-0.62 nM were passed over the captured ligand at a flow rate of 50 μL/min in running buffer (HBS+0.05% P-20, 1 mg/mL BSA), in a single cycle manner. Data were double-referenced to both an irrelevant sensor not containing antibody ligand, and 0 nM analyte concentration to account for the dissociation of ligand from the capture moiety. Data were then analyzed using a 1:1 fit. Results are presented in Table 9, in columns labeled "$k_{on}(M^{-1}s^{-1})$, $k_{off}$ $(s^{-1})$, and $K_d$ (nM)."

The ability of purified humanized variants to block internalization of tau was determined by cell internalization assays. An internalization assay employing fluorescence activated cell sorting (FACS) was performed to evaluate the ability of various antibodies to block neuronal internalization of tau. Antibodies that block internalization likely block transmission of tau. pHrodo-labeled 4R0N human tau P301L soluble oligomer (1.5 μg/mL final concentration) was preincubated with humanized variants (dose titration: 80 μg/mL starting concentration followed by 4-fold serial dilutions) for 30 min at room temperature in cell culture media. Tau/antibody mixture was then added to B103 neuroblastoma cell lines at 500,000 cells/ml final concentration and incubated for 3-4 hrs at 37° C. in a tissue culture incubator (5% $CO_2$). Cells were then washed 3× with culture media, followed by 10 minutes culture media incubation, and washed 2× with FACS buffer (1% FBS in PBS). Cells were resuspended in 100 μL FACS buffer and Texas Red mean fluorescence intensity measured by FACS LSR II. Texas red fluorescence from pHrodo is activated by low pH associated with endolysosomal compartments upon internalization. Because FACS detects cells and pHrodo only fluoresces upon internalization, only tau internalized by the cells is detected. The lower the mean fluorescence intensity, the lower the amount of internalized tau and higher blocking activity of the antibody tested. Results are presented in in Table 9.

TABLE 9

Biophysical/Expression Characteristics, Affinity, and Internalization Assay Results for 3D6 Humanized Variants

| Antibody Name | | Biophysical/Expression Characteristics | | | Affinity | | | Inhibition of cell based internalization (at 133 nM antibody concentration, % of inhibition of maximal fluorescent signal) |
|---|---|---|---|---|---|---|---|---|
| Heavy Chain | Light Chain | Thermostability (° C.) | Expression titer (mg/L) | % Monomer | $k_{on}$ $(M^{-1}s^{-1})$ | $k_{off}$ $(s^{-1})$ | $K_d$ (nM) | |
| Hu3D6VHvb1 (SEQ ID NO: 76) | Hu3D6VLvb1 (SEQ ID NO: 83) | 69.4 | 176 | 96 | 1.40E+06 | 9.00E−04 | 0.64 | 80.0 |
| Hu3D6VHvb2 (SEQ ID NO: 77) | Hu3D6VLvb2 (SEQ ID NO: 84) | 80.4 | 478 | 98 | 1.50E+06 | 5.70E−05 | 0.04 | 84.9 |
| Hu3D6VHvb2 (SEQ ID NO: 77) | Hu3D6VLvb3 (SEQ ID NO: 85) | 83.5 | 435 | 100 | 1.60E+06 | 3.00E−04 | 0.19 | 85.0 |
| Hu3D6VHvb3 (SEQ ID NO: 78) | Hu3D6VLvb2 (SEQ ID NO: 84) | 80.8 | 528 | 100 | 1.40E+06 | 1.50E−03 | 1.07 | 71.2 |
| Hu3D6VHvb3 (SEQ ID NO: 78) | Hu3D6VLvb3 (SEQ ID NO: 85) | 83.15 | 529 | 100 | 1.60E+06 | 1.80E−03 | 1.13 | 72.1 |
| Hu3D6VHvb4 (SEQ ID NO: 79) | Hu3D6VLvb2 (SEQ ID NO: 84) | 81.3 | 557 | 98 | 6.90E+05 | 2.90E−03 | 4.20 | 61.0 |
| Hu3D6VHvb4 (SEQ ID NO: 79) | Hu3D6VLvb3 (SEQ ID NO: 85) | 83.5 | 575 | 100 | 9.10E+05 | 3.40E−03 | 3.74 | 49.0 |
| Hu3D6VHvb5 (SEQ ID NO: 80) | Hu3D6VLvb2 (SEQ ID NO: 84) | 80.6 | 597 | 100 | 1.80E+06 | 2.60E−03 | 1.44 | 67.2 |
| Hu3D6VHvb5 (SEQ ID NO: 80) | Hu3D6VLvb3 (SEQ ID NO: 85) | 82.9 | 612 | 100 | 2.00E+06 | 2.80E−03 | 1.40 | 67.7 |
| Hu3D6VHvb6 (SEQ ID NO: 90) | Hu3D6VLvb2 (SEQ ID NO: 84) | 79.9 | 395 | 100 | 3.45E+06 | 3.69E−04 | 0.107 | 76.3 |
| Hu3D6VHvb6 (SEQ ID NO: 90) | Hu3D6VLvb3 (SEQ ID NO: 85) | 82.5 | 350 | 100 | 3.54E+06 | 5.38E−04 | 0.152 | 70.0 |
| Hu3D6VHvb7 (SEQ ID NO: 91) | Hu3D6VLvb2 (SEQ ID NO: 84) | 80.6 | 478 | 100 | 3.09E+06 | 7.79E−04 | 0.252 | 74.5 |
| Hu3D6VHvb7 (SEQ ID NO: 91) | Hu3D6VLvb3 (SEQ ID NO: 85) | 83.0 | 447 | 99 | 3.69E+06 | 7.70E−04 | 0.209 | 66.0 |

Listing of Sequences

P10636-8

(SEQ ID NO: 1)

MAEPRQEFEVMEDHAGTYGLGDRKDQGGYTMHQDQEGDTDAGLKESPLQTPTEDGSE

EPGSETSDAKSTPTAEDVTAPLVDEGAPGKQAAAQPHTEIPEGTTAEEAGIGDTPSLEDE

AAGHVTQARMVSKSKDGTGSDDKKAKGADGKTKIATPRGAAPPGQKGQANATRIPAK

TPPAPKTPPSSGEPPKSGDRSGYSSPGSPGTPGSRSRTPSLPTPPTREPKKVAVVRTPPKSP

SSAKSRLQTAPVPMPDLKNVKSKIGSTENLKHQPGGGKVQIINKKLDLSNVQSKCGSKD

NIKHVPGGGSVQIVYKPVDLSKVTSKCGSLGNIHHKPGGGQVEVKSEKLDFKDRVQSKI

GSLDNITHVPGGGNKKIETHKLTFRENAKAKTDHGAEIVYKSPVVSGDTSPRHLSNVSST

GSIDMVDSPQLATLADEVSASLAKQGL

P10636-7

(SEQ ID NO: 2)

MAEPRQEFEVMEDHAGTYGLGDRKDQGGYTMHQDQEGDTDAGLKESPLQTPTEDGSE

EPGSETSDAKSTPTAEAEEAGIGDTPSLEDEAAGHVTQARMVSKSKDGTGSDDKKAKG

ADGKTKIATPRGAAPPGQKGQANATRIPAKTPPAPKTPPSSGEPPKSGDRSGYSSPGSPG

TPGSRSRTPSLPTPPTREPKKVAVVRTPPKSPSSAKSRLQTAPVPMPDLKNVKSKIGSTEN

LKHQPGGGKVQIINKKLDLSNVQSKCGSKDNIKHVPGGGSVQIVYKPVDLSKVTSKCGS

LGNIHHKPGGGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVSASLAKQGL

P10636-6 (4RON human tau)

(SEQ ID NO: 3)

MAEPRQEFEVMEDHAGTYGLGDRKDQGGYTMHQDQEGDTDAGLKAEEAGIGDTPSLE

DEAAGHVTQARMVSKSKDGTGSDDKKAKGADGKTKIATPRGAAPPGQKGQANATRIP

AKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIINKKLDLSNVQSKCGS

KDNIKHVPGGGSVQIVYKPVDLSKVTSKCGSLGNIHHKPGGGQVEVKSEKLDFKDRVQ

SKIGSLDNITHVPGGGNKKIETHKLTFRENAKAKTDHGAEIVYKSPVVSGDTSPRHLSNV

SSTGSIDMVDSPQLATLADEVSASLAKQGL

P10636-5

(SEQ ID NO: 4)

MAEPRQEFEVMEDHAGTYGLGDRKDQGGYTMHQDQEGDTDAGLKESPLQTPTEDGSE

EPGSETSDAKSTPTAEDVTAPLVDEGAPGKQAAAQPHTEIPEGTTAEEAGIGDTPSLEDE

AAGHVTQARMVSKSKDGTGSDDKKAKGADGKTKIATPRGAAPPGQKGQANATRIPAK

TPPAPKTPPSSGEPPKSGDRSGYSSPGSPGTPGSRSRTPSLPTPPTREPKKVAVVRTPPKSP

SSAKSRLQTAPVPMPDLKNVKSKIGSTENLKHQPGGGKVQIVYKPVDLSKVTSKCGSLG

NIHHKPGGGQVEVKSEKLDFKDRVQSKIGSLDNITHVPGGGNKKIETHKLTFRENAKAK

TDHGAEIVYKSPVVSGDTSPRHLSNVSSTGSIDMVDSPQLATLADEVSASLAKQGL

P10636-4

(SEQ ID NO: 5)

MAEPRQEFEVMEDHAGTYGLGDRKDQGGYTMHQDQEGDTDAGLKESPLQTPTEDGSE

EPGSETSDAKSTPTAEAEEAGIGDTPSLEDEAAGHVTQARMVSKSKDGTGSDDKKAKG

ADGKTKIATPRGAAPPGQKGQANATRIPAKTPPAPKTPPSSGEPPKSGDRSGYSSPGSPG

TPGSRSRTPSLPTPPTREPKKVAVVRTPPKSPSSAKSRLQTAPVPMPDLKNVKSKIGSTEN

-continued

LKHQPGGGKVQIVYKPVDLSKVTSKCGSLGNIHHKPGGGQVEVKSEKLDFKDRVQSKI

GSLDNITHVPGGGNKKIETHKLTFRENAKAKTDHGAEIVYKSPVVSGDTSPRHLSNVSST

GSIDMVDSPQLATLADEVSASLAKQGL

P10636-2

(SEQ ID NO: 6)

MAEPRQEFEVMEDHAGTYGLGDRKDQGGYTMHQDQEGDTDAGLKAEEAGIGDTPSLE

DEAAGHVTQARMVSKSKDGTGSDDKKAKGADGKTKIATPRGAAPPGQKGQANATRIP

AKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIVYKPVDLSKVTSKCGS

LGNIHHKPGGGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVSASLAKQGL

Murine 3D6 VH amino acid sequence:

SEQ ID NO: 7

EVQLQQSGADLVRPGALVKLSCKASGFNIKDYYLHWVRQRPEQGLEWIGWIDPENGDT

VYDPKFQGKATITADTSSNTAYLQLGSLTSEDTAVYFCSTLDFWGQGTTLTVSS;

Kabat/Chothia HCDR1:

SEQ ID NO: 8

GFNIKDYYLH;

Kabat HCDR2:

SEQ ID NO: 9

WIDPENGDTVYDPKFQG;

Kabat HCDR3:
LDF

Murine 3D6 VL amino acid sequence:

SEQ ID NO: 11

DVVMTQTPLTLSVTIGQPASISCKSSQSLLDSDGKTYLNWLLQRPGQSPKRLIYLVSKLD

SGVPDRFTGSGSGTDFTLKISRVEAEDLGVYYCWQGTHFPYTFGGGTKLEIKR;

Murine Kabat LCDR1:

SEQ ID NO: 12

KSSQSLLDSDGKTYLN;

Murine Kabat LCDR2:

SEQ ID NO: 13

LVSKLDS;

Murine Kabat LCDR3:

SEQ ID NO: 14

WQGTHFPYT;

hu3D6VHv1:

SEQ ID NO: 15

EVQLVQSGAEVVRPGALVKVSCKASGFNIKDYYLHWVRQAPEQGLEWIGWIDPENGDT

VYDPKFQGKATITADTSTNTAYLQLSSLTSEDTAVYFCSTLDFWGQGTLVTVSS;

hu3D6VHv2:

SEQ ID NO: 16

EVQLVQSGAEVKKPGASVKVSCKVSGFNIKDYYLHWVRQAPEQGLEWMGWIDPENGD

TVYDPKFQGRVTITADTSTNTAYMELSSLTSEDTAVYYCSTLDFWGQGTLVTVSS;

hu3D6VHv1b:

SEQ ID NO: 17

EVQLVQSGAEVVRPGALVKISCKASGFNIKDYYLHWVRQRPEQGLEWIGWIDPENGDT

VYDPKFQGKATITADTSTNTAYLQLGSLTSEDTAVYFCSTLDFWGQGTLVTVSS;

hu3D6VHv1bA11:

SEQ ID NO: 18

EVQLVQSGAEVVKPGATVKISCKASGFNIKDYYLHWVRQRPGQGLEWIGWIDPENGDT

VYDPKFQGRATITADTSTDTAYLQLGSLTSEDTAVYFCSTLDFWGQGTLVTVSS;

-continued hu3D6VHv5:
SEQ ID NO: 19
EVQLVQSGAEVVKPGATVKISCKASGFTIKDYYLHWVRQRPGQGLEWIGWIDPEDGDT

VYAPKFQGRATITADTSTDTAYLQLGSLTSEDTAVYFCSTLDFWGQGTLVTVSS;

hu3D6VLv1:
SEQ ID NO: 20
DVVMTQSPLSLSVTLGQPASISCKSSQSLLDSDGKTYLNWLLQRPGQSPKRLIYLVSKLD

SGVPDRFSGSGSGTDFTLKISRVEAEDVGVYYCWQGTHFPYTFGGGTKLEIKR;

hu3D6VLv2:
SEQ ID NO: 21
DVVMTQSPLSLPVTLGQPASISCKSSQSLLDSDGKTYLNWLLQRPGQSPRRLIYLVSKLD

SGVPDRFSGSGSGTDFTLKISRVEAEDVGVYYCWQGTHFPYTFGGGTKLEIKR;

hu3D6VLv3:
SEQ ID NO: 22
DVVMTQSPLSLPVTLGQPASISCKSSQSLLDSDGKTYLNWLLQRPGQSPRRLIYLVSKLD

SGVPSRFSGSGSGTDFTLKISRVEAEDVGVYYCWQGTHFPYTFGGGTKLEIKR;

hu3D6VLv4:
SEQ ID NO: 23
DIVMTQTPLSLSVTIGQPASISCKSSQSLLDSDGKTYLNWLLQKPGQSPKRLIYLVSKLDS

GVPDRFSGSGSGTDFTLKISRVEAEDVGVYYCWQGTHFPYTFGGGTKLEIKR;

heavy chain variable acceptor Acc.# BAC01986.1
SEQ ID NO: 24
QVQLQQSGAEVKKPGSSVKVSCKASGGTFGSYAISWVRQAPGQGLEWMGRIIPILGIAT

YAQKFQGRVTITADKSTSTAYMDLSSLRSEDTAVYYCARGKGEFEGMDVWGQGTTVT

VSS;

heavy chain variable acceptor Acc.# IMGT# IGHV1-69-2*01
SEQ ID NO: 25
EVQLVQSGAEVKKPGATVKISCKVSGYTFTDYYMHWVQQAPGKGLEWMGLVDPEDG

ETIYAEKFQGRVTITADTSTDTAYMELSSLRSEDTAVYYCAT;

heavy chain variable acceptor Acc.# IMGT#IGKJ1*01
SEQ ID NO: 26
QHWGQGTLVTVSS;

light chain variable acceptor Acc. # IMGT#IGKV2-30*02
Acc. # IMGT#IGKV2-30*02
SEQ ID NO: 27
DVVMTQSPLSLPVTLGQPASISCRSSQSLVHSDGNTYLNWFQQRPGQSPRRLIYKVSNRD

SGVPDRFSGSGSGTDFTLKISRVEAEDVGVYYCMQGTHWP;

light chain variable acceptor Acc. # IMGT#IGKJ2*01
SEQ ID NO: 28
YTFGQGTKLEIK;

Light chain variable acceptor Acc. # AAZ09048.1
SEQ ID NO: 29
DVVMTQSPLSLTVTLGQPASISCRSSQSLVYSDGNTYLNWFQQRPGQSPRRLIYRVSHW

DSGVPDRFSGSGSGTDFTLKISRVEAEDVGVYYCMQGTYWPLTFGQGTKLEIK;

Murine 3D6 VH nucleic acid sequence:
SEQ ID NO: 30
GAGGTTCAGCTGCAGCAGTCTGGGGCTGACCTTGTGAGGCCAGGGGCCTTAGTCAA

GTTGTCCTGCAAAGCTTCTGGCTTCAACATTAAAGACTACTATTTGCACTGGGTGAG

GCAGAGGCCTGAACAGGGCCTGGAGTGGATTGGATGGATTGATCCTGAGAATGGTG

ATACTGTATATGACCCGAAGTTCCAGGGCAAGGCCACTATAACAGCAGACACATCC

TCCAATACAGCCTACCTGCAGCTCGGCAGCCTGACATCTGAGGACACTGCCGTCTAT

TTCTGTTCTACCCTTGACTTCTGGGGCCAAGGCACCACTCTCACAGTCTCCTCA;

-continued

Murine 3D6 VL nucleic acid sequence:

SEQ ID NO: 31

GATGTTGTGATGACCCAGACTCCACTCACTTTGTCGGTTACCATTGGACAACCAGCC

TCCATCTCTTGCAAGTCAAGTCAGAGCCTCTTAGATAGTGATGGAAAGACATATTTG

AATTGGTTGTTACAGAGGCCAGGCCAGTCTCCAAAGCGCCTAATCTATCTGGTGTCT

AAACTGGACTCTGGAGTCCCTGACAGGTTCACTGGCAGTGGATCAGGGACAGATTTC

ACACTGAAAATCAGCAGAGTGGAGGCTGAGGATTTGGGAGTTTATTATTGCTGGCA

AGGTACACATTTTCCGTACACGTTCGGAGGGGGGACCAAGCTGGAAATAAAACGT;

Murine CDR-H1 Kabat

SEQ ID NO: 32

DYYLH;

Murine CDR-H1 Chothia

SEQ ID NO: 33

GFNIKDY;

Murine CDR-H2 Chothia

SEQ ID NO: 34

DPENGD;

Murine CDR-H2 AbM

SEQ ID NO: 35

WIDPENGDTV;

Murine CDR-L1 Contact

SEQ ID NO: 36

KTYLNWL;

Murine CDR-L2 Contact

SEQ ID NO: 37

RLIYLVSKLD;

Murine CDR-L3 Contact

SEQ ID NO: 38

WQGTHFPY;

Murine CDR-H1 Contact

SEQ ID NO: 39

KDYYLH;

Murine CDR-H2 Contact

SEQ ID NO: 40

WIGWIDPENGDTV;

Murine CDR-H3 Contact

SEQ ID NO: 41

STLD;

Alternate Kabat-Chothia CDR-H1

SEQ ID NO: 42

GFTIKDYYLH;

Alternate Kabat CDR-H2

SEQ ID NO: 43

WIDPEDGDTVYAPKFQG;

consensus VH amino acid sequence from FIG. 2 of PCT/IB2017/052544

SEQ ID NO: 44

EVQLVQSGAEVVXPGALVKISCKASGFNIKDYYLHWVRQRPEQGLEWIGWIDPENGDT

VYDPKFQGXATITADTSTNTAYLQLGSLTSEDTAVYFCSTLDFWGQGTLVTVSS;

consensus VL amino acid sequence of FIG. 3 of PCT/IB2017/052544

SEQ ID NO: 45

DVVMTQSPLSLSVTLGQPASISCKSSQSLLDSDGKTYLNWLLQRPGQSPKRLIYLVSKLD

SGVPDRFSGSGSGTDFTLKISRVEAEDVGVYYCWQGTHFPYTFGGGTKLEIKR;

-continued hu3D6VHv1bA11B6G2:

SEQ ID NO: 46

EVQLVQSGAEVVKPGATVKISCKASGFTIKDYYLHWVRQRPGKGLEWIGWVDPEDGDT

VYAPKFQGRATITADTSTDTAYLELGSLTSEDTAVYFCSTLDFWGQGTLVTVSS;

hu3D6VHv1bA11B6H3:

SEQ ID NO: 47

EVQLVQSGAEVVKPGATVKISCKASGFTIKDYYLHWVRQRPGKGLEWIGWIDPEDGDT

VYAPKFQGRATITADTSTDTAYLELGSLTSEDTAVYFCSTLDFWGQGTLVTVSS;

hu3D6VHv1c:

SEQ ID NO: 48

EVQLVQSGAEVKRPGALVKISCKASGFNFKDYYLHWVRQRPEQGLEWMGWIDPENGD

TVYDEKFQGRVTITADTSTNTAYLQLGSLTSEDTAVYFCSTLDFWGQGTLVTVSS;

hu3D6VHv1d:

SEQ ID NO: 49

EVQLVQSGAEVKRPGALVKISCKASGYTFTDYYLHWVRQRPEQGLEWMGWVDPEDGD

TVYAEKFQGRVTITADTSTNTAYLQLGSLTSEDTAVYFCSTLDFWGQGTLVTVSS;

hu3D6VHv1e:

SEQ ID NO: 50

EVQLVQSGADVVKPGALVKISCKASGFTIKDYYLHWVRQRPEQGLEWIGWIDPENGDT

VYAEKFQGRVTITADTSTNTAYLELGSLTSEDTAVYFCSTLDFWGQGTTLTVSS;

hu3D6VHv1f:

SEQ ID NO: 51

EVQLVQSGADVVKPGALVKISCKASGFTIKDYYLHWVRQRPGQGLEWIGWVDPEDGD

TVYAEKFQGRVTITADTSTDTAYMELGSLTSEDTAVYFCSTLDYWGQGTTLTVSS;

hu3D6VHv3:

SEQ ID NO: 52

EVQLVQSGAEVKKPGATVKISCKVSGFNIKDYYLHWVRQAPGKGLEWMGWIDPENGD

TVYDPKFQGRVTITADTSTDTAYMELSSLRSEDTAVYYCSTLDFWGQGTLVTVSS;

hu3D6VHv3b:

SEQ ID NO: 53

EVQLVQSGAEVKKPGALVKISCKVSGYNFKDYYLHWVRQAPGKGLEWMGWIDPENG

DTVYDEKFQGRVTITADTSTNTAYMELGSLRSEDTAVYYCSTLDFWGQGTLVTVSS;

hu3D6VHv3c:

SEQ ID NO: 54

EVQLVQSGAEVKKPGALVKISCKVSGYTFTDYYLHWVRQAPGKGLEWMGWVDPEDG

DTVYAEKFQGRVTITADTSTNTAYMELGSLRSEDTAVYYCSTLDFWGQGTLVTVSS;

hu3D6VHv4:

SEQ ID NO: 55

EVQLVQSGAEVVKPGATVKISCKVSGFNIKDYYLHWVRQRPGKGLEWIGWIDPENGDT

VYDPKFQGKATITADTSTNTAYLELGSLTSEDTAVYYCSTLDFWGQGTLVTVSS;

hu3D6VHv4b:

SEQ ID NO: 56

EVQLVQSGAEVVKPGALVKISCKVSGYNFKDYYLHWVRQRPGKGLEWMGWIDPENGD

TVYDEKFQGRVTITADTSTDTAYLELGSLTSEDTAVYYCSTLDFWGQGTLVTVSS;

hu3D6VHv4c:

SEQ ID NO: 57

EVQLVQSGAEVVKPGALVKISCKVSGYTFTDYYLHWVRQRPGKGLEWMGWVDPEDG

DTVYAEKFQGRVTITADTSTDTAYLELGSLTSEDTAVYYCSTLDFWGQGTLVTVSS;

Alternate Kabat-Chothia CDR-H1 (as in hu3D6VH1c).

SEQ ID NO: 58

GFNFKDYYLH;

Alternate Kabat-Chothia CDR-H1, (as in hu3D6VHv1d, hu3D6VHv3c, and hu3D6VHv4c).

SEQ ID NO: 59

GYTFTDYYLH;

-continued

Alternate Kabat-Chothia CDR-H1 (as in hu3D6VHv3b and hu3D6VHv4b)

SEQ ID NO: 60
GYNFKDYYLH;

Alternate Kabat CDR-H2 (as in hu3D6VHv1bA11B6G2).

SEQ ID NO: 61
WVDPEDGDTVYAPKFQG;

Alternate Kabat CDR-H2 (as in hu3D6VHv1c, hu3D6VHv3b, AND hu3D6VHv4b.

SEQ ID NO: 62
WIDPENGDTVYDEKFQG,

Alternate Kabat CDR-H2 as in hu3D6VHv1d, hu3D6VHv1f, hu3D6VHv3c, and hu3D6VHv4c).

SEQ ID NO: 63
WVDPEDGDTVYAEKFQG;

Alternate Kabat CDR-H2 (as in hu3D6VHv1e).

SEQ ID NO: 64
WIDPENGDTVYAEKFQG;

Alternate Kabat CDR-H3 (as in hu3D6VHv1f)

SEQ ID NO: 65
LDY;

heavy chain variable region of the mouse 6A10 antibody.

SEQ ID NO: 66
EVQLQQSGAELVRSGASVKLSCTASGLNIKDYYIHWVKQRPEQGLEWIGWIDPENDDTE

YAPKFQGRATLTTDTSSNTAYLQLSSLTSEDTAVYYCTPLDYWGQGTSVTVSS;

Kabat/Chothia composite CDR-H1 of the mouse 6A10 antibody.

SEQ ID NO: 67
GLNIKDYYIH;

Kabat CDR-H2 of the mouse 6A10 antibody.

SEQ ID NO: 68
WIDPENDDTEYAPKFQG;

Kabat CDR-H3 of the mouse 6A10 antibody

SEQ ID NO: 69
LDY;

Mus VH structure template (PDB#1CR9_H)

SEQ ID NO: 70
KVKLQQSGAELVRSGASVKLSCTASGFNIKDYYIQWVKQRPEQGLEWIGWIDPENGNSEYAPRF

QGKATMTADTLSNTAYLQLSSLTSEDTAVYYCNADLHDYWGQGTTLTVSS;

consensus VH amino acids equence from FIGS. 4A and 4B of PCT/IB2017/052544

SEQ ID NO: 71
EVQLVQSGAEVVKPGALVKISCKASGFNIKDYYLHWVRQRPGQGLEWIGWIDPENGDT

VYDPKFQGRVTITADTSTNTAYLELGSLTSEDTAVYFCSTLDFWGQGTLVTVSS;

heavy chain of chimeric 3D6 antibody

SEQ ID NO: 72
EVQLQQSGADLVRPGALVKLSCKASGFNIKDYYLHWVRQRPEQGLEWIGWIDPENGDT

VYDPKFQGKATITADTSSNTAYLQLGSLTSEDTAVYFCSTLDFWGQGTTLTVSSASTKG

PSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYSKLTVDKSRWQ

QGNVFSCSVMHEALHNHYTQKSLSLSPGK;

-continued light chain of chimeric 3D6 antibody

SEQ ID NO: 73

DVVMTQTPLTLSVTIGQPASISCKSSQSLLDSDGKTYLNWLLQRPGQSPKRLIYLVSKLD

SGVPDRFTGSGSGTDFTLKISRVEAEDLGVYYCWQGTHFPYTFGGGTKLEIKRTVAAPS

VFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC;

amino acid sequence of heavy chain variable structural model Acc.# 5MYX-VH_mSt

SEQ ID NO: 74

EVQLQQSGAELVRPGSSVKISCKASGYIFNNYWINWVKQRPGQGLEWIGQIYPGDGDTN

YNGKFKGKATLTADKSSSTAYMQLSSLTSEDSAVYFCAREGYIVYWGQGTLVTVSA;

amino acid sequence of heavy chain variable acceptor Acc.# 2RCS-VH_huFrwk

SEQ ID NO: 75

QVQLQQSGAELVKPGASVKLSCTASGFNIKDTYMHWVKQRPEQGLEWIGRIDPANGNT

KYDPKFQGKATITADTSSNTAYLQLSSLTSEDTAVYYCASYYGIYWGQGTTLTVSS;

amino acid sequence of heavy chain variable region of the humanized 3D6 antibody hu3D6VHvb1

SEQ ID NO: 76

QVQLQQSGAELVKPGASVKLSCTASGFNIKDYYLHWVKQRPEQGLEWIGWIDPENGDT

VYDPKFQGKATITADTSSNTAYLQLSSLTSEDTAVYFCSTLDFWGQGTTLTVSS;

amino acid sequence of heavy chain variable region of the humanized 3D6 antibody hu3D6VHvb2

SEQ ID NO: 77

EVQLVQSGAEVVKPGASVKISCKASGFNIKDYYLHWVRQRPGKGLEWIGWIDPENGDT

VYDPKFQGRATITADTSTDTAYLELSSLTSEDTAVYFCSTLDFWGQGTLVTVSS;

amino acid sequence of heavy chain variable region of the humanized 3D6 antibody hu3D6VHvb3

SEQ ID NO: 78

EVQLVQSGAEVVKPGATVKISCKASGFNIKDYYLHWVRQRPGKGLEWIGWIDPENGDTI

YDPKFQGRATITADTSTDTAYMELSSLRSEDTAVYYCSTLDFWGQGTLVTVSS;

amino acid sequence of heavy chain variable region of the humanized 3D6 antibody hu3D6VHvb4

SEQ ID NO: 79

EVQLVQSGAEVVKPGATVKISCKASGFTIKDYYLHWVRQRPGKGLEWIGWIDPENGDTI

YDPKFQGRVTITADTSTDTAYMELSSLRSEDTAVYYCSTLDFWGQGTLVTVSS;

amino acid sequence of heavy chain variable region of the humanized 3D6 antibody hu3D6VHvb5

SEQ ID NO: 80

EVQLVQSGAEVVKPGATVKISCKASGFTIKDYYLHWVRQRPGKGLEWIGWIDPEDGETI

YDPKFQGRVTITADTSTDTAYMELSSLRSEDTAVYYCSTLDFWGQGTLVTVSS;

amino acid sequence of light chain variable structural model Acc.# 5MYX-VL_mSt

SEQ ID NO: 81

DVVLTQTPLTLSVTIGQPASISCKSSQSLLYSNGKTYLNWLLQRPGQSPKRLIYVVSKLDS

GVPDRFTGSGSGTDFTLKISRVEAEDLGVYYCVQGTHFPFTFGSGTKLEIK;

amino acid sequence of light chain variable acceptor Acc.# ARX71335-VL_huFrwk

SEQ ID NO: 82

DVVMTQTPLTLSVTIGQPASISCKSSQSLLYSNGKTYLNWLLQRPGQSPKRLIYLVSKLD

SGVPDRFSGSGSGTDFTLKISRVEAEDLGVHYCEQGTHFPLTFGAGTKLELK;

amino acid sequence of light chain variable region of the humanized 3D6 antibody hu3D6VLvb1

SEQ ID NO: 83

DVVMTQTPLTLSVTIGQPASISCKSSQSLLDSDGKTYLNWLLQRPGQSPKRLIYLVSKLD

SGVPDRFSGSGSGTDFTLKISRVEAEDLGVHYCWQGTHFPYTFGAGTKLELKR;

-continued amino acid sequence of light chain variable region of the humanized 3D6 antibody hu3D6VLvb2

SEQ ID NO: 84

DVVMTQSPLSLSVTLGQPASISCKSSQSLLDSDGKTYLNWLLQRPGQSPKRLIYLVSKLD

SGVPDRFSGSGSGTDFTLKISRVEAEDVGVYYCWQGTHFPYTFGAGTKLEIKR;

amino acid sequence of light chain variable region of the humanized 3D6 antibody hu3D6VLvb3

SEQ ID NO: 85

DVVMTQSPLSLSVTLGEPASISCRSSQSLLDSDGKTYLNWLQQRPGQSPRRLIYLVSKLD

SGVPDRFSGSGSGTDFTLKISRVEAEDVGVYYCWQGTHFPYTFGQGTKLEIKR;

amino acid sequence of an alternate Kabat-Chothia Composite CDR-H1 of a humanized 3D6 antibody (as in hu3D6VHvb4 and hu3D6VHvb5)

SEQ ID NO: 86

GFTIKDYYLH;

amino acid sequence of an alternate Kabat CDR-H2 of a humanized 3D6 antibody (as in hu3D6VHvb3 and hu3D6VHvb4)

SEQ ID NO: 87

WIDPENGDTIYDPKFQG;

amino acid sequence of an alternate Kabat CDR-H2 of a humanized 3D6 antibody (as in hu3D6VHvb5)

SEQ ID NO: 88

WIDPEDGETIYDPKFQG;

amino acid sequence of an alternate Kabat CDR-L1 of a humanized 3D6 antibody (as in hu3D6VLvb3)

SEQ ID NO: 89

RSSQSLLDSDGKTYLN;

amino acid sequence of heavy chain variable region of the humanized 3D6 antibody hu3D6VHvb6

SEQ ID NO: 90

EVQLVQSGAEVVKPGATVKISCKASGFTIKDYYLHWVRQRPGKGLEWIGWIDPEDGET

VYDPKFQGRVTITADTSTDTAYMELSSLRSEDTAVYFCSTLDFWGQGTLVTVSS;

amino acid sequence of heavy chain variable region of the humanized 3D6 antibody hu3D6VHvb7

SEQ ID NO: 91

EVQLVQSGAEVVKPGATVKISCKASGFTIKDYYLHWVRQRPGKGLEWIGWIDPEDGET

VYDPKFQGRVTITADTSTDTAYMELSSLRSEDTAVYYCSTLDFWGQGTLVTVSS;

amino acid sequence of an alternate Kabat CDR-H2 of a humanized 3D6 antibody (as in hu3D6VHvb6 and hu3D6VHvb7)

SEQ ID NO: 92

WIDPEDGETVYDPKFQG;

a nucleic acid sequence encoding the heavy chain variable region of the humanized 3D6 antibody hu3D6VHvb1

SEQ ID NO: 93

CAAGTGCAGCTGCAGCAGAGCGGGGCAGAATTGGTCAAGCCCGGAGCGTCAGTGAA

GCTGAGCTGCACCGCCTCCGGCTTCAACATCAAAGACTACTATCTTCACTGGGTCAA

GCAACGGCCTGAACAGGGCCTGGAGTGGATTGGTTGGATCGACCCAGAAAACGGCG

ACACCGTGTACGATCCGAAGTTTCAGGGGAAGGCCACCATCACTGCTGATACGTCCT

CGAACACCGCCTACCTCCAACTGAGCTCCCTGACTTCCGAGGACACTGCCGTGTACT

TCTGTTCCACCCTGGACTTCTGGGGACAGGGAACTACCCTCACCGTGTCCTCGGCCA

GCACTAAGGGGCCTAGCGTCTTTCCGCTGGCCCCGTCCTCCAAGTCCACTTCGGGTG

GAACCGCGGCACTGGGGTGCCTCG;

a nucleic acid sequence encoding the heavy chain variable region of the humanized 3D6 antibody hu3D6VHvb2

SEQ ID NO: 94

GAAGTGCAGCTCGTGCAGTCCGGTGCCGAAGTCGTGAAACCGGGAGCCAGCGTGAA

GATTAGCTGCAAGGCCTCAGGGTTCAACATCAAGGACTATTACCTTCACTGGGTCAG

ACAGCGGCCTGGAAAGGGCTTGGAGTGGATCGGATGGATTGACCCCGAGAACGGCG

-continued

ACACCGTGTACGATCCGAAGTTTCAGGGCCGCGCAACCATCACTGCTGACACCTCCA

CCGATACCGCGTACCTGGAACTCTCGAGCCTGACTTCCGAGGATACGGCCGTGTACT

TCTGTTCCACCCTGGACTTCTGGGGACAAGGGACTCTGGTCACCGTGTCCTCGGCCA

GCACTAAGGGGCCTAGCGTCTTTCCGCTGGCCCCGTCCTCCAAGTCCACTTCGGGTG

GAACCGCGGCACTGGGGTGCCTCG;

a nucleic acid sequence encoding the heavy chain variable region of the humanized 3D6 antibody hu3D6VHvb3

SEQ ID NO: 95

GAGGTGCAACTGGTGCAGTCCGGAGCCGAAGTCGTGAAGCCGGGAGCCACCGTGAA

GATTTCGTGCAAAGCGTCAGGGTTTAACATCAAGGACTACTATCTGCACTGGGTCCG

CCAGAGGCCCGGGAAGGGCCTCGAGTGGATCGGTTGGATCGACCCTGAAAACGGCG

ACACCATCTACGATCCAAAGTTCCAGGGCAGAGCCACTATTACCGCTGACACGAGC

ACCGATACTGCATACATGGAATTGTCCTCCCTGCGGTCCGAGGATACTGCCGTGTAC

TACTGTAGCACCCTGGACTTCTGGGGACAGGGAACCCTTGTGACCGTGTCGTCCGCC

AGCACTAAGGGGCCTAGCGTCTTTCCGCTGGCCCCGTCCTCCAAGTCCACTTCGGGT

GGAACCGCGGCACTGGGGTGCCTCG;

a nucleic acid sequence encoding the heavy chain variable region of the humanized 3D6 antibody hu3D6VHvb4

SEQ ID NO: 96

GAGGTGCAGCTCGTGCAGTCCGGTGCTGAAGTCGTGAAGCCCGGCGCAACTGTGAA

GATTAGCTGCAAGGCCTCAGGGTTCACGATCAAGGACTACTATCTGCACTGGGTCCG

CCAACGGCCAGGAAAGGGACTGGAGTGGATCGGATGGATCGATCCTGAAAACGGCG

ACACCATCTACGACCCGAAATTTCAGGGGAGAGTGACCATTACCGCCGATACCTCC

ACCGACACTGCGTACATGGAACTGTCCAGCCTTCGGTCCGAGGACACCGCCGTGTAC

TACTGTTCGACCCTGGATTTCTGGGGACAGGGCACTCTCGTGACTGTGTCGTCCGCC

AGCACTAAGGGGCCTAGCGTCTTTCCGCTGGCCCCGTCCTCCAAGTCCACTTCGGGT

GGAACCGCGGCACTGGGGTGCCTCG;

a nucleic acid sequence encoding the heavy chain variable region of the humanized 3D6 antibody hu3D6VHvb5

SEQ ID NO: 97

GAAGTGCAACTGGTGCAGTCCGGCGCAGAAGTCGTGAAGCCTGGAGCCACCGTGAA

GATCAGCTGCAAGGCCTCCGGCTTCACCATCAAAGACTACTACTTGCACTGGGTCAG

ACAGCGCCCAGGAAAGGGTCTGGAATGGATTGGATGGATTGACCCCGAGGACGGGG

AGACTATCTACGATCCGAAGTTTCAGGGCCGGGTCACCATCACGGCTGATACCTCGA

CCGACACTGCGTACATGGAACTTTCCTCGCTGCGGTCCGAGGACACCGCCGTGTATT

ACTGTTCCACCCTGGATTTCTGGGGACAGGGGACTCTCGTGACTGTGTCAAGCGCCA

GCACTAAGGGGCCTAGCGTCTTTCCGCTGGCCCCGTCCTCCAAGTCCACTTCGGGTG

GAACCGCGGCACTGGGGTGCCTCG;

a nucleic acid sequence encoding the heavy chain variable region of the humanized 3D6 antibody hu3D6VHvb6

SEQ ID NO: 98

GAAGTGCAACTGGTGCAGTCCGGCGCAGAAGTCGTGAAGCCTGGAGCCACCGTGAA

GATCAGCTGCAAGGCCTCCGGCTTCACCATCAAAGACTACTACTTGCACTGGGTCAG

ACAGCGCCCAGGAAAGGGTCTGGAATGGATTGGATGGATTGACCCCGAGGACGGGG

AGACTGTGTACGATCCGAAGTTTCAGGGCCGGGTCACCATCACGGCTGATACCTCGA

CCGACACTGCGTACATGGAACTTTCCTCGCTGCGGTCCGAGGACACCGCCGTGTATT

TCTGTTCCACCCTGGATTTCTGGGGACAGGGGACTCTCGTGACTGTGTCAAGCGCCA

-continued

GCACTAAGGGGCCTAGCGTCTTTCCGCTGGCCCCGTCCTCCAAGTCCACTTCGGGTG

GAACCGCGGCACTGGGGTGCCTCG;

a nucleic acid sequence encoding the heavy chain variable region of the humanized 3D6 antibody hu3D6VHvb7

SEQ ID NO: 99

GAAGTGCAACTGGTGCAGTCCGGCGCAGAAGTCGTGAAGCCTGGAGCCACCGTGAA

GATCAGCTGCAAGGCCTCCGGCTTCACCATCAAAGACTACTACTTGCACTGGGTCAG

ACAGCGCCCAGGAAAGGGTCTGGAATGGATTGGATGGATTGACCCCGAGGACGGGG

AGACTGTGTACGATCCGAAGTTTCAGGGCCGGGTCACCATCACGGCTGATACCTCGA

CCGACACTGCGTACATGGAACTTTCCTCGCTGCGGTCCGAGGACACCGCCGTGTATT

ACTGTTCCACCCTGGATTTCTGGGGACAGGGGACTCTCGTGACTGTGTCAAGCGCCA

GCACTAAGGGGCCTAGCGTCTTTCCGCTGGCCCCGTCCTCCAAGTCCACTTCGGGTG

GAACCGCGGCACTGGGGTGCCTCG;

a nucleic acid sequence encoding the light chain variable region of the humanized 3D6 antibody hu3D6VLvb1

SEQ ID NO: 100

GATGTCGTGATGACCCAGACGCCGCTGACCCTGTCCGTGACTATCGGCCAGCCCGCG

TCCATTTCGTGCAAGAGCAGCCAGTCCCTGCTGGACTCCGACGGAAAGACCTACCTG

AACTGGCTGTTGCAACGGCCGGGACAGTCACCCAAGCGCCTCATCTATCTGGTGTCC

AAGCTCGACTCGGGAGTGCCTGATAGGTTTTCGGGATCCGGCAGCGGGACCGACTTC

ACCCTGAAAATCTCAAGAGTGGAAGCCGAGGACCTTGGTGTCCATTACTGTTGGCAG

GGTACCCACTTCCCATACACTTTCGGGGCCGGCACTAAGCTCGAACTGAAG;

a nucleic acid sequence encoding the light chain variable region of the humanized 3D6 antibody hu3D6VLvb2

SEQ ID NO: 101

GATGTCGTGATGACCCAGTCGCCGCTGTCCCTGTCCGTGACCCTGGGACAGCCAGCC

TCCATTAGCTGCAAGAGCAGCCAGTCCTTGCTGGACTCAGACGGAAAGACCTATCTG

AACTGGCTGCTGCAAAGGCCCGGCCAGTCCCCGAAGAGACTCATCTACCTCGTGTCG

AAGCTGGACTCCGGCGTGCCTGATCGCTTCTCGGGTTCCGGGTCTGGAACTGACTTC

ACCCTCAAAATCTCACGGGTCGAAGCCGAGGACGTGGGCGTGTACTACTGTTGGCA

GGGTACCCACTTTCCCTACACTTTCGGGGCGGGAACTAAGCTTGAGATCAAG;

a nucleic acid sequence encoding the light chain variable region of the humanized 3D6 antibody hu3D6VLvb3

SEQ ID NO: 102

GATGTCGTGATGACCCAGAGCCCCCTGTCCCTGAGCGTGACTCTGGGGGAACCGGC

CAGCATTTCATGCCGGTCCTCACAATCGCTGCTCGACTCCGACGGAAAGACCTATTT

GAACTGGCTGCAGCAAAGACCAGGACAGTCCCCTCGCCGGCTCATCTACCTGGTGTC

CAAGCTTGACTCGGGCGTGCCGGATAGGTTCTCCGGGTCCGGAAGCGGCACCGACT

TCACTCTGAAAATCTCGCGCGTGGAAGCCGAGGACGTGGGAGTCTACTACTGTTGGC

AGGGTACCCACTTCCCCTACACGTTTGGCCAGGGTACCAAGCTCGAGATCAAG;

amino acid sequence of an exemplary IgG1 heavy chain constant region

SEQ ID NO: 103

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

-continued

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK;

amino acid sequence of an exemplary kappa light chain constant region

SEQ ID NO: 104

RTVAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC;

a nucleic acid sequence encoding an exemplary IgG1 heavy chain constant region

SEQ ID NO: 105

GCCAGCACTAAGGGGCCTAGCGTCTTTCCGCTGGCCCCGTCCTCCAAGTCCACTTCG

GGTGGAACCGCGGCACTGGGGTGCCTCGTGAAGGACTACTTCCCCGAGCCGGTCAC

CGTGTCCTGGAACTCGGGAGCCCTGACCTCCGGAGTGCATACTTTCCCTGCGGTGCT

GCAGTCCTCCGGGCTCTACTCGCTGTCAAGCGTGGTCACCGTCCCGAGCTCATCCCT

GGGTACTCAGACCTACATTTGCAACGTGAACCACAAACCTTCCAACACCAAGGTCG

ACAAGAAAGTGGAGCCTAAGAGCTGCGACAAGACCCACACCTGTCCCCCGTGTCCC

GCCCCTGAGCTGCTGGGCGGCCCCAGCGTGTTCCTCTTCCCGCCTAAGCCGAAGGAC

ACTCTGATGATCTCGAGAACCCCTGAAGTGACCTGTGTGGTGGTGGATGTGTCCCAC

GAGGATCCGGAAGTGAAGTTCAATTGGTACGTGGACGGAGTGGAAGTCCATAACGC

CAAGACCAAGCCCCGCGAGGAACAGTACAACTCAACTTACCGGGTGGTGTCAGTGC

TGACCGTGCTGCACCAAGATTGGCTGAACGGGAAGGAGTACAAGTGCAAAGTCTCC

AACAAGGCGCTGCCGGCCCCCATTGAAAAGACCATCAGCAAGGCTAAGGGCCAGCC

CCGGGAACCACAGGTCTACACCTTGCCCCCTTCCCGGGAGGAAATGACCAAGAACC

AAGTGTCGCTGACGTGCCTGGTCAAGGGCTTTTATCCATCTGACATCGCCGTGGAGT

GGGAAAGCAACGGCCAGCCGGAAAACAACTACAAGACTACCCCGCCTGTGCTGGAC

TCCGACGGCTCGTTCTTCCTGTATTCCAAGCTCACCGTGGATAAGTCCAGATGGCAG

CAGGGCAATGTGTTCAGCTGCAGCGTGATGCATGAGGCCCTGCACAACCACTACAC

TCAGAAATCACTGTCCCTTTCCCCCGGAAAGTAA;

a nucleic acid sequence encoding an exemplary kappa light chain constant region

SEQ ID NO: 106

CGAACTGTGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAGTGTCAC

AGAGCAGGACAGCAAGGACAGCACCTACAGCCTCAGCAGCACCCTGACGCTGAGCA

AAGCAGACTACGAGAAACACAAAGTCTACGCCTGCGAAGTCACCCATCAGGGCCTG

AGCTCGCCCGTCACAAAGAGCTTCAACAGGGGAGAGTGTTAA;

---

What is claimed is:

1. A humanized antibody or antigen-binding antibody fragment that binds specifically to human tau, comprising:

(a) a humanized mature heavy chain variable region comprising CDRs H1, H2, and H3 comprising SEQ ID NOs: 8, 9, and a sequence of LDF, respectively, and a humanized mature light chain variable region comprising CDRs L1, L2, and L3 comprising SEQ ID NOs: 12, 13, and 14, respectively;

(b) a humanized mature heavy chain variable region comprising CDRs H1, H2, and H3 comprising SEQ ID NOs: 8, 9, and a sequence of LDF, respectively, and a humanized mature light chain variable region comprising CDRs L1, L2, and L3 comprising SEQ ID NOs: 89, 13, and 14, respectively;

(c) a humanized mature heavy chain variable region comprising CDRs H1, H2, and H3 comprising SEQ ID NOs: 8, 87, and a sequence of LDF, respectively, and a humanized mature light chain variable region comprising CDRs L1, L2, and L3 comprising SEQ ID NOs: 12, 13, and 14, respectively;

(d) a humanized mature heavy chain variable region comprising CDRs H1, H2, and H3 comprising SEQ ID NOs: 8, 87, and a sequence of LDF, respectively, and a humanized mature light chain variable region comprising CDRs L1, L2, and L3 comprising SEQ ID NOs: 89, 13, and 14, respectively;

(e) a humanized mature heavy chain variable region comprising CDRs H1, H2, and H3 comprising SEQ ID NOs: 86, 87, and a sequence of LDF, respectively, and a humanized mature light chain variable region comprising CDRs L1, L2, and L3 comprising SEQ ID NOs: 12, 13, and 14, respectively;

(f) a humanized mature heavy chain variable region comprising CDRs H1, H2, and H3 comprising SEQ ID NOs: 86, 87, and a sequence of LDF, respectively, and a humanized mature light chain variable region comprising CDRs L1, L2, and L3 comprising SEQ ID NOs: 89, 13, and 14, respectively;

(g) a humanized mature heavy chain variable region comprising CDRs H1, H2, and H3 comprising SEQ ID NOs: 86, 88, and a sequence of LDF, respectively, and a humanized mature light chain variable region comprising CDRs L1, L2, and L3 comprising SEQ ID NOs: 12, 13, and 14, respectively;

(h) a humanized mature heavy chain variable region comprising CDRs H1, H2, and H3 comprising SEQ ID NOs: 86, 88, and a sequence of LDF, respectively, and a humanized mature light chain variable region comprising CDRs L1, L2, and L3 comprising SEQ ID NOs: 89, 13, and 14, respectively;

(i) a humanized mature heavy chain variable region comprising CDRs H1, H2, and H3 comprising SEQ ID NOs: 86, 92, and a sequence of LDF, respectively, and a humanized mature light chain variable region comprising CDRs L1, L2, and L3 comprising SEQ ID NOs: 12, 13, and 14, respectively; or (j) a humanized mature heavy chain variable region comprising CDRs H1, H2, and H3 comprising SEQ ID NOs: 86, 92, and a sequence of LDF, respectively, and a humanized mature light chain variable region comprising CDRs L1, L2, and L3 comprising SEQ ID NOs: 89, 13, and 14, respectively;

wherein Kabat positions L7, L10, L15, L17, L37, L45, L83, L86, L100, and L106 are occupied by S, S, L, E, Q, R, V, Y, Q, and I, respectively.

2. The humanized antibody or antigen-binding antibody A fragment of claim 1, provided Kabat positions H1, H5, H11, H20, H23, H38, H42, H43, H66, H75, H76, H81, H91, H93, H94, H108, and H109 are occupied by E, V, V, I, K, R, G, K, R, T, D, E, F, S, T, L, and V, respectively.

3. The humanized antibody or antigen-binding antibody fragment of claim 1, that is a humanized antigen-binding antibody fragment.

4. The humanized antibody or antigen-binding antibody fragment of claim 3, wherein the humanized antigen-binding antibody fragment is a single-chain antibody, a Fab, or a $Fab'_2$ fragment.

5. The humanized antibody or antigen-binding antibody fragment of claim 1, wherein the humanized antibody has a human IgG1 isotype.

6. The humanized antibody or antigen-binding antibody fragment of claim 1, wherein the humanized mature light chain variable region is fused to a light chain constant region and the humanized mature heavy chain variable region is fused to a heavy chain constant region.

7. The humanized antibody or antigen-binding antibody fragment of claim 6, wherein the heavy chain constant region is a mutant form of a natural human heavy chain constant region which has reduced binding to a Fcγ receptor relative to the natural human heavy chain constant region.

8. The humanized antibody or antigen-binding antibody fragment of claim 6, wherein the humanized mature heavy chain variable region is fused to a heavy chain constant region having the sequence of SEQ ID NO: 103 with or without the C-terminal lysine and/or the humanized mature light chain variable region is fused to a light chain constant region having the sequence of SEQ ID NO: 104.

9. The humanized antibody or antigen-binding antibody fragment of claim 1, wherein the humanized antibody has a human IgG2 or a human IgG4 isotype.

10. A pharmaceutical composition comprising the humanized antibody or antigen-binding antibody fragment of claim 1 and a pharmaceutically-acceptable carrier.

11. The humanized antibody or antigen-binding antibody fragment of claim 1, wherein:

the humanized mature heavy chain variable region comprises SEQ ID NO: 77 and the humanized mature light chain variable region comprises SEQ ID NO: 85;

the humanized mature heavy chain variable region comprises SEQ ID NO: 78 and the humanized mature light chain variable region comprises SEQ ID NO: 85;

the humanized mature heavy chain variable region comprises SEQ ID NO: 79 and the humanized mature light chain variable region comprises SEQ ID NO: 85;

the humanized mature heavy chain variable region comprises SEQ ID NO: 80 and the humanized mature light chain variable region comprises SEQ ID NO: 85;

the humanized mature heavy chain variable region comprises SEQ ID NO: 90 and the humanized mature light chain variable region comprises SEQ ID NO: 85; or the humanized mature heavy chain variable region comprises SEQ ID NO: 91 and the humanized mature light chain variable region comprises SEQ ID NO: 85.

12. The humanized antibody or antigen-binding antibody fragment of claim 11, wherein the humanized mature heavy chain variable region comprises SEQ ID NO: 77 and the humanized mature light chain variable region comprises SEQ ID NO: 85.

13. The humanized antibody or antigen-binding antibody fragment of claim 11, wherein the humanized mature heavy chain variable region comprises SEQ ID NO: 78 and the humanized mature light chain variable region comprises SEQ ID NO: 85.

14. The humanized antibody or antigen-binding antibody fragment of claim 11, wherein the humanized mature heavy chain variable region comprises SEQ ID NO: 79 and the humanized mature light chain variable region comprises SEQ ID NO: 85.

15. The humanized antibody or antigen-binding antibody fragment of claim 11, wherein the humanized mature heavy chain variable region comprises SEQ ID NO: 80 and the humanized mature light chain variable region comprises SEQ ID NO: 85.

16. The humanized antibody or antigen-binding antibody fragment of claim 11, wherein the humanized mature heavy chain variable region comprises SEQ ID NO: 90 and the humanized mature light chain variable region comprises SEQ ID NO: 85.

17. The humanized antibody or antigen-binding antibody fragment of claim 11, wherein the humanized mature heavy chain variable region comprises SEQ ID NO: 91 and the humanized mature light chain variable region comprises SEQ ID NO: 85.

* * * * *